United States Patent [19]

Apple et al.

[11] Patent Number: 5,567,809
[45] Date of Patent: Oct. 22, 1996

[54] METHODS AND REAGENTS FOR HLA DRBETA DNA TYPING

[75] Inventors: Raymond J. Apple, San Francisco; Henry A. Erlich, Oakland; Robert L. Griffith, Belmont; Stephen J. Scharf, Albany, all of Calif.

[73] Assignee: Hoffmann-La Roche Inc., Nutley, N.J.

[21] Appl. No.: 50,073

[22] PCT Filed: Dec. 6, 1991

[86] PCT No.: PCT/US91/09294

§ 371 Date: Apr. 22, 1993

§ 102(e) Date: Apr. 22, 1993

[87] PCT Pub. No.: WO92/10589

PCT Pub. Date: Jun. 25, 1992

Related U.S. Application Data

[63] Continuation-in-part of Ser. No. 623,098, Dec. 6, 1990, abandoned, which is a continuation-in-part of Ser. No. 491,210, Aug. 15, 1989, abandoned, which is a continuation of Ser. No. 899,344, Aug. 22, 1986, abandoned, which is a continuation-in-part of Ser. No. 839,331, Mar. 13, 1986, abandoned.

[51] Int. Cl.[6] .................................................. C07H 21/04
[52] U.S. Cl. .................. 536/24.3; 536/24.31; 536/24.33
[58] Field of Search ............................... 536/24.3, 24.31, 536/24.33

[56] References Cited

U.S. PATENT DOCUMENTS

| | | | |
|---|---|---|---|
| 4,582,788 | 4/1986 | Erlich ......................................... | 435/6 |
| 4,683,195 | 7/1987 | Mullis et al. ............................... | 435/6 |
| 4,889,818 | 12/1989 | Gelfand et al. ......................... | 435/194 |
| 4,965,188 | 10/1990 | Mullis et al. ............................... | 435/6 |
| 4,965,189 | 10/1990 | Owerbach .................................. | 435/6 |
| 5,110,920 | 5/1992 | Erlich ........................................ | 536/27 |

FOREIGN PATENT DOCUMENTS

| | | |
|---|---|---|
| 0237362 | 9/1987 | European Pat. Off. . |
| 8904875 | 6/1989 | WIPO . |
| 8911547 | 11/1989 | WIPO . |
| 8911548 | 11/1989 | WIPO . |

OTHER PUBLICATIONS

Todd et al, HLA-Dq$_\beta$ gene contributes to susceptibility and resistance to insulin14dependent diabetes mellitus, Nature-(Oct. 1987)329; 599–604.
Trowsdale et al., 1985, "Structure, Sequence and Polymorphism in the HLA–D Region," Immunological Reviews 85:5–43.
Bohme et al., 1985, "HLA–DR Beta Genes Vary in Number Between Different DR Specificities, Whereas the Number of DQ Beta Genes is Constant," J. Immunol. 135:2149–2155.
WHO Nomenclature Committee, 1990, "Nomenclature for Factors of the HLA System, 1989," Immunogenetics 31:131–140.
Gregersen et al., 1989, "First Domain Sequence Diversity of DR and DQ Subregion Alleles," Immunobiology of HLA 1:1027–1031.

Matsuyama et al., 1986, "Structural Relationships Between the DRBeta 1 and DRBeta 2 Subunits in DR4, 7, and w9 Haplotypes and the DRw53 (MT3) Specificity," J. Immunology 137(3):934–940.
Erlich et al., 1989, "Analysis of Isotypic and Allotypic Sequence Variation in the HLA–DRBeta Region Using the In Vitro Enzymatic Amplification of Specific DNA Segments," Immunobiology of HLA2:181–185.
Cairns et al., 1985, "Sequence Polymorphism of HLA DRB1 Alleles Relating to T-Cell-Recognized Determinants," 317:166–168.
Scharf et al., 1988, "Sequence Analysis of the HLA–DRB and HLA–DQB Loci From Three Pemphigus vulgaris Patients," Human Immunology 22:61–69.
Scharf et al., 1986, "Direct Cloning and Sequence Analysis of Enzymatically Amplified Genomic Sequences," Sciences 233:1076–1078.
Saiki et al., 1986, "Analysis of Enzymatically Amplified B–Globin and HLA–DQA DNA With Allele–Specific Oligonucleotide Probes," Nature 324:163–166.
Uryu et al, 1990, "A Simple and Rapid Method for HLA–DRB and –DQB Typing by Digestion of PCR–Amplified DNA With Allele Specific Restriction Endonucleases," Tiss. Ant. 35(1):20–31.
Horn et al., 1988, "Sequence Analysis of HLA Class II Genes From Insulin–Dependent Diabetic Individuals," Hum. Immunol. 21:249–263.
Todd et al., 1987, "HLA–DQB Gene Contributes to Susceptibility and Resistance to Insulin–Dependent Diabetes Mellitus" Nature 329:599–604.
Saiki et al., 1989, "Genetic Analysis of Amplified DNA With Immobilized Sequence–Specific Oligonucleotide Probes," Proc. Natl. Acad. Sci. USA 86:6230–6234.
AmpliType (TM) DQalpha DNA Typing Kit Package Insert.
Goa et al., 1990, "DNA Typing for Class II HLA Antigens With Allele–Specific or Group–Specific Amplification. I. Typing for Subsets of HLA–DR4," Hum. Immunol. 27:40–50.
Pollack et al., 1983, "Mixed Lymphocyte Reactions for Individuals With Phenotypic Identity for Specific HLA–B, DR Determinants: The Role of Linkage Disequilibrium and of Specific DR and Other Class II Determinants," J. Clinical Immunology 3(4):341–351.

(List continued on next page.)

*Primary Examiner*—Kenneth R. Horlick
*Attorney, Agent, or Firm*—George W. Johnston; Stacey R. Sias; Douglas A. Petry

[57] ABSTRACT

Primers for amplification of specific nucleic acid sequences of the second exon of HLA DRbeta genes and probes for identifying polymorphic sequences contained in the amplified DNA can be used in processes for typing homozygous or heterozygous samples from a variety of sources and for detecting allelic variants not distinguishable by serological methods. This HLA DRbeta DNA typing system can be used in a dot-blot format that is simple and rapid to perform, produces detectable signals in minutes, and can be used for tissue typing, determining individual identity, and identifying disease susceptible individuals.

3 Claims, 18 Drawing Sheets

OTHER PUBLICATIONS

Scharf et al., 1989, "Specific HLA–DQB and HLA–DRB1 Alleles Confer Susceptibility to Pemphigus vulgaris," Proc. Natl. Acad. Sci. USA 86:6215–6219.

Nepom et al., 1986, "Identification of HLA–Dw14 Genes in DR4 Rheumatoid Arthritis," Lancet pp. 1002–1005.

Fugger et al., 1989, "Typing for HLA–DPB1*03 and HLA–DPB1*06 Using Allele–Specific DNA In Vitro Amplification and Allele–Specific Oligonculeotide Probes. Detection of 'new'DPB1*06 Variants," Immunogenetics 30:208–213.

FIG. 2

| Cell Line | GH125 "Y" | CRX50 "K-GR" | CRX35 "F-DR" | CRX06 "I-DE" | CRX23 "A-H" | CRX56 "G" | CRX57 "V" | CRX04 "R" | CRX61 "S" | CRX62 "I-DK" | CRX63 "I-DR" | HLA-DRB DRB1* |
|---|---|---|---|---|---|---|---|---|---|---|---|---|
| QBL | + | | | | | | | | | | | 0301 |
| RSH | | + | | | | | | | | | | 0302 |
| SPOO1O | | | | | | + | | | | | | 1101 |
| HERLUF | | | + | | | | + | | | | | 1201 |
| KOSE | | | | + | | + | | | | | + | 1302/1401 |
| SLE | | | | + | + | + | | | | | | 1302 |
| HAG | | | | | | + | + | | + | + | | 1303 |
| AMALA | | | | | | + | | + | | | | 1402 |
| BAR P | | | + | + | | + | | | | | | 0402/DR "PEV" |
| ARC | | | + | | | + | + | | + | | | 0801 |
| SPL | | | + | | | | | | | | | 0802 |
| TAB | | | | | | + | | | + | | + | 0803 |

FIG. 6

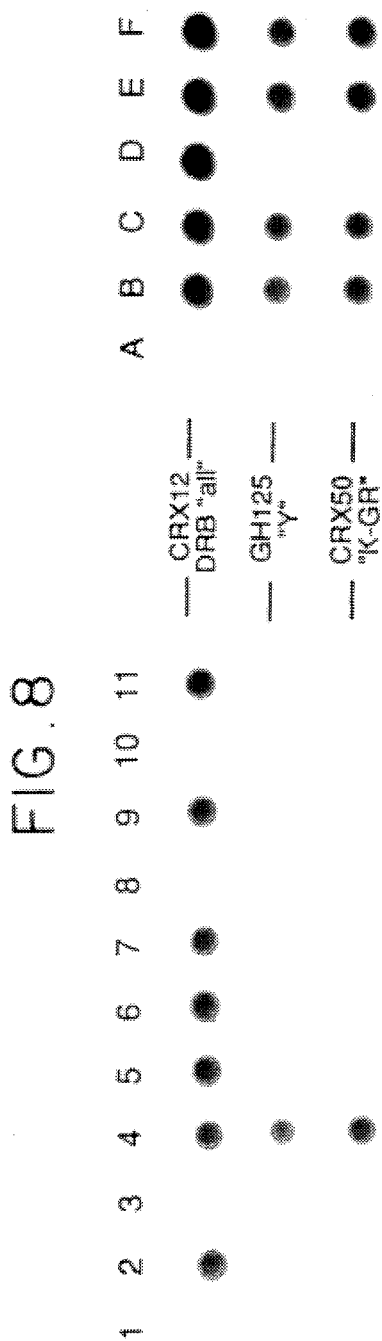

| # | CRX60 W-L-F | GH105 Q-D-Y | GH125 Y | CRX50 K-GR | GH59 V-H | GH122 E | CRX06 I-DE | CRX23 A-H | CRX49 G-YK | GH102 YSTG | GH111 K-DF | CRX61 S | HLA-DRB DRB1* |
|---|---|---|---|---|---|---|---|---|---|---|---|---|---|
| 555 | + | | | | + | | | | | | | | 0101/0403 |
| 593 | | | | | | | + | | + | | | | 0701/1301 |
| 634 | | | | | | | | | | + | | + | 0801/1001 |
| 766 | | | | | | | | | + | | | | 0701/0701 |
| 842 | | + | | | | + | | | | | | | DRw15/1101 |
| 863 | | + | + | + | | | | | | | | | DRw15/0301 |
| PSWS | | | | | + | + | | | | | | | 0404/DRw11 |
| 2426 | | | ND | ND | | | | | + | | + | | 0701/0901 |
| 2446 | | | ND | ND | | | | | + | | | | 0701/0701 |
| 2540 | + | | ND | ND | | + | | | | | | | 0101/1101 |
| 2671 | + | | ND | ND | | | | | + | | | | 0101/0701 |
| 2755 | | + | ND | ND | | | | | + | | | | DRw15/0701 |

FIG. 9A

| # | CRX53 K | CRX15 R-E | CRX56 G | CRX57 V | CRX04 R | GH54 V-S | CRX62 I-DK | CRX63 I-DR | CRX34 E-V | GH56 YSTS | CRX35 F-DR | CRX12 ALL | HLA-DRB DRB1* |
|---|---|---|---|---|---|---|---|---|---|---|---|---|---|
| 555 | | + | | | | | | | | | | | 0101/0403 |
| 593 | | | | + | + | + | | | | + | | + | 0701/1301 |
| 634 | | | | + | | | | | | | + | + | 0801/1001 |
| 766 | | | + | | | | | | | | | + | 0701/0701 |
| 842 | | | + | | | + | | | | + | + | + | DRw15/1101 |
| 863 | | | | + | | | | | | + | + | + | DRw15/0301 |
| PSWS | | | | + | + | | | | | + | | + | 0404/DRw11 |
| 2426 | | | ND | | | ND | | | | | | + | 0701/0901 |
| 2446 | | | ND | | | ND | | | | | | + | 0701/0701 |
| 2540 | | | ND | | + | ND | | | | + | + | + | 0101/1101 |
| 2671 | | | ND | | + | ND | | | | | | + | 0101/0701 |
| 2755 | | | ND | | | ND | | | | | + | + | DRw15/0701 |

FIG. 9B

| ALLELES | WLF 1 | WPR 2 | YSTS 3 | V-H 4 | GYK 5 | YSTG 6 | KDF 7 | EV-F 8 | E(58) 9 | A-H 10 | F-DE 11 | S 12 | FDR 13 | R 14 | K 15 | (R)R-E 16 | I-DE 17 | KGR 18 | Y 19 | I-DK 20 | I-DR 21 | VS 22 | All C |
|---|---|---|---|---|---|---|---|---|---|---|---|---|---|---|---|---|---|---|---|---|---|---|---|
| 0101 | + | | | | | | | | | | | | | | | | | | | | | | + |
| 0102 | + | | | | | | | | | | | | | | | | | | | | | | + |
| 0103 | + | | | | | | | | | | | | | | | | | | | | | | + |
| 1501 | | + | | | | | | | | | | | | | | | | | | | | | + |
| 1502 | | + | | | | | | | | | | | | | | | | | | | | | + |
| 1503 | | + | | | | | | | | | | | | | | | | | | | | | + |
| 1504 | | + | | | | | | | | | | | | | | | | | | | | | + |
| 1601 | | + | | | | | | | | | | | | | | | | | | | | | + |
| 1602 | | + | | | | | | | | | | | | | | | | | | | | | + |
| 0301 | | | + | | | | | | | | | | | | | | | | | | | | + |
| 0302 | | | + | | | | | | | | | | | | | | | | | | | | + |
| 0401 | | | | + | | | | | | | | | | | | | | | | | | | + |
| 0402 | | | | + | | | | | | | | | | | | | | | | | | | + |
| 0403 | | | | + | | | | | | | | | | | | | + | | | | | | + |
| 0404 | | | | + | | | | | | | | | | | | + | | | | | | | + |
| 0405 | | | | + | | | | | | | | | | + | + | | | | | | | | + |
| 0406 | | | | + | | | | | | | | + | | + | | | | | | | | | + |
| 0407 | | | | + | | | | | | | | | | | | + | | + | | | | | + |
| 0408 | | | | + | | | | | | | | | | + | | | | + | + | | | | + |
| 0409 | | | | + | | | | | | | | + | | | + | | | | | | | | + |
| 0410 | | | | + | | | | | | | | + | | + | | | | | | | | | + |

PROBES

PROBES

| PATTERNS | WLF 1 | WPR 2 | YSTS 3 | V-H 4 | GYK 5 | YSTG 6 | KDF 7 | EV-F 8 | E(58) 9 | A-H 10 | F-DE 11 | S 12 | FDR 13 | R 14 | K 15 | R-E 16 | I-DE 17 | KGR 18 | Y 19 | I-DK 20 | I-DR 21 | VS 22 | All C |
|---|---|---|---|---|---|---|---|---|---|---|---|---|---|---|---|---|---|---|---|---|---|---|---|
| DRB1*0101/0102 | + | | | | | | | | | | | | | + | | | | | | | | | + |
| DRB1*0103 | + | | | | | | | | | | | | | | | | + | | | | | | + |
| DRB1*15/16 | | + | | | | | | | | | | | | | | | | | | | | | + |
| DRB1*0301 | | | + | | | | | | | | | | | | | | | + | + | | | | + |
| DRB1*0302 | | | + | | | | | | | | | | | | | | | + | | | | | + |

DRB1*0301
Also possibly Heterozygous: DRB1 alleles 0301 & 0302, 0301 & 1403

DRB1*0302
Also possibly Heterozygous: DRB1 alleles 0302 & 1403

PROBES

| PATTERNS | WLF 1 | WPR 2 | YSTS 3 | V-H 4 | GYK 5 | YSTG 6 | KDF 7 | EV-F 8 | E(58) 9 | A-H 10 | F-DE 11 | S 12 | FDR 13 | R 14 | K 15 | (R)R-E 16 | I-DE 17 | KGR 18 | Y 19 | I-DK 20 | I-DR 21 | VS 22 | All C 23 |
|---|---|---|---|---|---|---|---|---|---|---|---|---|---|---|---|---|---|---|---|---|---|---|---|
| DRB1*0401 | | | | + | | | | | | | | | | | + | | | | | | | | + |
| DRB1*0402 | | | | + | | | | | | | | | | | | | + | | | | | | + |
| DRB1*0403/0406/0407 | | | | + | | | | | | | | | | | | + | | | | | | | + |
| DRB1*0404/0408 | | | | + | | | | | | | | | | + | | | | | | | | | + |
| DRB1*0405/0410 | | | | + | | | | | | | | + | | + | | | | | | | | | + |
| DRB1*0409 | | | | + | | | | | | | | + | | | + | | | | | | | | + |

Also possibly Heterozygous: DRB1 alleles 0404/0408 & 0405/0410

Also possibly Heterozygous: DRB1 alleles 0401 & 0409

PROBES

| PATTERNS | WLF 1 | WPR 2 | YSTS 3 | V-H 4 | GYK 5 | YSTG 6 | KDF 7 | EV-F 8 | E(58) 9 | A-H 10 | F-DE 11 | S 12 | FDR 13 | R 14 | K 15 | (R)R-E 16 | I-DE 17 | KGR 18 | Y 19 | I-DK 20 | I-DR 21 | VS 22 | All C |
|---|---|---|---|---|---|---|---|---|---|---|---|---|---|---|---|---|---|---|---|---|---|---|---|
| DRB1*1202 | | | | | | + | | | | | | | + | | | | | | | | | + | + |
| DRB1*1301/1302 | | | + | | | | | | | | | | | | | | | | | | | | + |
| DRB1*1303 | | | + | | | | | | | | | + | | | | | + | | | + | | | + |
| DRB1*1304 | | | + | | | | | | | | | + | + | | | | + | | | | | | + |
| DRB1*1305 | | | + | | | | | | | | | | | | | | | | | | | | + |

DRB1*1202
Also possibly Heterozygous: DRB1 alleles 1202 & 0802/0804

DRB1*1301/1302
Also possibly Heterozygous: DRB1 alleles 1301/1302 & 1403

DRB1*1303
Also possibly Heterozygous: DRB1 alleles 1303 & 1403

DRB1*1304
Also possibly Heterozygous: DRB1 alleles 1301/1302 & 1304, 1304 & 1403

DRB1*1305
Also possibly Heterozygous: DRB1 alleles 1305 & 1403

FIG. 12B

PROBES

| PATTERNS | WLF 1 | WPR 2 | YSTS 3 | V-H 4 | GYK 5 | YSTG 6 | KDF 7 | EV-F 8 | E(58) 9 | A-H 10 | F-DE 11 | S 12 | FDR 13 | R 14 | K 15 | (R)R-E 16 | I-DE 17 | KGR 18 | Y 19 | I-DK 20 | I-DR 21 | VS 22 | All C |
|---|---|---|---|---|---|---|---|---|---|---|---|---|---|---|---|---|---|---|---|---|---|---|---|
| DRB1*1401 | | | + | | | | | | | + | | | | | | + | | | | | | | + |
| DRB1*1402 | | | + | | | | | | | | | | | + | | | | | | | | | + |
| DRB1*1403 | | | + | | | | | | | | | | | | | | | | | | | | + |
| DRB1*1404 | | | | | | + | | | | + | | | | | | + | | | | | | | + |
| DRB1*0701/0702 | | | | | + | | | | | | | | | | | | | | | | | + | + |

DRB1*1401
Also possibly Heterozygous: DRB1 alleles 1401 & 1403

DRB1*1402
Also possibly Heterozygous: DRB1 alleles 1402 & 1403

DRB1*1403

DRB1*1404

DRB1*0701/0702

FIG. 13A

PROBES

| PATTERNS | WLF 1 | WPR 2 | YSTS 3 | V-H 4 | GYK 5 | YSTG 6 | KDF 7 | EV-F 8 | E(58) 9 | A-H 10 | F-DE 11 | S 12 | FDR 13 | R 14 | K 15 | KR-E 16 | I-DE 17 | KGR 18 | Y 19 | I-DK 20 | I-DR 21 | VS 22 | All C |
|---|---|---|---|---|---|---|---|---|---|---|---|---|---|---|---|---|---|---|---|---|---|---|---|
| DRB1*801 | | | | | | + | | | | | | + | + | | | | | | | | | | + |
| Also possibly Heterozygous: DRB1 alleles 0801 & 0802/0804 | | | | | | | | | | | | | | | | | | | | | | | |
| DRB1*0802/0804 | | | | | | + | | | | | | | + | | | | | | | | | | + |
| DRB1*0803 | | | | | | + | | | | | | + | | | | | | | | | | | + |
| DRB1*0901 | | | | | | | + | | | | | | | | | | | | | | | | + |
| DRB1*1001 | | | | | | | | + | | | | | | | | | | | | | | | + |

FIG. 13B

METHODS AND REAGENTS FOR HLA DRBETA DNA TYPING

CROSS-REFERENCE TO RELATED APPLICATIONS

This application is a continuation-in-part of Ser. No. 623,098, filed Dec. 6, 1990, abandoned, which is a continuation-in-part of Ser. No. 491,210, filed Aug. 15, 1989, abandoned, which is a continuation of abandoned Ser. No. 899,344, filed Aug. 22, 1986, abandoned, which is a continuation-in-part of abandoned Ser. No. 839,331, filed Mar. 13, 1986, abandoned, each of which is incorporated herein by reference.

BACKGROUND OF THE INVENTION

1. Field of the Invention

The present invention provides methods and reagents for DNA typing of HLA DRbeta (DRB) nucleic acids. The invention enables one to type homozygous or heterozygous samples from a variety of sources, including samples comprising RNA or cDNA templates, and to detect allelic variants not distinguishable by present serological, cellular, or biochemical methods. The present typing system facilitates typing tissue for transplantation, determining individual identity, and identifying disease susceptible individuals. The invention therefore has applications in the field of medicine generally and medical research and diagnostics specifically, the field of forensic science, and the field of molecular biology.

2. Description of Related Art

The HLA Class II proteins HLA DR, HLA DQ, and HLA DP are encoded by genes in the major histocompatibility complex (MHC) region on the short arm of human chromosome 6. The Class II proteins are heterodimeric glycoproteins consisting of an approximately 34 kD alpha chain and an approximately 29 kD beta chain. The Class II proteins are expressed on the cell surface of macrophages, B-cells, activated T-cells, and other cell types and are involved in binding and presenting antigen to helper T-lymphocytes. See the article entitled "Structure, function, and genetics of the Human Class II molecules" by Giles and Capra, 1985, *Adv. Immunol.* 37:1. In addition, the Class II proteins influence specific immune responsiveness by determining the repertoire of expressed T-cell receptors in mature T-lymphocytes. For a general review of the HLA Class II genes and proteins, see the article entitled "Structure, sequence and polymorphism in the HLA D region" by Trowsdale et al., 1985, *Immunol. Rev.* 85:5.

The Class II alpha and beta chains are encoded by separate genes, and the DP, DQ, and, DR genes are located in separate regions of the MHC. In the DR region, a single DRA locus, or gene, encodes the non-polymorphic DRalpha chain, but five different DRB loci, termed DRB1, DRB2 (now known as DRB6), DRB3, DRB4, and DRB5, encode the polymorphic DRbeta chain. Some loci are present only on certain haplotypes (such as DRB5 on the DR2 haplotype); in addition, the number of expressed DRB genes also varies between haplotypes. See the article entitled "HLA-DRbeta genes vary in number between different DR-specificities, whereas the number of DQbeta genes is constant" by Bohme et al., 1985, *J. Immunol.* 135:2149.

The number of distinct DRB1 alleles identified is continually increasing. The 1989 report from the WHO Nomenclature Committee for factors of the HLA system identified 34 distinct DRB1 alleles; these alleles are thought to express the serological DR specificities DR1 to DRw18. (see the article entitled "Nomenclature for factors of the HLA system, 1989" by the WHO Nomenclature Committee, 1990, *Immunogenetics* 31:131–140, incorporated herein by reference). By the 1990 report, the number of DRB1 alleles recognized had risen to 45 (see the article entitled "Nomenclature for factors of the HLA system, 1990" by the WHO Nomenclature Committee, 1991, *Immunogenetics* 33:301–309, incorporated herein by reference). The present invention provides the sequences of several newly discovered alleles.

The alleles of the DRB2 locus (now termed the DRB6 locus), which are present on DR1, DR2, and DRw10 haplotypes, are apparently not expressed. See the article entitled "Analysis of isotypic and allotypic sequence variation in the HLA DRB region using the in vitro enzymatic amplification of specific DNA segments" by Erlich et al., 1989, in *Immunobiology of HLA* (Dupont ed., Springer-Verlag, New York).

The alleles of the DRB3 locus, which is thought to encode the supertypic specificity DRw52 (DRw52a, DRw52b, and DRw52c), are present on the DR3, DRw6, DRw11, DRw12, DRw13, DRw14, DRw17, and DRw18 haplotypes.

The DRB4 locus, which has a single allele, encodes the DRw53 supertypic specificity and is present only on the DR4, DR7, and DRw9 haplotypes. See the article entitled "Structural relationships between the DRbeta1 and DRbeta.2 subunits in DR4, 7, and w9 haplotypes and the DRw53 (MT3) specificity" by Matsuyama et al., 1986, *J. Immunol.* 137:934.

The alleles of the DRB5 locus are present only on DR2 haplotypes. See the article entitled "Analysis of isotypic and allotypic sequence variation in the HLA DRB region using the in vitro enzymatic amplification of specific DNA segments," supra.

Polymorphism of the Class II DR antigens (proteins) is currently typed with allosera obtained from multiparous women in a microcytotoxicity assay on purified B lymphocytes. In addition, cellular typing protocols capable of greater specificity and based on either the specificity of alloreactive T-cell clones or the proliferative response of T-cell cultures to stimulation by homozygous typing cells (HTCs) have been developed.

These cellular-based analyses define the Dw specificities that further subdivide many of the serologically defined antigens, e.g., the five Dw subtypes of DR4. See the article entitled "Sequence polymorphism of HLA DRbeta I alleles relating to T cell recognized determinants" by Cairns et al., 1985, *Nature* 317:166. Both the serological and cellular assay procedures, however, are difficult and time-consuming. HLA DR DNA typing protocols based on restriction fragment length polymorphisms (RFLP) have also been developed. See U.S. Pat. No. 4,582,788, incorporated herein by reference. However, these RFLP-based analyses require large amounts of high molecular weight DNA, are labor intensive, and the limited number of informative restriction enzymes in rum limits the results obtained.

The advent of the polymerase chain reaction (PCR) has facilitated the analysis and manipulation of complex genomic DNA. The PCR process enables one to amplify a specific sequence of nucleic acid starting from a very complex mixture of nucleic acids and is more fully described in U.S. Pat. Nos. 4,683,195; 4,683,202; 4,889,818; and 4,965,188, and European Patent Publication Nos. 237,362 and 258,017, each of which is incorporated herein by reference.

The PCR process has also facilitated typing the Class II HLA DNA of an individual. Scientists have studied the polymorphic second exon of DRB loci in genomic DNA by designing oligonucleotide primers and using those primers to amplify the sequences of interest. See the article entitled "Sequence analysis of the HLA DRB and HLA DQB loci from three *Pemphigus vulgaris* patients" by Scharf et al., 1988, *Hum. Immunol.* 22:61.

When the PCR primers contain restriction enzyme recognition sequences, the amplified DNA can be cloned directly into sequencing vectors, and the nucleotide sequence of the amplification product can be readily determined. See the article entitled "Direct cloning and sequence analysis of enzymatically amplified genomic sequences" by Scharf et al., 1986, *Hum. Immunol.* 233:1076.

The amplified DNA can also be studied by detection methods that employ sequence-specific oligonucleotide (SSO) probes. See the article entitled "Analysis of enzymatically amplified beta-globin and HLA DQalpha DNA with allele-specific oligonucleotide probes" by Saiki et al., 1986, *Nature* 324:163.

Despite these advances, the complexity of the HLA DRbeta genes has prevented the development of an informative and efficient means for determining the HLA DRbeta DNA type of an individual. The present invention meets the need for an efficient, informative DRbeta DNA typing method by providing novel processes and reagents. These novel processes and reagents have in turn led to the discovery of previously unknown DRbeta alleles, which can also be typed and identified by the present method.

The present typing system can be used to type cDNA synthesized from mRNA and to type and study the expression of DRB genes in tissues, transgenic systems, disease states, and cell line. Cells that do not express the DR antigens or show unusual seroreactivity, such as tumor cells, can be readily typed. Moreover, samples from unusual sources, e.g., ancient DNAs or forensic samples, can be typed, even when the DNA sample is degraded or when only very small quantities are available for analysis.

Because PCR can amplify a fragment of target DNA over a million-fold, and because the present system can employ PCR-generated nucleic acid, radioactively labeled probes are not necessary, and nonisotopic SSOs covalently coupled to horseradish peroxidase (HRP) provide sufficient sensitivity for detection. The presence of the specifically bound HRP-labeled probes of the invention can be detected in a simple dot-blot format by chromogenic dye or chemiluminescent substrates in a matter of minutes.

SUMMARY OF THE INVENTION

The present invention provides amplification and detection methods, generic and allele or group specific amplification primers, nonisotopic sequence specific oligonucleotide (SSO) probes, including probes for identifying previously unknown alleles at the DRB1 locus, and kits for practicing the methods, that together provide a rapid, simple and precise system for typing the HLA DRB alleles, including those that cannot be distinguished by serological methods.

In one aspect, the present invention provides a method for determining the DRbeta DNA type of nucleic acid in a sample, which method comprises (a) amplifying any nucleic acids in the sample that contain a DRbeta gene second exon; (b) hybridizing said nucleic acid amplified in step (a) to a first panel of oligonucleotide probes under conditions such that said probes hybridize only to exactly complementary sequences greater than ten nucleotides in length; (c) amplifying a specific subset of nucleic acids in the sample that contain DRbeta gene second exon sequences; (d) hybridizing said nucleic acid amplified in step (c) with a second panel of oligonucleotide probes under conditions such that said probes hybridize only to exactly complementary sequences greater than ten nucleotides in length; and (e) determining from the pattern of probe hybridization in steps (b) and (d) the DRbeta alleles from which the DRbeta DNA in said sample originates.

In another aspect, the present invention provides a method for determining whether a sample comprises nucleic acid from the DRB1 allele of a serological type selected from the group consisting of the DR1, DR2, DR4, DR7, DRw9, and DRw10 types, which method comprises (a) amplifying the DRB1 nucleic acid in the sample; and (b) hybridizing said nucleic acid amplified in step (a) to a panel of oligonucleotide probes under conditions such that said probes hybridize only to exactly complementary sequences greater than ten nucleotides in length, and wherein said probes hybridize to unique polymorphic sequences encoding amino acid residues 9 to 16 of the DRB1 second exon.

BRIEF DESCRIPTION OF THE FIGURES

FIG. 2 shows the results of DRB1 specific amplification and detection; see Example 2.

FIG. 6 shows the tabulation of probe hybridization results to determine the DRB type; see Example 6.

FIG. 8 shows the HLA DRB DNA subtyping of DR3 cell lines; see Example 7.

FIG. 9a shows the first half of the tabulation of probe hybridization results used to determine the HLA DRB DNA type of heterozygous and other unusual samples, as described in Example 7.

FIG. 9b shows the second half of the tabulation of probe hybridization results used to determine the HLA DRB DNA type of heterozygous and other unusual samples, as described in Example 7.

FIG. 10 shows the tabulation of probe hybridization results to determine the HLA DRB DNA type; see Example 9.

FIGS. 11, 12, and 13 show the tabulation of probe hybridization results to determine DRB allele type; see Example 9.

DETAILED DESCRIPTION OF THE INVENTION

Figure 1:
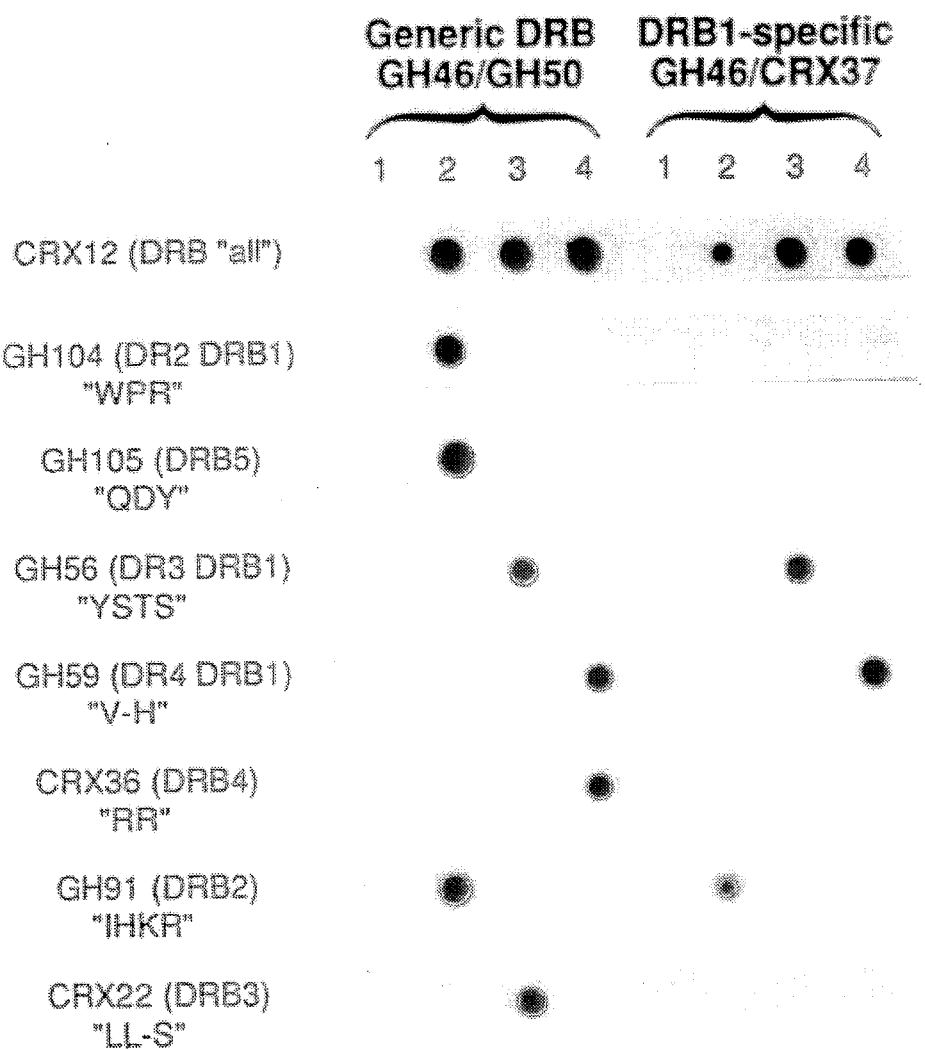
FIG. 1 shows the results of DRB generic and DRB1 specific amplification and detection; see Example 2.

The present invention provides an HLA DRB typing system and sequence specific oligonucleotide probes (SSOs) for analyzing DRB alleles. The invention can be used to type heterozygous samples from a variety of sources, including cDNA templates, and can be used to detect allelic variants not distinguishable by serological methods. This typing system can utilize a dot-blot format that is simple and rapid to perform, produces detectable signals in minutes, and will prove valuable for tissue typing and determining individual identity and disease susceptibility.

The present invention provides methods for detecting and identifying HLA DRB alleles. The number of distinct DRB1 alleles identified is continually increasing. The 1989 WHO Nomenclature Committee report listed 34 DRB1 alleles; this set of alleles is herein referred to as the 1989 allele set. The 1990 WHO Nomenclature Committee report listed 45 alleles; this set of alleles is herein referred to as the 1990 allele set. In addition, the present invention provides the sequences of several newly discovered alleles.

The diversity of DRB loci, the most highly polymorphic of the HLA Class II loci, and the large number of alleles at these loci in the population make difficult the process of identifying the particular DRB loci and alleles from which a nucleic acid in a sample originates. The present invention allows one to make this determination with great specificity and so can be used to identify the particular individual from whom a sample was taken. This discrimination power in turn leads to the applications of the invention in the field of forensic science.

Because PCR (or other amplification processes) can be used to amplify very small amounts of DNA (or degraded DNA), the present invention can be used to type HLA DRB DNA from unusual sources, such as a buccal swab, a single hair, and even DNA from preserved ancient specimens. With the latter samples, analysis of the alleles from prehistoric sources, e.g., early hominids, is possible. For purposes of the present invention, "amplification" is defined by any process that increases the amount of target nucleic acid in a sample by means of nucleic acid replication or transcription.

The present method can be used for DRB DNA typing of cells that do not express the DRB genes. The method is also suitable, however, for DRB DNA typing of cDNA synthesized from DRB mRNA. The latter method facilitates the study of the expression of HLA DRB in various cell lines or tissues and can be used to determine if there is an association between HLA DRB expression and susceptibility to transformation, autoimmunity, or other health conditions.

The research potential of the present invention should in no way obscure the immediate clinical applications. The genes and gene products of the MHC play a central role in the immunological state of an individual, and particular MHC gene products are associated with disease resistance and susceptibility. Because the present invention allows the determination of the MHC DRB gene products in a sample, the invention also has applications in the field of medicine, particularly for medical diagnostic methods.

The discriminating power of this system will be valuable in typing potential transplantation donors, where very precise HLA DRB matching appears to be critical in minimizing risk of rejection or graft versus host disease. See the article entitled "Mixed lymphocyte reactions for individuals with phenotypic identity for specific HLA B, DR determinants: The role of linkage disequilibrium and of specific DR and other Class II determinants" by Pollack et al., 1983, *J. Clin. Immunol.* 3:341. Disease susceptibility studies have shown that single nucleotide differences in the DRB alleles can be medically significant. See the articles entitled "Specific HLA-DQB and HLA-DRB1 alleles confer susceptibility to *Pemphigus vulgaris*" by Scharf et al., 1989, *Proc. Natl. Acad. Sci. USA* 86:6215; and "Identification of HLA-Dw14 genes in DR4+ Rheumatoid Arthritis" by Nepom et al., 1986, *Lancet* page 1002.

In addition to the above benefits, the present invention also provides methods for identifying previously unknown DR alleles, and related primers, probes, and methods for the identification of any DRB allele. Unusual patterns of SSO probe hybridization using this typing system identify new alleles, as exemplified by the DNA typing of the "Beguit" cell line (see Example 7). This cell line showed an unusual pattern of probe hybridization at the DRB1 locus, revealing a previously unreported sequence, now designated DRB1*1103 (SEQ ID NO: 27).

In similar fashion, analysis by the present method of the DRB1 alleles in a patient with Lyme disease revealed a new pattern of probe hybridization. DRB1 allele sequences were cloned from genomic DNA of the patient and sequenced. The sequence of one DRB1 allele of the patient is different from any previously reported DRB1 allele and was originally designated as DR'LY10' (also DRB1*LY10). The other allele in the patient was DRB1*0402. The DR'LY10' allele has regions of sequences similar to DRB1*0801, *0802, *0803, and *1201 at the 5'-end and to *1401 at the 3'-end. The present invention provides probes for distinguishing the DR'LY10' allele from other DRB alleles. The DR'LY10' allele is now designated as DRB1*1404 (SEQ ID NO: 40).

Other newly discovered alleles of the DRB1 locus are DRB1*1305 (SEQ ID NO: 36), originally designated as DR'PEV', DRB1*1303 (SEQ ID NO: 34), and DRB1*1105 (SEQ ID NO: 29), originally designated as DRB1*BUGS. Each was discovered when analysis by the methods of the present invention revealed a new pattern of probe hybridization. Subsequent sequence analysis of each allele revealed the sequence variation causing the novel hybridization pattern. The present invention provides primers and probes for distinguishing the newly discovered alleles from other DRB alleles.

The present invention also provides kits for making practice of the present DRB typing method more convenient. One type of kit includes both amplification and typing reagents. Another kit contains only one or more DRB probes of the invention. In either kit, the probes can be labeled or unlabeled or attached to a solid support. The primers, if present in the kit, can also be labeled to facilitate detection, i.e., to bind a signal development reagent or for immobilization. The kits can also contain reagents that facilitate detection of probe hybridization, i.e., the chromogenic substrate TMB and streptavidin-linked horseradish peroxidase. In brief, the reagents useful in practicing the present method can be packaged in any configuration that promotes utilization of the invention.

The nucleotide sequence of the second exon of each allele along with the encoded amino acid sequence are provided in the Sequence Listing section. Table 1 and 2, below, presents equivalent nucleotide sequence information for the alleles in the 1989 allele set, but in a manner which facilitates comparison. Table 1 also shows the nucleic acid sequence and the encoded amino acid sequence in both three and one letter codes for allele DRB*0101. Similarly, Table 3 presents equivalent amino acid sequence information, but using one letter amino acid codes. The sequence identification number of each allele is shown below. All alleles with the exception of DRB1*1503, DRB1*0303, and DRB1*1105 are listed in the 1990 WHO Nomenclature Committee report, supra (1990 allele set). For the sequence of DBR1*1503, see also Demopolos et al., 1991, *Human Immunology* 30:41–44.

The nucleotide sequences of alleles which do not appear in Tables 1, 2, and 3 are provided in Table 9 below in addition to the Sequence Listing section.

| Allele | SEQ ID NO: |
|---|---|
| DRB1*0101: | SEQ ID NO: 1 |
| DRB1*0102: | SEQ ID NO: 2 |
| DRB1*0103: | SEQ ID NO: 3 |
| DRB1*0301: | SEQ ID NO: 4 |
| DRB1*0302: | SEQ ID NO: 5 |
| DRB1*0303: | SEQ ID NO: 6 |
| DRB1*0401: | SEQ ID NO: 7 |
| DRB1*0402: | SEQ ID NO: 8 |
| DRB1*0403: | SEQ ID NO: 9 |
| DRB1*0404: | SEQ ID NO: 10 |
| DRB1*0405: | SEQ ID NO: 11 |
| DRB1*0406: | SEQ ID NO: 12 |
| DRB1*0407: | SEQ ID NO: 13 |
| DRB1*0408: | SEQ ID NO: 14 |
| DRB1*0409: | SEQ ID NO: 15 |
| DRB1*0410: | SEQ ID NO: 16 |
| DRB1*0411: | SEQ ID NO: 17 |
| DRB1*0701: | SEQ ID NO: 18 |
| DRB1*0801: | SEQ ID NO: 19 |
| DRB1*0802: | SEQ ID NO: 20 |
| DRB1*0803: | SEQ ID NO: 21 |
| DRB1*0804: | SEQ ID NO: 22 |
| DRB1*0901: | SEQ ID NO: 23 |
| DRB1*1001: | SEQ ID NO: 24 |
| DRB1*1101: | SEQ ID NO: 25 |
| DRB1*1102: | SEQ ID NO: 26 |
| DRB1*1103: | SEQ ID NO: 27 |
| DRB1*1104: | SEQ ID NO: 28 |
| DRB1*1105: | SEQ ID NO: 29 |
| DRB1*1201: | SEQ ID NO: 30 |
| DRB1*1202: | SEQ ID NO: 31 |
| DRB1*1301: | SEQ ID NO: 32 |
| DRB1*1302: | SEQ ID NO: 33 |
| DRB1*1303: | SEQ ID NO: 34 |
| DRB1*1304: | SEQ ID NO: 35 |
| DRB1*1305: | SEQ ID NO: 36 |
| DRB1*1401: | SEQ ID NO: 37 |
| DRB1*1402: | SEQ ID NO: 38 |
| DRB1*1403: | SEQ ID NO: 39 |
| DRB1*1404: | SEQ ID NO: 40 |
| DRB1*1405: | SEQ ID NO: 41 |
| DRB1*1501: | SEQ ID NO: 42 |
| DRB1*1502: | SEQ ID NO: 43 |
| DRB1*1503: | SEQ ID NO: 44 |
| DRB1*1601: | SEQ ID NO: 45 |
| DRB1*1602: | SEQ ID NO: 46 |
| DRB2*0101: | SEQ ID NO: 47 |
| DRB3*0101: | SEQ ID NO: 48 |
| DRB3*0201: | SEQ ID NO: 49 |
| DRB3*0202: | SEQ ID NO: 69 |
| DRB3*0301: | SEQ ID NO: 50 |
| DRB4*0101: | SEQ ID NO: 51 |

-continued

| Allele | SEQ ID NO: |
|---|---|
| DRB5*0101: | SEQ ID NO: 52 |
| DRB5*0102: | SEQ ID NO: 53 |
| DRB5*0201: | SEQ ID NO: 54 |
| DRB5*0202: | SEQ ID NO: 55 |

In Tables 1, 2, and 3, below, all sequences except the recently identified "PEV" and "LY10" alleles are listed in the 1989 WHO HLA nomenclature report, supra, and the DRB1*0101 nucleotide sequence serves as the consensus sequence. The inferred amino acid sequence for the consensus sequence is written in one and three letter code above the nucleotide sequence. Sequence homology is indicated by dashed lines, and letters indicate polymorphic bases. The designated SSO probes and primers written at the right end of the alignments in the tables are the same sense as, or complementary to, the regions of sequences boxed. Where two names appear at the end of an alignment, the left-most name refers to the left-most box, the right-most name refers to the right-most box. The probe CRX12 (SEQ ID NO: 63) hybridizes to the region shown in all DRB alleles.

Table 1, in three parts designated A, B, and C, shows the nucleotide sequence of 35 DRB1 alleles corresponding to the DR specificities DR1 to DRw18.

Table 2 shows the nucleotide sequence alignments for the alleles of the DRB2, DRB3, DRB4, and DRB5 loci. The major regions of sequence polymorphism for the DRB1 alleles are localized to amino acid positions 9–16, 25–34, 67–74, and 86; the remainder of the second exon sequence is relatively invariant.

Table 3 shows the inferred amino acid sequence alignment encoded by the DRB alleles. Analysis of the amino acid sequences reveals a complex but restricted pattern of polymorphism with particular polymorphic sequences found in several different alleles. However, some polymorphic sequences are unique for each allele. The DR1, DR2, DR4, DR7, DRw9, and DRw10 alleles each have unique polymorphic sequences at the first hypervariable region (positions 9 to 16) of the DRB1 locus that can be used to determine the serological DR specificities by SSO typing. By contrast, the DR3, DRw11, and DRw6 alleles share a polymorphic epitope, "YSTS," and cannot be distinguished by a probe for this region alone but can be distinguished by the polymorphisms at other positions in each allele. Similarly, DRw8 and DRw12 also cannot be distinguished in this region.

TABLE 1A

HLA - DR BETA DNA SEQUENCE ALIGNMENT

| DRB1* | R F L W Q L K F E C H F F N G T E R V R L L E R C I Y N Q<br>Arg Phe Leu Trp Gln Leu Lys Phe Glu Cys His Phe Phe Asn Gly Thr Glu Arg Val Arg Leu Leu Glu Arg Cys Ile Tyr Asn Gln<br>CACGTTTCTTGTGGCAGCTTAAGTTTGAAT GTCATTTCTTCAAT GGGACGGAGCGGGTGCGGTTGCTGGAAAGAT GCATCTATAACCAA | |
|---|---|---|
| 0101: | ---------------------------------------------------------------------------------------- | CRX60 |
| 0102: | ---------------------------------------------------------------------------------------- | |
| 0103: | ---------------------------------------------------------------------------------------- | |
| 1501: | ------C------AGG--G--------------------------C--------C-----A-T----G | GH104 |
| 1502: | ------C------AGG--G--------------------------C--------C-----A-T----G | |
| 1601: | ------C------AGG--G--------------------------C--------C-----A-T----G | |
| 1602: | ------C------AGG--G--------------------------C--------C-----A-T----G | |
| 0301: | ---------GA-T-CTC--C--C-----G----------------AC-------C-----A-T--C--G | GH56 |
| 0302: | ---------GA-T-CTC--C--C-----G-----------------C-------C-----A-T--C--G | |
| 0401: | ---------GA------G-----ACA--G--------C--------C-------C-----A-T--C--G | GH59 |
| 0402: | ---------GA------G-----ACA--G--------C--------C-------C-----A-T--C--G | |
| 0403: | ---------GA------G-----ACA--G--------C--------C-------C-----A-T--C--G | |
| 0404: | ---------GA------G-----ACA--G--------C--------C-------C-----A-T--C--G | |
| 0405: | ---------GA------G-----ACA--G--------C--------C-------C-----A-T--C--G | |
| 0406: | ---------GA------G-----ACA--G--------C--------C-------C-----A-T--C--G | |
| 0407: | ---------GA------G-----ACA--G--------C--------C-------C-----A-T--C--G | |
| 0408: | ---------GA------G-----ACA--G--------C--------C-------C-----A-T--C--G | |
| 1101: | ---------GA-T-CTC--C--C-----G-----------------C-------C-----A-T-----G | GH56 |
| 1102: | ---------GA-T-CTC--C--C-----G-----------------C-------C-----A-T-----G | |
| Beguit: | ---------GA-T-CTC--C--C-GG--G----------T------C-------C-----A-T-----G | |
| 1104: | ---------GA-T-CTC--C--C-----G-----------------C-------C-----A-T-----G | |
| 1201: | ---------GA-T-CTC--C--C-----G-----------------A-------G----CA-T--C--G | GH102 |
| 1301: | ---------GA-T-CTC--C--C-----G-----------------C-------C-----A-T--C--G | GH56 |
| 1302: | ---------GA-T-CTC--C--C-----G-----------------C-------C-----A-T--C--G | |
| 1303: | ---------GA-T-CTC--C--C-----G-----------------C-------C-----A-T--C--A | |

TABLE 1A-continued

HLA - DR BETA DNA SEQUENCE ALIGNMENT

| | | | | | | | | |
|---|---|---|---|---|---|---|---|---|
| 1401: | ------ | --GA--T--CTC----C----C---- | G | ------ | C------ | C----A--T----C | ------G | |
| 1402: | ------ | --GA--T--CTC----C----C---- | G | ------ | C------ | G----A--T----C | ------G | |
| DR'PEV': | ------ | --GA--T--CTC----C----C---- | G | ------ | C------ | C----A--T----C | ------G | |
| DR'LY10: | ------ | --GA--T--CTC----C--GG----G----T | ------ | ------ | C------ | C----A--T----C | ------G | GH102 |
| 0701: | ----C--- | ---GG------A--A--G | ------ | ------A----C | ------ | ------CT--T------G | ------ | CRX49 |
| 0801: | ------ | --GA--T--CT--C----C--GG----G----T | ------ | ------ | C------ | C----A--T------ | ------ | GH102 |
| 0802: | ------ | --GA--T--CT--C----C--GG----G----T | ------ | ------ | C------ | C----A--T------ | ------ | |
| 0803: | ------ | --GA--T--CT--C----C--GG----G----T | ------ | ------ | C------ | C----A--T------ | ------ | |
| 0901: | ------ | --AA------GA------ | G | ------ | C------ | AT----C--C------G | ------ | GH111 |
| 1001: | ------ | --GA--G----G------ | G | ------ | C------ | C----G----C | ------ | CRX34 |

TABLE 1B

| DRB1* | +35 E Glu GAG | E Glu GAG | S Ser AGT | V Val CCG | R Arg TGC | F Phe GCT | +40 D Asp TCG | S Ser ACA | D Asp GCG | V Val ACG | G Gly TGG | E Glu GGA | +45 Y Tyr GTA | R Arg CCG | A Ala GGA | V Val GTA | T Thr CCG | E Glu GAG | +50 L Leu TAC | G Gly GGG | R Arg CGG | P Pro GGC | D Asp GGT | A Ala GAG | +55 E Glu CTG | Y Tyr GGC | W Trp AGG | N Asn CCG | S Ser GAC | Q Gln GCC | +60 Y Tyr GAT | W Trp GCC | N Asn GAG | S Ser TAC | Q Gln TGG | | | | | AAC | AGC | AG | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 0101: | | | | | | | | | | | | | | | | | | | | | | | | | | | | | | | | | | | | | | | | | | | CRX12 |
| 0102: | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | | | | | | | |
| 0103: | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | | | | | | | |
| 1501: | --- | --- | --- | --- | --- | --- | --- | --- | --- | --- | --- | --- | --- | T | --- | --- | --- | --- | --- | --- | --- | --- | --- | --- | --- | C | - | T | --- | --- | --- | --- | --- | --- | --- | | | | | | | |
| 1502: | --- | --- | --- | --- | --- | --- | --- | --- | --- | --- | --- | --- | --- | T | --- | --- | --- | --- | --- | --- | --- | --- | --- | --- | --- | C | - | T | --- | --- | --- | --- | --- | --- | --- | | | | | | | |
| 1601: | --- | --- | --- | --- | --- | --- | --- | --- | --- | --- | --- | --- | --- | --- | --- | --- | --- | --- | --- | --- | --- | --- | --- | --- | --- | C | - | T | --- | --- | --- | --- | --- | --- | --- | | | | | | | |
| 1602: | --- | --- | --- | --- | --- | --- | --- | --- | --- | --- | --- | --- | --- | T | --- | --- | --- | --- | --- | --- | --- | --- | --- | --- | --- | C | - | T | --- | --- | --- | --- | --- | --- | --- | | | | | | | |
| 0301: | --- | AA | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | | | | | | | |
| 0302: | --- | AA | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | | | | | | | |
| 0401: | --- | A | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | | | | | | | |
| 0402: | --- | A | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | | | | | | | |
| 0403: | --- | A | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | | | | | | | |
| 0404: | --- | A | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | | | | | | | |
| 0405: | --- | A | --- | --- | --- | --- | --- | --- | --- | --- | --- | --- | --- | --- | --- | --- | --- | --- | --- | --- | --- | --- | --- | AGC | --- | --- | --- | --- | --- | --- | --- | --- | --- | --- | --- | | | | | | CRX61 | |
| 0406: | --- | A | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | | | | | | | |
| 0407: | --- | A | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | | | | | | | |
| 0408: | --- | A | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | | | | | | | |
| 1101: | --- | A | --- | --- | --- | --- | --- | --- | --- | --- | --- | --- | --- | T | --- | --- | --- | --- | --- | --- | --- | --- | --- | AG | --- | --- | --- | --- | --- | --- | --- | --- | --- | --- | --- | | | | | | GH122 | |
| 1102: | --- | A | --- | --- | --- | --- | --- | --- | --- | --- | --- | --- | --- | T | --- | --- | --- | --- | --- | --- | --- | --- | --- | AG | --- | --- | --- | --- | --- | --- | --- | --- | --- | --- | --- | | | | | | | |
| Beguit: | --- | A | --- | --- | --- | --- | --- | --- | --- | --- | --- | --- | --- | T | --- | --- | --- | --- | --- | --- | --- | --- | --- | AG | --- | --- | --- | --- | --- | --- | --- | --- | --- | --- | --- | | | | | | | |
| 1104: | --- | A | --- | --- | --- | --- | --- | --- | --- | --- | --- | --- | --- | T | --- | --- | --- | --- | --- | --- | --- | --- | --- | AG | --- | --- | --- | --- | --- | --- | --- | --- | --- | --- | --- | | | | | | | |
| 1201: | CT | -C | --- | --- | --- | --- | --- | --- | --- | --- | --- | --- | --- | T | --- | --- | --- | --- | --- | --- | --- | --- | --- | TC | --- | --- | --- | --- | --- | --- | --- | C | --- | --- | --- | | | | | | GH54 | |
| 1301: | --- | AA | --- | --- | --- | --- | --- | --- | --- | --- | --- | --- | --- | T | --- | --- | --- | --- | --- | --- | --- | --- | --- | --- | --- | --- | --- | --- | --- | --- | --- | --- | --- | --- | --- | | | | | | | |

TABLE 1B-continued

| | | | | | | |
|---|---|---|---|---|---|---|
| 1302: | --AA-- | --T-- | | | | |
| 1303: | --A-- | | | | | |
| 1401: | --T-- | | --AGC-- | | | CRX61 |
| 1402: | --AA-- | | --C--G--C-- | | | CRX23 |
| DR'PEV': | --AA-- | --T-- | | | | |
| DR'LY10: | --T-- | | --C--G--C-- | | | CRX23 |
| 0701: | --T-- | --A-- | --TC-- --C-- | | | GH54 |
| 0801: | --A-- | | --AGC-- | | | CRX61 |
| 0802: | --A-- | | | | | |
| 0803: | --A--A-- | | --AGC-- | | | CRX61 |
| 0901: | --AA-- | | --T-- --C-- | | | GH54 |
| 1001: | --A--C-- --A-- | | | | | |

TABLE 1C

| DRB1*: | +65 K D L L E Q R R A A +70 V D T Y C R H N Y +80 G V G E S F T V Q R R +90 Lys Asp Leu Leu Glu Gln Arg Arg Ala Ala Val Asp Thr Tyr Cys Arg His Asn Tyr Gly Val Gly Glu Ser Phe Thr Val Gln Arg Arg | |
|---|---|---|
| 0101: | AAGGACCTCCTGGAGCAGAGGCGGGCCGCGGTGGACACCTACTGCAGACACAACTACGGGGTTGGTGAGAGCTTCACAGTGCAGCGGCGA | CRX04, CRX56 |
| 0102: | ------------------------------------------------------------------------------------------ | CRX56 |
| 0103: | ---------------A----------AG--CGA-------------------------------------------C--TG--------- | CRX06, CRX57 |
| 1501: | ---------------A----------GC----------------------------------------------------TG------- | CRX56 |
| 1502: | ---------------A----------GC--------------------------------------------------T---------- | CRX57 |
| 1601: | ---------------T---------AG--C--------------------------------------------------TG------- | CRX35, CRX56 |
| 1602: | ------------------------AG--C-----------C----------------------------------------TG------ | CRX56 |
| 0301: | -------------------------------A---G--CG--------A----------------------------------TG---- | CRX50, CRX57 |
| 0302: | -------------------------------A---G--CG--------A---------------------------------------- | CRX53 |
| 0401: | -------------------------------A--------------------------------------------------TG----- | CRX06, CRX57 |
| 0402: | ---------------A---------AG--CGA------A--------------------------------------------TG---- | CRX15 |
| 0403: | -------------------------------A--------------------------------------------------TG----- | CRX04 |
| 0404: | -------------------------------A--------------------------------------------------TG----- | CRX56 |
| 0405: | -------------------------------A------------------------------------------------T-------- | CRX57 |
| 0406: | -------------------------------A--------------------------------------------------TG----- | CRX15, CRX56 |
| 0407: | -------------------------------A------------------------------------------------T-------- | CRX57 |
| 0408: | -----------------------------------------A---------------------------------------------- | CRX04 |
| 1101: | ---------------T---------AG--C---------------------------------------------------TG------ | CRX35 |
| 1102: | ---------------A---------AG--CGA-----------------------------------------------TG-------- | CRX06, CRX57 |
| Beguit: | ---------------T---------AG--CGA-----------------------------------------------TG-------- | CRX68 |
| 1104: | ---------------T---------AG--C------------------------------------------------TG--------- | CRX35 |

TABLE 1C-continued

| | | | | | | |
|---|---|---|---|---|---|---|
| 1201: | ---A------AG--C--- | --------- | ---T----- | --------- | C--TG----- | CRX63 |
| 1301: | ---A------AG--CGA- | --------- | --------- | --------- | ---TG----- | CRX06, CRX57 |
| 1302: | ---A------AG--CGA- | --------- | --------- | --------- | --------- | CRX56 |
| 1303: | ---A------AG--C--A | --------- | --------- | --------- | --------- | |
| 1401: | ----------G------- | --------- | ---T----- | ---A----- | ---TG----- | CRX62 |
| 1402: | ------------------ | --------- | --------- | --------- | --------- | CRX57 |
| DR'PEV': | ---T------AG--C--- | --------- | --------- | ---A----- | ---TG----- | CRX04, CRX56 |
| DR'LY10: | ----------G------- | --------- | ---T----- | ---A----- | --------- | CRX35 |
| 0701: | ---A------G--C---- | G--CA---- | ---GTG--- | --------- | --------- | CRX57 |
| 0801: | ---T------AG--C--- | ---CT---- | --------- | --------- | --------- | CRX35 CRX56 |
| 0802: | ---T------AG--C--- | ---CT---- | --------- | --------- | ---G----- | |
| 0803: | ---A------AG--C--- | ---CT---- | --------- | --------- | --------- | CRX56 |
| 0901: | ---T----------G--- | ---A----- | ---GTG--- | --------- | --------- | CRX63 |
| 1001: | ----------G------- | --------- | ---T----- | --------- | ---A----- | CRX56 |

TABLE 2

| | +10 | +15 | +20 | +25 | +30 | |
|---|---|---|---|---|---|---|
| | R F L W Q L K F E C H F F F N G T E R V R L L E R C I Y N Q | | | | | |
| | Arg Phe Leu Trp Gln Leu Lys Phe Glu Cys His Phe Phe Phe Asn Gly Thr Glu Arg Val Arg Leu Leu Glu Arg Cys Ile Tyr Asn Gln | | | | | |
| DRB1*0101: | CACGTTTCTTGTGGCAGCTTAAGTTTGAATGTCATTTCTTCAATGGGACGGAGCGGGTTGCTGGAAAGATGCATCTATAACCAA | | | | | CRX60 |
| DRB2*0101: | ---------GA-----GC-----G----------------A-------------A--AC--AAC----A---C----A-GGGAG | | | | | GH91 |
| DRB3*0101: | ---------GA--T--G-----C-------------------------------AC-----------C---A-T--C------G | | | | | GH57 |
| DRB3*0201: | ---------GA--T-----------C---------------------------AC------------G---CA-T--C------G | | | | | GH58 |
| DRB3*0202: | ---------GA--T-----C---------------------------------------------------G---CA-T--C------G | | | | | |
| DRB3*0301: | ---------GA--T-----C-----------------------------------------------------G---A-T--C------G | | | | | |
| DRB4*0101: | ---------GA-----GC-----G-----------------------------C-G-----A---T--AAC---ATC---A--- | | | | | GH51 |
| DRB5*0101: | ---------CA-----GA-----G-----------------------------C------------C-C-C--G--------- | | | | | GH105 |
| DRB5*0102: | ---T-----CA-----GA-----G-----------------------------C------------C-C-C--G--------- | | | | | |
| DRB5*0201: | ---------CA-----GA-----G-----------------------------C------------C-C-C--G--------- | | | | | |
| DRB5*0201: | ---T-----CA-----GA-----G-----------------------------C------------C-C-C--G--------- | | | | | |

| | +35 | +40 | +45 | +50 | +55 | +60 | |
|---|---|---|---|---|---|---|---|
| | E E S V R F D S D V G E Y R A V T E L G R P D A E Y W N S Q | | | | | | |
| | Glu Glu Ser Val Arg Phe Asp Ser Asp Val Gly Glu Tyr Arg Ala Val Thr Glu Leu Gly Arg Pro Asp Ala Glu Tyr Trp Asn Ser Gln | | | | | | |
| DRB1*0101: | GAGGAGTCCGTGCGCTTCGACAGCGACGTGGGGGAGTACCGGGCGGTGACGGAGCTGGGGCGGCCTGATGCCGAGTACTGGAACAGCCAG | | | | | | CRX12 |
| DRB2*0101: | -----------AA--C----C----------------------A------------TC--A--A--- | | | | | | |
| DRB3*0101: | -----------T--C---------------------A--T--A--A-T-----------TC-------C------ | | | | | | GH54 |
| DRB3*0201: | -----------A--C----------------G------------------------------C--T------ | | | | | | |
| DRB3*0202: | -----------A--C----------------G------------------------------C--T------ | | | | | | |
| DRB3*0301: | -----------T---------------------------------------------TC-------C------ | | | | | | GH54 |
| DRB4*0101: | -----------A--C---------A-A--T--C----------------------A-----C--T------ | | | | | | |
| DRB5*0101: | -----------GA--T----------------------------------------------C--T------ | | | | | | |
| DRB5*0102: | -----------AA---------------------------------------------------C--T------ | | | | | | |
| DRB5*0201: | -----------AA---------------------------------------------------C--T------ | | | | | | |
| DRB5*0201: | -----------AA------G----------------------------------------------C--T------ | | | | | | |

TABLE 2-continued

|  | +65 | +70 | +75 | +80 | +85 | +90 |  |
|---|---|---|---|---|---|---|---|
|  | K D L L E Q R R A A V D T Y C R H N Y G V G E S F T V Q R |  |  |  |  |  |  |
|  | Lys Asp Leu Leu Glu Gln Arg Arg Ala Ala Val Asp Thr Tyr Cys Arg His Asn Tyr Gly Val Gly Glu Ser Phe Thr Val Gln Arg |  |  |  |  |  |  |
| DRB1*0101: | AAGGACCTCCTGGAGCAGAGGC GGGCCGCGGTGGACACCTACTGCAGAC ACAACTACGGGGTTGGTGAGAGC TTCACAGTGCAGCGG |  |  |  |  |  |  |
| DRB2*0101: | ---GAA------G---AT-----A-AA-- | | | | | | |
| DRB3*0101: | ------------------A---G-CG--------AT----- | | | | | | |
| DRB3*0201: | ------------------A---G-CA--------AT----- | | | | | |  --TG---------------- | CRX50, CRX56 |
| DRB3*0202: | ------------------A---G-CA--------AT----- | | | | | | | CRX57 |
| DRB3*0301: | ------------------A---G-CA--------AT----- | | | | | |  --TG---------------- | CRX57 |
| DRB4*0101: | ------------G-----------A----------T----- | | | | | |  --TG---------------- | CRX57 |
| DRB5*0101: | -------T-----AG-C-----C------------------ | | | | | | | |
| DRB5*0102: | -------T-----AG-C-----C------------------ | | | | | | --C--TG---------------- | CRX35, CRX56 |
| DRB5*0201: | -------------A-------GC------------------ | | | | | | --C--TG---------------- | |
| DRB5*0202: | -------------A-------GC------------------ | | | | | | | |

TABLE 3

ALIGNMENT OF HLA-DRB1 PROTEIN SEQUENCES

```
                        10         20         30         40         50         60         70         80         90
λ-CONSENSUS  RFLEQ*KECHFFNGTERVRFLDRYFY*QEEYVRFDSDVGEYRAVTELGRPDAEYWNSQKDLLEQ*RAAVDTYCRHNYGVGESFTVQRRI-

DRB1*0101:   ----W--L-F-------------------L-E-CI--N--S------------------------R----------------------    DR1—Dw1
DRB1*0102:   ----W--L-F-------------------L-E-CI--N--S------------------------R----------------------    DR1—Dw20
DRB1*0103:   ----W--L-F-------------------L-E-CI--N--S---------------------I--DE---------AV-----------   DR1—Dw'BON'
DRB1*1501:   ----W--P-R-------------------------N--S-----------F--------------I----A------V-----------   DR2—DRw15
DRB1*1502:   ----W--P-R-------------------------N--S-----------F--------------I----A-----------------   DR2—DRw15
DRB1*1601:   ----W--P-R-------------------------N--S--------------------------F--DR------------------   DR2—DRw16
DRB1*1602:   ----W--P-R-------------------------N--S-----------------------------DR------------------   DR2—DRw16
DRB1*0301:   -------YSTS------------------Y------HN--N----------------------------K--GR--N-----------   DR3—DRw17
DRB1*0302:   -------YSTS------------------Y------E-HN-N----------------------------K--GR--N-----V-------  DR3—DRw18
DRB1*0401:   ------V-H--------------------H-----------------------------------K-----------------------  DR4—Dw4
DRB1*0402:   ------V-H--------------------H-------------------------------I---DE---R-E--------V-------  DR4—Dw10
DRB1*0403:   ------V-H--------------------H-------------------------------------R-E-------V-------     DR4—Dw13
DRB1*0404:   ------V-H--------------------H-------------------------------------R---------V-------     DR4—Dw14
DRB1*0405:   ------V-H--------------------H-----------------------S-------------R---------V-------     DR4—Dw15
DRB1*0406:   ------V-H--------------------H-----------------------S-------------R-E---V-------         DR4—Dw'KT2'
DRB1*0407:   ------V-H--------------------H-------------------------------------R-E-------V-------     DR4—Dw13.2
DRB1*0408:   ------V-H--------------------H-------------------------------------R-----------V---------  DR4—Dw14.2
DRB1*1101:   -------YSTS------------------H-------------------------------------F--DR-------------     DR5—Dw11.1
DRB1*1102:   -------YSTS------------------H-------------------------------------I--DE-------V-----    DR5—Dw11.2
DRB1*1103:   -------YSTS------------------H-------------------------------------F--DE-------------     DR5—Dw11.3
                                                                                                      (BEGUIT)
DRB1*1104:   -------YSTS---------------N-----------------------F------------------F--DR------V-----   DR5—Dw11
DRB1*1301:   -------YSTS---------------HN-----------------------N--------------I--DE-------------     DRw6—DRw13
DRB1*1302:   -------YSTS---------------HN-----------------------N--------------I--DE-------------     DRw6—DRw13
DRB1*1303:   -------YSTS-----------------F-----------------------S-------------I--DK-------------     DRw6—DRw13
DRB1*1401:   -------YSTS---------------HN-F-------E----------------A--H--------RR--E-------V-------   DRw6—DRw14
DRB1*1402:   -------YSTS---------------HN-------------------------------------R------------V-------  DRw6—DRw14
"DR PEV":    -------YSTG--Y------------HN-F---------------------F-----A--H---------F--DR--------------
"LY10":      ----W--G-YK--------------Q--E--L--N--F-----------------V--S-------I--DR--GQ----V---------
DRB1*0701:   -------YSTG--Y-----------------N-----------------------V--S-------F--DR--L---------------   DR7
DRB1*0801:   -------YSTG--Y-----------------N-----------------------S----------F--DR--L---------------   DRw8.1
DRB1*0802:   -------YSTG--Y-----------E-H-HN----A----R----------------S-------I--DR--L---------------   DR8.2
DRB1*0803:   -------A-C--------------L---E--HN----F-----------------V--S-------I--DR--E--V-----------   DRw8.3
DRB1*0901:   ----K--D-F---------------Y-H-GI--N----------------------------------F--RR--E--V-----------  DRw9
DRB1*1001:   ----EV-F-----------------L-E-RVHN----A-Y----------------------------RR---------------     DRw10
DRB1*1201:   -------YSTG--Y-----------L-E-H-HN--LL---------------------V--S------I--DR-----------Y-----  DRw12
DRB1*0101:   -------A-C---------I------MK-QY-N--IHKR--NLP---E--FQ----V--N----GI--EN--DK---------------   DR52a
DRB2*0101:   -------LR-S--------------Y---HN---FL--------------------------------K--GR--N--------------  DRw52a
DRB3*0101:   -------LL-S--------------E--H-HN---A--------R-----------------------K--GQ--N-----V--------  DRw52b
DRB3*0201:   -------A-C------------L---WN-I--I--N------A-YN--L--Q----------------K--GQ--N-----V--------  DRw52c
DRB4*0101:   -------Q-D-Y-------------H-DI--N--DL-----------------------------------RR--E-------V-------  DR2—Dw2
DRB5*0101:   -------Q-D-Y-------------H-GI--N-------------------------------------F--DR------------      DR2—Dw12
DRB5*0102:   -------Q-D-Y-------------H-GI--N-------------------------------------F--DR------------      DR2—Dw12
DRB5*0201:   ----C--Q-D-Y-------------H-GI--N----------------------------------------I--A-----------AV  DR2—Dw21
```

The classical serologically defined DR types (except DR3 and DRw6) can be distinguished by amplifying with the generic DRB primers GH46 (SEQ ID NO: 67) and GH50 (SEQ ID NO: 68) and analyzing the amplification products with the first panel of probes, shown in Table 4. The allele specificities shown in Table 4 are with respect to the 1989 allele set. For purposes of the present invention, "generic primers" are PCR primers that hybridize to DRB gene second exon sequences and can be used to amplify any allele of any DRB locus. Because of the hybridization site of GH50 (SEQ ID NO: 68), one cannot probe for polymorphisms at position 86 (referring to the amino acid sequence) of the second exon when the product of amplification was generated with primer GH50 (SEQ ID NO: 68). An alternate primer that can be used to generate products than can be analyzed for position 86 polymorphisms is DRB151 (SEQ ID NO: 227), 5'-CCGAATTCGCCGCTGCACTGT-GAAGCT-3'.

solutions contain 0.1% SDS. Each probe is conjugated to HRP at the 5'-end.

This PCR/SSO DRbeta typing system is useful for "subtyping" the serologically defined DR haplotypes. For example, the cell line "KOSE" is homozygous for DRw6 when typed serologically; however, PCR/SSO DRbeta typing reveals that "KOSE" has two different DRw6 alleles, DRB1*1302 and DRB1*1401.

Samples that may be DR3 or DRw6 can be distinguished by amplifying with the DRB1 specific primers GH46 (SEQ ID NO: 67) and CRX37 (SEQ ID NO: 73) and analyzing the amplification products with the probes GH125 (SEQ ID NO: 94) and CRX50 (SEQ ID NO: 75) from the second panel of probes, shown in Table 5. The allele specificities shown in Table 5 are with respect to the 1989 allele set.

TABLE 4

First Panel of HLA DRB Typing SSO Probes

| Probe | SEQ ID NO: | Epitope | HLA DRB Alleles (DRB1*) | Wash (SSPE, °C.) |
|---|---|---|---|---|
| CRX60 | SEQ ID NO: 79 | "W-L-F" | 0101, 0102, 0103 | 0.4X, 42 |
| GH105 | SEQ ID NO: 91 | "Q-D-Y" | DRB5 | 0.1X, 42 |
| GH104 | SEQ ID NO: 90 | "W-P-R" | 1501, 1502, 1601, 1602 | 0.2X, 42 |
| GH59 | SEQ ID NO: 87 | "V-H" | 0401–0408 | 0.2X, 42, 20 |
| CRX06 | SEQ ID NO: 61 | "I-DE" | 0103, 0402, 1102, 1301, 1302 | 0.1X, 42 |
| GH122 | SEQ ID NO: 93 | "E" | 1101, 1102, 1103, 1104 | 0.2X, 42 |
| CRX23 | SEQ ID NO: 66 | "A-H" | 1401, DR "LY10" | 0.1X, 42 |
| CRX35 | SEQ ID NO: 71 | "F-DR" | 1601, 1101, 1104, DR "PEV", 0801, 0802 | 0.2X, 42 |
| CRX49 | SEQ ID NO: 74 | "G-YK" | 0701, 0702 | 1.0X, 42 |
| GH102 | SEQ ID NO: 89 | "YSTG" | 0801, 0802, 0803, 1201, DR "LY10", 1404 | 0.1X, 42 |
| GH111 | SEQ ID NO: 92 | "K-D-F" | 0901 | 0.4X, 42 |
| CRX34 | SEQ ID NO: 70 | "EV" | 1001 | 0.4X, 42 |
| CRX04 | SEQ ID NO: 60 | "R" | 0101, 0102, 0403, 0404, 0405, 0406, 0407, 0408, 1402 | 0.1X, 42 |
| GH56 | SEQ ID NO: 86 | "YSTS" | 0301, 0302, 1101–1104, 1301–1303, 1401, 1402, DR "PEV" | 0.2X, 42 |
| CRX68 | SEQ ID NO: 84 | "F-DE" | 1103 | 0.2X, 42 |
| CRX12 | SEQ ID NO: 63 | DRB "ALL" | All HLA-DRB alleles | 0.2X, 42 |

The probes shown in Table 4 are hybridized and then washed for 15 minutes at 42° C., except for GH59 (SEQ ID NO: 87), which is washed for 20 minutes at 42° C. All SSPE wash

TABLE 5

Second Panel of HLA DRB Typing SSO Probes

| Probe | SEQ ID NO: | Epitope | HLA DRB Alleles (DRB1*) | Wash (SSPE, °C.) |
|---|---|---|---|---|
| GH125[a] | SEQ ID NO: 94 | "Y" | 0301 | 0.2X, 50 |
| CRX50[a] | SEQ ID NO: 75 | "K-GR" | 0301, 0302 | 0.2X, 50 |
| CRX53[a] | SEQ ID NO: 76 | "K" | 0401 | 0.5X, 55 |
| CRX15[a] | SEQ ID NO: 64 | "R-E" | 0403, 0406, 0407 | 0.4X, 55 |
| CRX62 | SEQ ID NO: 81 | "I-DK" | 1303 | 0.2X, 42 |
| CRX63 | SEQ ID NO: 82 | "I-DR" | 0803, 1201 | 0.2X, 42 |
| CRX61 | SEQ ID NO: 80 | "S" | 0405, 1303, 0801, 0803 | 0.1X, 42 |
| GH54[a] | SEQ ID NO: 85 | "V-S" | 0701, 0901, 1201 | 0.2X, 42 |
| CRX56[a] | SEQ ID NO: 86 | "G" | 0101, 0103, 0302, 0401, 0405, 0407, 0408, 1101, 1302, 1303, 0701, 0901, 1001, 1402, DR "PEV", 0801, 0802, 0803, 1502, | 0.2X, 42 |

TABLE 5-continued

Second Panel of HLA DRB Typing SSO Probes

| Probe | SEQ ID NO: | Epitope | HLA DRB Alleles (DRB1*) | Wash (SSPE, °C.) |
|---|---|---|---|---|
| CRX57[a] | SEQ ID NO: 78 | "V" | 1601, 1602 0301, 0402, 0403, 0404, 0406, 1102, 1103, 1104, 1301, DR "LY10," 1401, 1501 | 0.1X, 42 |
| CRX12 | SEQ ID NO: 63 | DRB "ALL" | All HLA DRB alleles | 0.2X, 42 |

For the probes shown in Table 5, all SSPE wash solutions contain 0.1% SDS. In addition, probes marked "a" require DRB1 specific amplification with primers GH46/CRX37 (SEQ ID NO: 67/SEQ ID NO: 73). CRX15 (SEQ ID NO: 64) is hybridized at 50° C. instead of 42° C. Each probe is conjugated to HRP at the 5'-end. The probes CRX56 (SEQ ID NO: 77) and CRX57 (SEQ ID NO: 78) do not completely base-pair with the epitope "G" and epitope "V" alleles, respectively, because the probes contain one fewer G residue than the alleles. Probes modified to include the G residue missing in CRX56 (SEQ ID NO: 77) and CRX57 (SEQ ID NO: 78) are within the scope of the present invention.

For purposes of the present invention, "DRB1 specific" primers are primer pairs that comprise at least one primer that hybridizes to an intron sequence flanking the second exon of the DRB1 gene, which primer will not hybridize to the other DRB genes. Table 6 shows the nucleotide sequence of the DRB1 and DRB3 introns of the DR3 haplotype, from the last 10 codons prior to the start of the 3' downstream intron. The sequence for CRX37 (SEQ ID NO: 73) is underlined; the solid arrow indicates the direction of extension of the primer. The asterisks indicate sequence differences between the DRB1 and DRB3 intron sequences. The segments of the 3' downstream introns are listed in the Sequence Listing as SEQ ID NO: 314 (DRB1) and SEQ ID NO: 315 (DRB3); sequences upstream of the intron are in the allele sequences.

find DRB1 specific primer sequences for amplifying the DRB1 gene second exon from all DR haplotypes.

The HLA DRB1 alleles can be distinguished with greater specificity by amplifying with the generic and DRB1 specific primers and analyzing with both panels (Tables 4 and 5) of probes as required. The alleles of the 1989 allele set that cannot be distinguished with the specific probes in Tables 4 and 5 are the four DR2 subtypes DRB1*1501, *1502, *1601, and *1602 and the DR4 subtypes DRB1*0403 and DRB1*0406.

The DRB1 specific PCR primers are capable of reproducibly amplifying the DRB1 sequences from all but the DR2, DR7, and DR9 haplotypes. The primer CRX37 (SEQ ID NO: 73) was designed from intron nucleotide sequences from DR3, DR4, and DRw6 haplotypes. See the article entitled "Sequence Analysis of HLA Class II Genes from Insulin-Dependent Diabetic Individuals" by Horn et al., 1988, *Hum. Immunol.* 1:249.

The present invention provides a number of allele specific and group specific primers in addition to the DRB1 specific primer pair GH46/CRX37 (SEQ ID NO: 67/SEQ ID NO: 73). These primers are shown below. For the sequence of AB60, see Todd et al., 1987, *Nature* 329:599.

TABLE 6

| AA Seq: | 85 Val | Val | Glu | Ser | Phe | 90 Thr | Val | Gln | Arg | Arg | ← TCGCGCCGCGCCCTTAAG CRX37 |
|---|---|---|---|---|---|---|---|---|---|---|---|
| DRB1 NT: | GTT | GTG | GAG | AGC | TTC | ACA | GTG | CAG | CGG | CGA | GGTGAGCGCGGCGCGGCGGGG...... |
|  |  |  |  |  |  |  |  |  |  |  | ** * * * * |
| DRB3 NT: | GTT | GTG | GAG | AGC | TTG | ACA | GTG | CAG | CGG | CGA | GGTGAGCATGTCGGGGGGCGG...... |

| Intron | Seq. ID No. | Sequence |
|---|---|---|
| DRB1 | SEQ ID NO: 314 | 5'-GGTGAGCGCGGCGCGGCGGGG |
| DRB3 | SEQ ID NO: 315 | 5'-GGTGAGCATGTCGGGGGGCGG |

The DR3, DR4, and DRw6 haplotypes appear to be evolutionarily distinct from DR2, DR7, and DR9 haplotypes. There may be differences in the intron sequences of these alleles such that the primer is too mismatched to prime extension. Because the DRB1 alleles may have diverged in evolution prior to gene duplication, it may prove difficult to

| AB54 | SEQ ID NO: 56 | 5'-GGGGATCCTGGAGCAGGTTAAACA-3' |
| AB60 | SEQ ID NO: 57 | 5'-CCGAATTCCGCTGCACTGTGAAGCTCTC-3' |
| AB82 | SEQ ID NO: 58 | 5'-GGGGATCCTGGAGTACTCTACGTC-3' |
| AB83 | SEQ ID NO: 59 | 5'-GGGGATCCTGTGGCAGCCTAAGAGG-3' |

For example, DR4 specific amplification can be achieved with PCR primer pair AB54/AB60 (SEQ ID NO: 56/SEQ ID NO: 57) (PCR profile: 35 cycles of: ramp to 94° C.; 30 seconds denaturing at 94° C.; 30 seconds annealing and extending at 65° C.). DR3, DR5, and DR6 group specific amplification can be achieved with PCR primer pair AB82/AB60 (SEQ ID NO: 58/SEQ ID NO: 57) (35 cycles of: ramp to 96° C.; 30 seconds denaturing at 96° C.; 30 seconds annealing and extending at 65° C.). DR2 specific amplification can be achieved with PCR primer pair AB83/AB60 (SEQ ID NO: 59/SEQ ID NO: 57) (35 cycles of: ramp to 96° C.; 30 seconds denaturing at 96° C.; 30 seconds annealing and extending at 70° C.).

Specific alleles can be detected after group specific amplification with the epitope specific probes described herein; for instance, DRB1*160 1 can be detected after DR2 specific amplification with the AB83/AB60 (SEQ ID NO: 59/SEQ ID NO: 57) primer pair with an "F-DR" epitope specific probe.

Detection of alleles of the DR2 haplotype can be difficult, but such difficulty can be overcome by the group specific primers and the typing methods of the present invention. In the generic primer amplification of DRB alleles from DR2 haplotypes, both the DRB1 and DRB5 loci are amplified. Although one could use an "F" (at position 47) epitope specific DNA probe to determine the serologic DRw15 and DRw16 subtypes, "F" occurs also in 0301, some DRw13 alleles, and in all DRw11 and DRw12 alleles; other methods can provide more complete discrimination. Thus, a group specific primer designed to hybridize to the sequence encoding the epitope "I-A" will amplify the DRB1*1501 and DRB1*1502 alleles, and the amplified product will hybridize with a "WPR" epitope specific DNA probe. The primer DRB150 (SEQ ID NO: 226) (5'-TGTCCACCGCGGC-CCGCGCCT-3') is a primer designed to perform such an allele specific amplification (with GH46 (SEQ ID NO: 67)). The DRB5*0201 and DRB5*0202 alleles will also amplify with a group (or epitope) specific "I-A" primer, but as these alleles occur only with the DRB*1601 and DRB1*1602 alleles, the result of probe hybridization will be epitope "QDY" positive and "WPR" negative.

In addition, one should note that because the DRB1 specific primers exemplified herein do not amplify DR2 alleles, the DR2 specific amplification described above can be carried out in the same reaction tube and at the same time as the DRB1 specific amplification. Other allele and group specific primers and amplification methods are described in the Examples.

The extensive allelic diversity at the HLA DRB loci, like that of the other Class II beta genes, is localized primarily to the second exon. In general, the pattern of second exon sequence polymorphism, when present in the population at a particular DRB locus, is a patchwork, with specific polymorphic segments found in a variety of different alleles. In principle, such shared epitopes among different alleles could reflect either common ancestry, gene conversion, or convergent evolution. For purposes of oligonucleotide typing, however, this patchwork pattern of polymorphism means that many alleles cannot be identified by hybridization to a single oligonucleotide but can be identified by a unique pattern of hybridization with a panel of probes.

The sequence-specific oligonucleotide probes of the invention, called "SSOs," when employed in the present methods under the appropriate hybridization and wash conditions, are extremely specific, capable of distinguishing single nucleotide polymorphisms. The SSOs of the invention, unlike the probes used in RFLP methods, can be used to determine not only if alleles are different but also where and how the alleles differ.

In a preferred embodiment, these probes comprise the same sequence as, or a sequence complementary to, the regions of DNA of each allele boxed in Tables 1 and 2. For example, the probe CRX60 (SEQ ID NO: 79) is specific for the DNA encoding the amino acids "W-L-F" and can hybridize uniquely to the DR1 allele. The probe CRX49 (SEQ ID NO: 74) is specific for the amino acids encoding "G-YK" and hybridizes to the DR7 allele; other examples will be apparent upon consideration of the Tables.

While a single probe (i.e., GH56 (SEQ ID NO: 86)) can be used to distinguish DR3, DRw11, and DRw6 from the other DR serotypes, additional probes are required to distinguish between DR3, DRw11, and DRw6. The GH56+GH122 (SEQ ID NO: 86+SEQ ID NO: 93) probe combination, which hybridizes to DNA encoding the "YSTS" and "E" epitopes (codons 10 to 13 and 58) on DRw11, can be used to distinguish DRw11 from DR3 and DRw6. Likewise, the probe combinations GH56+CRX06 (SEQ ID NO: 86+SEQ ID NO: 61) corresponding to the "YSTS" and "I-DE" (codon 67 to 71) epitopes can be used to distinguish DRw6 (DRB1*1301 and DRB1*1302 but not DRB1*1303, which has the epitope "I-DK" but is still DRw6) from DRw11 and DR3.

The combinations of the SSO probes shown in Table 4 used to determine the majority of the serological DR types are shown in Table 7.

TABLE 7

Combinations of SSO Probes to Determine Serological DR Types

| DR Type | Probe(s) |
| --- | --- |
| DR1 Dw1 | CRX60 + CRX04 |
| DR1 Dw "BON" | CRX60 + CRX06 |
| DR2 | GH105 |
| DR4 Dw4 | GH59 + CRX53 |
| DR4 Dw10 | GH59 + CRX06 |
| DR4 Dw13, 14, 15 | GH59 + CRX04 |
| DR3, w11, w6 | GH56 |
| DRw11.1 | GH56 + GH122 + CRX35 |
| DRw11.2 | GH56 + GH122 + CRX06 |
| DRw12, DRw8.3 | GH102 + CRX63 |
| DRw13 (1301, 1302) | GH56 + CRX06 |
| DRw14 Dw16 | GH56 + CRX04 |
| DRw14 Dw9 | GH56 + CRX23 |
| DR7 | CRX49 |
| DRw8.1, w8.2 | GH102 + CRX35 |
| DR9 | GH111 |
| DRw10 | CRX34 |
| DRw12, all DRw8 | GH102 |

Further subdivision of the DR serotypes (Table 4) requires the use of probes shown in Table 5, as shown in Table 8, below.

TABLE 8

Combinations of SSO Probes to Distinguish 31 of 34 HLA DRB1 Alleles (1989 set)

| DRB1* | Probe(s) |
| --- | --- |
| 0101 | CRX60 + CRX04 + CRX56 |
| 0102 | CRX60 + CRX04 |
| 0103 | CRX60 + CRX06 + CRX56 |
| DR2 | GH105 |
| 0301 | GH56 + GH125 + CRX50 + CRX57 |
| 0302 | GH56 + CRX50 + CRX56 |
| 0401 | GH59 + CRX53 + CRX56 |
| 0402 | GH59 + CRX06 + CRX57 |

TABLE 8-continued

Combinations of SSO Probes to Distinguish 31 of 34 HLA DRB1 Alleles (1989 set)

| DRB1* | Probe(s) |
|---|---|
| 0403, 0406 | GH59 + CRX15 + CRX57 + CRX04 |
| 0404 | GH59 + CRX04 + CRX57 |
| 0405 | GH59 + CRX04 + CRX61 + CRX56 |
| 0407 | GH59 + CRX15 + CRX56 + CRX04 |
| 0408 | GH59 + CRX04 + CRX56 |
| 1101 | GH122 + GH56 + CRX35 + CRX56 |
| 1102 | GH122 + GH56 + CRX06 + CRX57 |
| 1103 | GH122 + GH56 + CRX57 + CRX68 |
| 1104 | GH122 + GH56 + CRX35 + CRX57 |
| 1201 | GH102 + GH54 + CRX63 |
| 1301 | GH56 + CRX06 + CRX57 |
| 1302 | GH56 + CRX06 + CRX56 |
| 1303 | GH56 + CRX62 + CRX61 + CRX56 |
| 1401 | GH56 + CRX23 + CRX57 |
| 1402 | GH56 + CRX04 + CRX56 |
| DR "PEV" | GH56 + CRX35 + CRX56 |
| 0701 | CRX49 + GH54 + CRX56 |
| 0801 | GH102 + CRX61 + CRX35 + CRX56 |
| 0802 | GH102 + CRX35 + CRX56 |
| 0803 | GH102 + CRX61 + CRX63 + CRX56 |
| 0901 | GH111 + GH54 + CRX56 |
| 1001 | CRX34 + CRX56 |
| DR "LY10" | GH102 + CRX23 + CRX57 |

The horseradish peroxidase-conjugated SSOs of the invention, called "HRP-SSOs," allow detection methods that employ chromogenic or chemiluminescent substrates that are easy to use and produce detectable signals rapidly (typically 1 to 10 minutes). The HRP-SSOs are stable for over two years without detectable loss of activity when stored at 4° C. See the article entitled "Nonisotopically labeled probes and primers" by Levenson and Chang, 1989, in *PCR Protocols: A Guide to Methods and Applications* (Innis, Gelfand, Sninsky and White ed., Academic Press, Inc. San Diego). Radiolabelled probes can be employed but are not necessary for excellent sensitivity, an important benefit provided by the present invention.

The dot-blot format for detection enables the rapid typing of a large number of samples and will be useful in determining the allele frequencies of HLA DRB. A recently developed alternative for PCR/SSO DRbeta typing is the immobilized reverse dot-blot format. See the article entitled "Genetic analysis of amplified DNA with immobilized sequence-specific oligonucleotide probes" by Saiki et al., 1989, *Proc. Natl. Acad. Sci. USA* 86:6230, and copending Ser. No. 347,495, filed May 4, 1989, incorporated herein by reference. In this procedure, the SSO probes are applied and fixed to the filter (rather than the amplified DNA applied and fixed to the filter), hence the term "reverse dot blot."

The reverse dot blot procedure allows a single sample to be analyzed in a single hybridization with a membrane containing an array of immobilized probes. The conventional dot blot format is useful when the number of samples exceeds the number of probes used (e.g., patient versus control or population genetics studies). The reverse dot blot format is valuable for clinical, diagnostic, and forensic analyses. The reverse dot blot format is described in more detail in Example 8.

The following examples show illustrative preferred embodiments of the present invention. The examples show that the present invention provides, in a preferred embodiment, a nonisotopic PCR/SSO system for HLA DRB typing that is simple, rapid, and capable of precise DRB typing for a variety of samples from different sources.

EXAMPLE 1

Amplification and Detection Methods

For typing samples with the first panel (Table 4) of probes, 0.5 μg of human genomic DNA was amplified using reaction constituents as described in the article entitled "Primer-directed enzymatic amplification of DNA with a thermostable DNA polymerase," by Saiki et al., 1988, *Science* 239:487 and in Scharf et al., 1988, *Hum. Immunol.* 22:61, and Scharf et al., 1989, *Proc. Natl. Acad. Sci. USA* 86:6215, incorporated herein by reference.

The HLA DRB generic PCR primers are GH46 (SEQ ID NO: 67) and GH50 (SEQ ID NO: 68). The sequences of these primers are shown below.

GH46 SEQ ID NO: 67   5'-CCGGATCCTTCGTGTCCCCACAGCACG
GH50 SEQ ID NO: 68   5'-CTCCCCAACCCCGTAGTTGTGTCTGCA

The primers were present in the reaction mixture at 500 nM. These primers produce a 272 base-pair (bp) fragment and contain sequences for BamHI and PstI restriction sites for cloning the PCR product. Digestion of the amplified DNA with BamHI and PstI produces a 248 bp product due to an internal PstI site.

The DRB1 alleles from all haplotypes (except DR2, DR7, and DR9) were specifically amplified by the PCR primers GH46 (SEQ ID NO: 67) and CRX37 (SEQ ID NO: 73). The sequence of the CRX37 (SEQ ID NO: 73) primer is shown below.

CRX37 (SEQ ID NO: 73 5'-GAATTCCCGCGCCGCGCT

Amplification with the GH46/CRX37 (SEQ ID NO: 67/SEQ ID NO: 73) primer pair produces a 297 bp fragment. Primer CRX37 (SEQ ID NO: 73) incorporates an EcoRI restriction endonuclease recognition sequence at the 5'-end to facilitate cloning and, in contrast to the primer pair GH46/GH50 (SEQ ID NO: 67/SEQ ID NO: 68), amplification and BamHI/EcoRI digestion with this primer pair allows isolation and analysis of the full-length PCR product.

Such isolation and analysis frequently involved the determination of the nucleotide sequence of the PCR product. For sequencing the HLA DRB alleles, 1 μg of purified human genomic DNA was amplified using the primer pairs GH46/GH50 (SEQ ID NO: 67/SEQ ID NO: 68) and GH46/CRX37 (SEQ ID NO: 67/SEQ ID NO: 73). The amplified DNA was cloned into M13mp10 by the methods described in Scharf et al., 1988, *Hum. Immunol.* 22:61, and Scharf et al., 1986, *Hum. Immunol.* 233:1076, incorporated herein by reference. The inserts were then sequenced by the dideoxy chain-termination procedure described in Sanger et al., 1977, *Proc. Natl. Acad. Sci. USA*. 74:5463 (see also U.S. patent application Ser. No. 249,367, filed Sep. 23, 1988, and incorporated herein by reference).

The sequences shown in Tables 1 and 2 above were generated by genomic cloning (see Horn et al., 1988, *Hum. Immunol.* 21: 249, incorporated herein by reference), PCR amplification (see Erlich et al., 1989, in *Immunobiology of HLA* (du Pont ed., Springer-Verlag, New York) and Scharf et al., 1989, *Proc. Natl. Acad. Sci. USA* 86: 6215, incorporated herein by reference), or from the literature (see WHO Nomenclature Committee, 1990, *Immunogenetics* 31:131 and Gregersen et al., 1989, "First domain diversity of DR and DQ subregion alleles" in *Immunobiology of HLA* (du Pont, ed., Springer-Verlag. New York)).

Samples were amplified for 32 cycles (unless otherwise noted) using the reaction conditions described above, except that 1.25 units (rather than 2.5 units) of Taq polymerase (PECI, Norwalk, Conn.) were added per 100 µl of reaction volume. The cDNAs for the bladder carcinoma patients were amplified for the HLA-DRB loci as described (see Kawasaki, 1989, "Amplification of RNA" in *PCR Protocols: A Guide to Methods and Applications* (Innis et al., eds., Academic Press. San Diego)). All samples were overlaid with 100 µl of high grade mineral oil (Sigma, St. Louis, Mo.) to prevent evaporation. After amplification, the oil overlay was extracted with 100 µl chloroform.

The thermal profile for each cycle comprised incubations at the following temperatures for the indicated times: 45 seconds at 94° C. (for denaturation of the DNA strands), 45 seconds at 55° C. (for annealing of the primers), and 45 seconds at 72° C. (for extension of the primed templates). After the last cycle, the PECI Thermal Cycler (Perkin Elmer Cetus Instruments, Norwalk, Conn.) was programmed to incubate the samples at 72° C. for 10 minutes to ensure that the final extension was complete. Care should be taken to avoid cross-contamination of samples; one must particularly guard against allowing the product of one PCR to contaminate an unamplified sample. U.S. patent application Ser. No. 557,517, filed Jul. 24, 1990, and the CIP of that application filed Nov. 2, 1990, both incorporated herein by reference, describe preferred methods to prevent amplification of PCR product that has been "carried over" to an unamplified sample.

After amplification, a small portion of the amplified DNA was denatured and applied to and crosslinked to a series of nylon filters; each filter was then hybridized to one of the labelled probes. Each SSO probe was covalently conjugated to horseradish peroxidase (HRP) and provides a means of nonisotopic detection in the presence of a chromogenic or chemiluminescent substrate. The nucleotide sequence, the encoded amino acids (or potential epitope), and the identified DR type, as well as the wash conditions for each probe are listed in Tables 4 and 5.

Thus, 5 µl of each amplified DNA sample were mixed with 100 µl of a mixture composed of 0.4M NaOH and 25 mM EDTA, and the resulting mixture applied to BioDyne B nylon filters (Pall Corp., Glen Cove, N.Y.) using a dot-blot manifold (Bio Rad, Richmond, Calif.). The filters, still in the dot-blot manifold, were rinsed with a mixture of 10 mM Tris-HCl and 0.1 mM EDTA, at pH 8.0, and dried on Whatman 3MM paper. The DNA was immobilized on the nylon filter by ultraviolet irradiation at a flux of 55 mJ/cm$^2$ with a Stratalinker™ (Stratagene, La Jolla, Calif.) UV light box.

Unless otherwise noted, all filters were hybridized in 2× SSPE (saline sodium phosphate EDTA), 5× Denhardt's solution, and 0.5% SDS with 2 pmoles of HRP-SSO probe per ml of hybridization solution for 15 min. at 42° C.

Horseradish peroxidase conjugated oligonucleotides were prepared as described by Levenson and Chang, 1989, in *PCR Protocols: A Guide to Methods and Applications* (Innis et al., eds., Academic Press, Inc. San Diego) and Saiki et al., 1988, *N. Eng. J. Med.* 319:537. Filters for each probe were washed in 25 ml of the SSPE solutions at the temperatures listed in Tables 4 and 5 for 15 minutes (unless noted otherwise).

After washing, filters to be developed with a chromogenic dye substrate were rinsed in PBS at room temperature for 30 minutes, then placed in 100 mM sodium citrate, pH 5.0, containing 0.1 mg/ml of 3,3',5,5'-tetramethylbenzidine (TMB) per milliliter (Fluka) and 0.0015 percent hydrogen peroxide, and incubated with gentle agitation for 5 to 15 minutes at room temperature. Developed filters were rinsed in PBS and immediately photographed. Filters that were developed with the chemiluminescent detection system (ECL; Amersham, Arlington Heights, Ill.) were rinsed in PBS for 5 minutes and placed in the ECL solution for 1 minute with gentle agitation. Filters were then exposed to X-ray film at room temperature for 1 to 5 minutes.

EXAMPLE 2

DRB1 Specific Amplification

Several polymorphic sequences of alleles of the DRB1 locus that distinguish the various DRB1 alleles are also present on alleles of the other DRB loci (see Table III). An example is the nucleotide sequence encoding the epitope "K-GR" (codons 71 to 74) on DR3 DRB1 alleles, where a probe to this region (CRX50) [SEQ ID NO: 75] can distinguish DR3 from DRw11 and DRw6 alleles. However, this epitope is also encoded by the DRB3 allele DRw52a (DRB3*0101) and is present on some DRw6 haplotypes and some DR3 haplotypes as well. Because the PCR primers GH46/GH50 (SEQ ID NO: 67/SEQ ID NO: 68) amplify all of the DRB loci, a DRw6 sample that was DRw52a at the DRB3 locus would be impossible to distinguish from a DR3 sample using this probe.

The present invention solves this problem by providing PCR primers that specifically amplify only the DRB1 locus. One of these primers hybridizes to a region in the intron immediately downstream from the second exon. The intron contains sequences that distinguish the DRB1 and DRB3 loci. The primer (CRX37) [SEQ ID NO: 73] hybridizes specifically to the DRB1 intron sequences, and combining this primer with GH46 [SEQ ID NO: 67] permits DRB1 specific amplification for most haplotypes.

To determine if the DRB1 locus is the only locus amplified with these putative DRB1 specific primers, DR2, DR3, and DR4 HTC (homozygous typing cells) DNA was amplified and analyzed with these primers and SSO probes for all the DRB loci. In addition to the DRB1 locus, the DR2 haplotype has a DRB2 and DRB5 locus, the DR3 haplotype has a DRB3 locus, and the DR4 haplotype has a DRB4 locus. The results are shown in FIG. 1.

To generate these results, about 200 ng of HTC DNA were amplified by the generic DRB primers GH46/GH50 (SEQ ID NO: 67/SEQ ID NO: 68) or by the DRB1 specific primers GH46/CRX37 (SEQ ID NO: 67/SEQ ID NO: 73) and applied to filters as described in Example 1. Each filter containing amplified cell line DNA (samples 1 to 4) was hybridized with the probes shown in FIG. 1. The locus to which each probe hybridizes is shown in parentheses. CRX36 (SEQ ID NO: 72) hybridizes to the DRB4 locus of DR4, DR7, and DR9. CRX22 (SEQ ID NO: 65) hybridizes to the DRB3 allele DRw52b.

The sequence of the SSOs:

| CRX36 | SEQ ID NO: 72 | 5'-CCCGCCTCCGCTCCA |
|---|---|---|
| CRX22 | SEQ ID NO: 65 | 5'-GAGCTGCTTAAGTCT | is described by Schaff et al., 1989, *Proc. Natl. Acad. Sci. USA* 86:6215, incorporated herein by reference. Probe GH91 (SEQ ID NO: 88, 5'-CTCCCGTTTATGGATGTAT) hybridizes specifically to the DRB2 locus. This probe was hybridized as described in Example 1 and washed in 1× SSPE, 0.1% SDS for 15 minutes at 42° C. The samples amplified are: (1) No DNA (negative control); (2) DR2 HTC "SCHU"; (3) DR3 HTC "QBL"; and (4) DR4 HTC "BSM." After the hybridization and wash steps, the probes were detected by enhanced chemiluminescence.

FIG. 1 shows that all of the DRB loci for all three HTCs are amplified with the generic DRB primers, while the DRB1 specific primers only amplify the DRB1 loci from the DR3 and DR4 HTCs. Interestingly, for the DR2 HTC, the DRB2 locus is amplified, albeit weakly, with the DRB1 specific primers. The DRB1 specific primers amplify DRB1 sequences efficiently from all DR haplotypes tested except DR2, DR7, and DR9, as shown in FIGS. 1 and 2. To generate the results shown in FIG. 2, about 0.5 μg of genomic DNA from HTCs was amplified for HLA DRB with the DRB1 specific primers GH46/CRX37 (SEQ ID NO: 67/SEQ ID NO: 73). Amplification reactions and filters were prepared as described in Example 1. Each filter strip was hybridized to one of the probes shown under the appropriate conditions of hybridization and wash stringency (see Tables 4, 5, and 7). After the hybridization and wash steps, filters were developed in the chromogenic substrate TMB. The samples are: (1) DR1 HTC "KAS9003"; (2) DR2 HTC "SCHU"; (3) DR3 HTC "QBL"; (4) DR4 HTC "BSM"; (5) DR5 (DRw11) HTC "SPO010"; (6) DRw6 HTC "OMW"; (7) DR7 HTC "MOU"; (8) DRw8 HTC "SPACH"; (9) DR9 HTC "DKB"; and (10) DRw10 HTC "SHY".

The results in FIG. 2 indicate that the DR7 probe CRX49 (SEQ ID NO: 74) ("G-YK") does hybridize to the weakly amplified DR7 HTC in this experiment. DRB1 amplification of DR7 from heterozygous samples is typically weak. These results demonstrate that the generic and DRB1 specific primers can be used for complete DRB1 typing.

EXAMPLE 3

Typing for the Serological DR Types 1 Through 10

About 0.5 μg of genomic DNA from HTCs was amplified for HLA DRB. All samples except for nos. 3 and 6 were amplified with the generic primers GH46/GH50 (SEQ ID NO: 67/SEQ ID NO: 68). Sample nos. 3 and 6 were amplified with the DRB1 specific primers GH46/CRX37 (SEQ ID NO: 67/SEQ ID NO: 73). Amplification reactions and filters were prepared as described in Example 1. Each filter strip was hybridized to one of the probes shown under the appropriate conditions of hybridization and wash stringency (see Tables 4, 5, and 7). After probing and washing, filters were developed in the chromogenic substrate TMB. The samples are: (1) DR1 HTC "KAS9003"; (2) DR2 HTC "SCHU"; (3) DR3 HTC "QBL"; (4) DR4 HTC "BSM"; (5) DR5 (DRw11) HTC "SPO010"; (6) DRw6 HTC "OMW"; (7) DR7 HTC "MOU"; (8) DRw8 HTC "SPACH"; (9) DR9 HTC "DKB"; and (10) DRw10 HTC "SHY".

Figure 3:
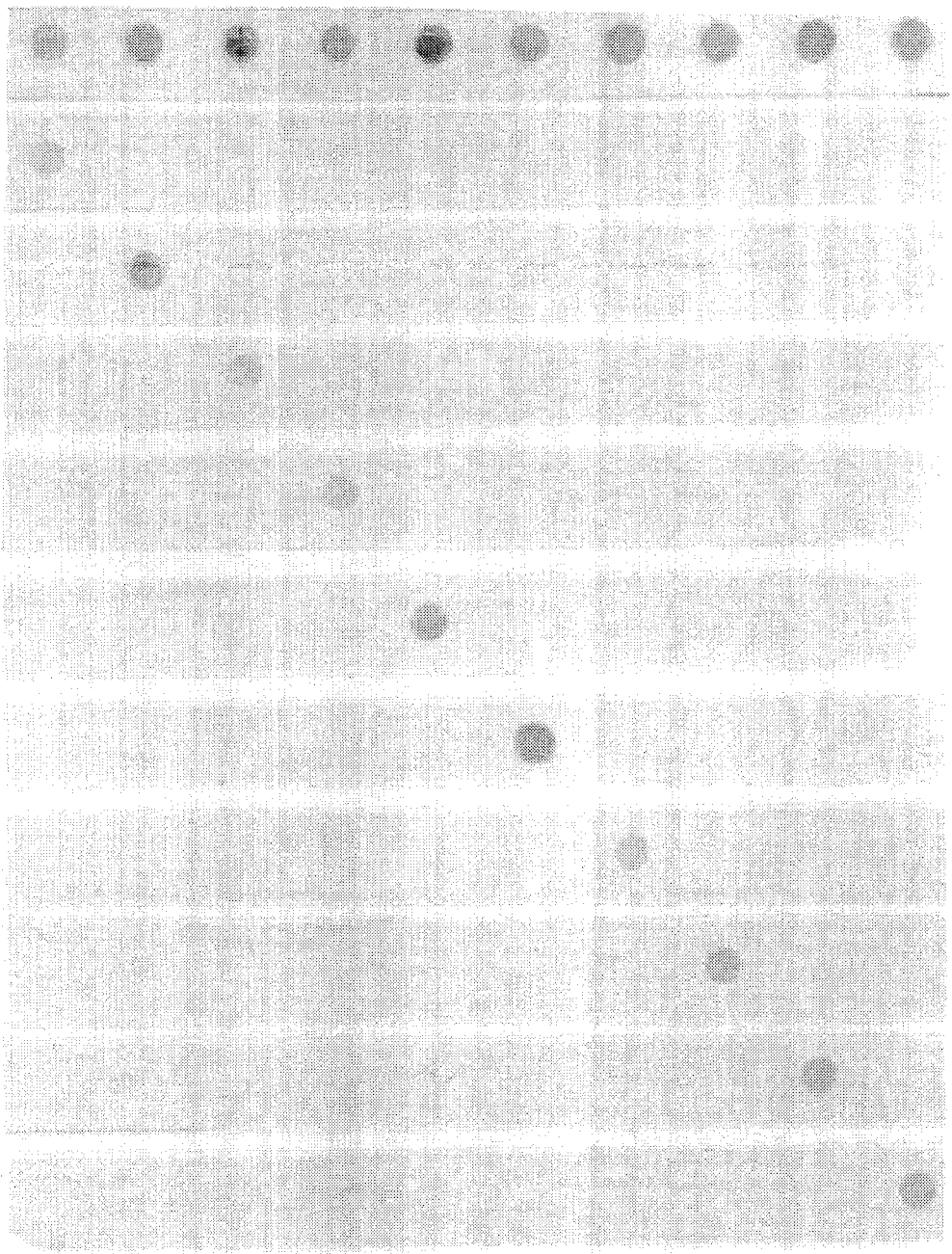
FIG. 3 shows the results of HLA DRB DNA typing of the classical serological types DR1 through DR10; see Example 3.

FIG. 3 demonstrates the results of DR typing for the classical, serologically defined DR types 1 through 10 on a panel of HTCs. A single probe can be used to detect each of the classical DR types, but two different PCR primer pairs were required. For all but the DR3 and DRw6 samples, the generic PCR primers GH46/GH50 (SEQ ID NO: 67/SEQ ID NO: 68) can be used. The DRB1 specific primer pair GH46/CRX37 (SEQ ID NO: 67/SEQ ID NO: 73) was used for amplifying the DNA of the DR3 and DRw6 samples in this array, because the probe used to detect the "Y" epitope (GH125 [SEQ ID NO: 94]; codon 26) on the DR3 HTC "QBL" (DRw17) is also present on the DRB3 allele (DRw52a) of the DRw6 sample. If the standard DRB primers had been used, then the "Y" probe would have hybridized to the DRw6 sample as well.

EXAMPLE 4

General DRB1 Typing Strategy

For typing a particular sample, the generic primers should be used for the first amplification, followed by probing of the amplified DNA with the first panel of probes (Tables 4 and 7). This panel of probes will identify the majority of the serological types; although GH56 (SEQ ID NO: 86) ("YSTS") will not unequivocally distinguish DR3 from DRw6.

For samples that are positive with GH56 (SEQ ID NO: 86), or for subtyping particular DR types (e.g., the Dw types of DR4 or the subtypes of DRw8), the second panel (Table 5) of probes should be used. As discussed above, some of the probes in the second panel require amplification with the DRB1 specific pair of PCR primers. By combining the results of the probings from the first and second panels, one can distinguish 31 of the 34 DRB1 alleles in the 1989 allele set. The combinations of SSO probes used to identify these alleles is shown in Table 8. The DR2 subtypes (DRB1*1501, *1502, *1601, and *1602) are not distinguished by these primers and probes, and the DRB1*0403 and DRB1*0406 alleles are not distinguished by these probes.

One DR2 probe of the invention comprises sequences that hybridize to the first hypervariable region ("Q-D-Y") of the DRB5 locus. Because the DRB5 locus is present on all known DR2 haplotypes and only on those haplotypes, such a probe can be used reliably to type for DR2 in an amplification with generic DRB primers. Probe GH104 (SEQ ID NO: 90) ("W-P-R") hybridizes to the first hypervariable region of the DR2 DRB1 locus and hybridizes specifically to DR2 DNA when amplified with the generic primers (FIG. 1) but not with the DRB1 specific primers. These two probes are identical indicators of DR2 in an amplification with generic primers.

EXAMPLE 5

Subtyping DR4

The subtyping of the DR4 specificity cannot be carried out serologically. The subtypes have been revealed by two dimensional protein gel electrophoresis and cellular typing; both methods are cumbersome and time-consuming. Dw4, Dw 10, Dw 13, and Dw14 differ from each other at positions 70 to 74 of the third hypervariable region of the gene. Dw15 also has a serine ("S") at position 57. Dw13 also has the same arginine residue at position 71 as Dw14 and Dw15 but is distinguished by a glutamic acid ("E") as position 74.

As a result, the SSO probe CRX04 (SEQ ID NO: 60) ("R") probe hybridizes to the Dw13, Dw14, and Dw15 alleles; these alleles have to be distinguished from each other by additional probes. The SSO probe CRX15 (SEQ ID NO: 64) ("R-E") specifically distinguishes Dw13 from Dw14 and Dw15, and CRX61 (SEQ ID NO: 80) ("S") specifically distinguishes Dw15 from Dw14. The "G" versus "V" polymorphism at position 86 that distinguishes various DRB1 alleles (e.g., Dw14.1 or DRB1*0404 from Dw14.2 or DRB1*0408) is detected using the CRX56 (SEQ ID NO: 77) probe ("G") and the CRX57 (SEQ ID NO: 78) probe ("V") (see Table 5).

HTCs with DR types 1 through 10 and the five DR4 Dw subtypes were amplified with the DRB1 specific primers GH46/CRX37 (SEQ ID NO: 67/SEQ ID NO: 73), applied to six identical nylon filters, and hybridized with HRP-SSO's specific for the Dw type. The results are shown in FIG. 4.

Figure 4:
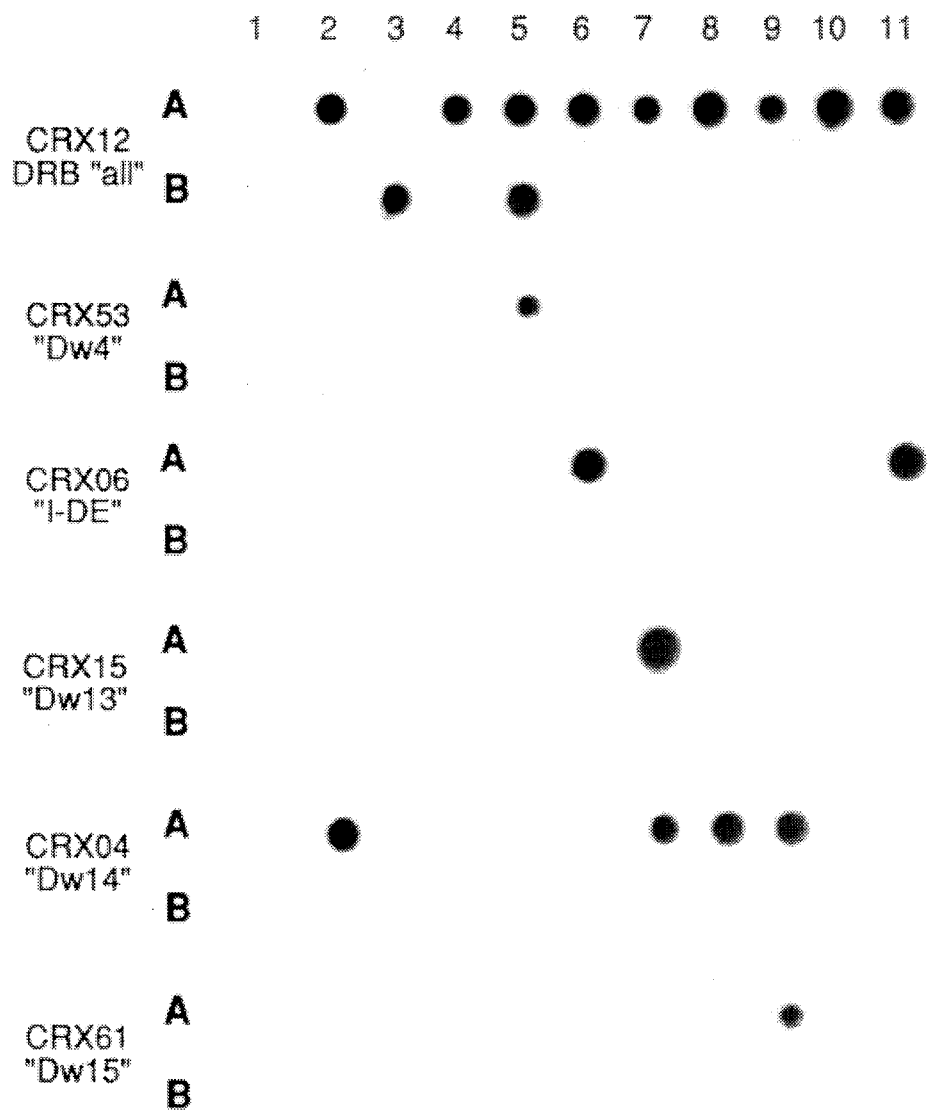
FIG. 4 shows the results of HLA DRB DNA typing to subtype cell lines with the DR4 serological specificity; see Example 5.

To generate the results shown in FIG. 4, about 500 ng of HTC genomic DNA were amplified with the DRB1 specific primers GH46/CRX37 (SEQ ID NO: 67/SEQ ID NO: 73). Each pair of filters, A and B, were hybridized with the probes shown in FIG. 4. The samples are: Row A: (1) No DNA control; (2) DR1 HTC "KAS9003"; (3) DR2 HTC "SCHU"; (4) DR3 HTC "QBL"; (5) DR4 Dw4 HTC "BSM"; (6) DR4 Dw10 HTC "YAR"; (7) DR4 Dw13 HTC "JHA"; (8) DR4 Dw14 HTC "BM92"; (9) DR4 Dw15 HTC "LKT3"; (10) DR5 HTC "SPOO10"; and (11) DRw6 HTC "OMW"; Row B: (1) No DNA control; (2) DR7 HTC "MOU"; (3) DRw8 HTC "SPACH"; (4) DR9 HTC "DKB"; and (5) DRw10 HTC "SHY".

After the hybridization and wash steps, the probes were detected by enhanced chemiluminescence. Panel A shows that all but the DR2, DR7, and DRw9 HTCs hybridized to CRX12 (SEQ ID NO: 63).

Panel B shows that CRX53 (SEQ ID NO: 76) hybridizes specifically to the Dw4 HTC BSM. An alternative probe for typing DR4 Dw4 is DRB163 (SEQ ID NO: 239), using the hybridization and wash conditions given in Example 9. Another alternative probe for typing DR4 Dw4 that gives a much stronger signal at lower stringencies (2× SSPE, 5× Denhardt's, 0.5% SDS at 42° C. for 15 minutes hybridization and 2× SSPE, 0.1% SDS at 42° C. for 15 minutes wash) is probe CRX64 (SEQ ID NO: 83), shown below.

CRX64 SEQ ID NO: 83 5'-HRP-GAGGAIAAGCIGGCC-3'

HRP is horseradish peroxidase. I is inosine, which slightly destabilizes the probe.

Panel C shows detection of the Dw10 HTC "YAR" with the SSO CRX06 (SEQ ID NO: 61) ("I-DE"). This probe also hybridizes to the HTC "OMW", which is DRw13, and shares this polymorphism.

Panel D shows specific hybridization of CRX15 (SEQ ID NO: 64), which distinguishes the Dw13 sample, JHA, from the Dw14 sample BM92 and the Dw15 sample LKT3.

Panel E shows hybridization of CRX04 (SEQ ID NO: 60) to JHA, BM92, and LKT3, which are Dw13, Dw14, and Dw15, respectively. CRX04 (SEQ ID NO: 60) also hybridizes to the DR1 HTC KAS9003, which is DRB1*0101, and shares this polymorphism ("R") with these three Dw-types. The DR4 Dw14 type is inferred from the probe hybridization pattern in which samples do not hybridize to either CRX15 (SEQ ID NO: 64) ("R-E") or CRX61 (SEQ ID NO: 84) ("S"; panel F), but do hybridize to CRX04 (SEQ ID NO: 60) ("R"). Panel F shows hybridization of CRX61 to the Dw15 HTC "LKT3".

FIG. 4 shows that, in general, the present invention enables one to distinguish samples that share polymorphic regions recognized by these probes by the pattern of hybridization to the first panel of probes. For example, DR4 Dw types which are positive for the "R" epitope can be distinguished from DR1 by being positive for GH59 (SEQ ID NO: 87) ("V-H") and negative for CRX60 (SEQ ID NO: 79) ("W-L-F"); DR4 Dw10 can be distinguished from DRw13 by being positive for GH59 (SEQ ID NO: 87) and negative for GH56 (SEQ ID NO: 86) ("YSTS").

Table 8 shows that the two DR4 subtypes that this system is not capable of distinguishing are the DRB1*0403 and DRB1*0406 alleles. These two alleles will give the same pattern of hybridization with the two panels of probes. DRB1*0406 is identical to DRB1*0403, except for a serine residue at position 37, where DRB1*0403 has a tyrosine residue. The illustrative panels of probes shown above are not capable of detecting this polymorphism, but the use of additional probes provides complete discrimination.

EXAMPLE 6

Subtyping DR3, DR5, DRw6, and DRw8

The subtypes for the "splits" of DR3, DR5, DRw6, and DRw8 can be identified by using probes that distinguish between the various alleles of each haplotype. For example, both DRw17 and DRw18 hybridize to the "K-GR" probe CRX50 (SEQ ID NO: 75), but only DRw17 hybridizes to the "Y" probe GH125 (SEQ ID NO: 94), which distinguishes DRw17 from DRw18. Likewise, the DRw11 and the DRw12 alleles (which used to be grouped as DR5) can be distinguished from each other and from the three DRw8 alleles by using a different combination of probes.

DNA amplified with the DRB1 specific PCR primers CRX37/GH46 (SEQ ID NO: 73/SEQ ID NO: 67) from HTCs of the "general" serological DR types 1 through 10 along with HTCs of the DR3, DR5, DRw6, DRw8 subtypes, was applied to 12 filters. Because the serological DR types of these samples were already known, only the probes necessary to determine the subtypes of these alleles were used to illustrate this aspect of the invention. The results are shown in FIG. 5.

Figure 5:
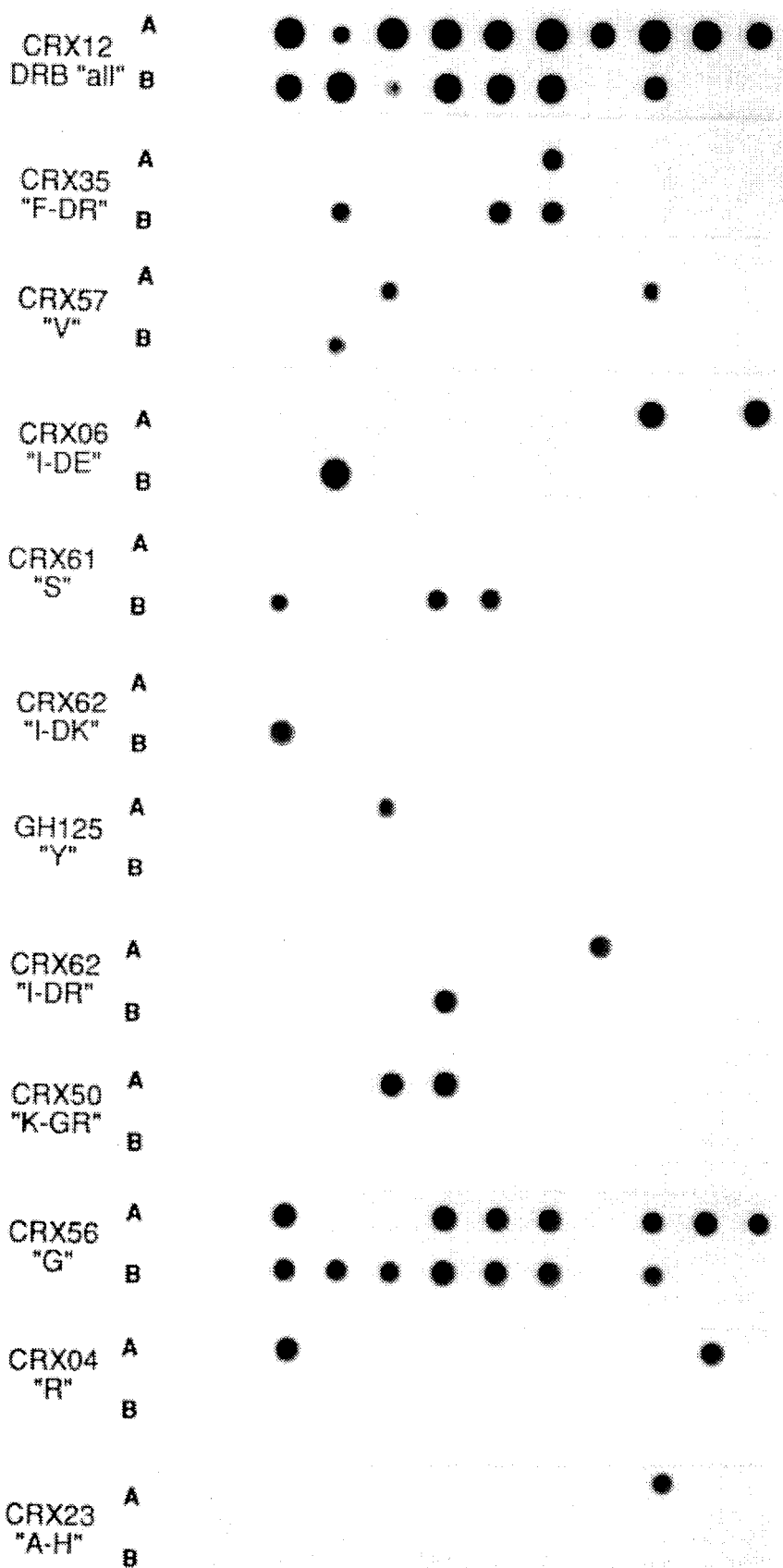
FIG. 5 shows the results of HLA DRB DNA typing to subtype the DR3, DR5, DRw6, and DRw8 specificities; see Example 6.
Figure 7:
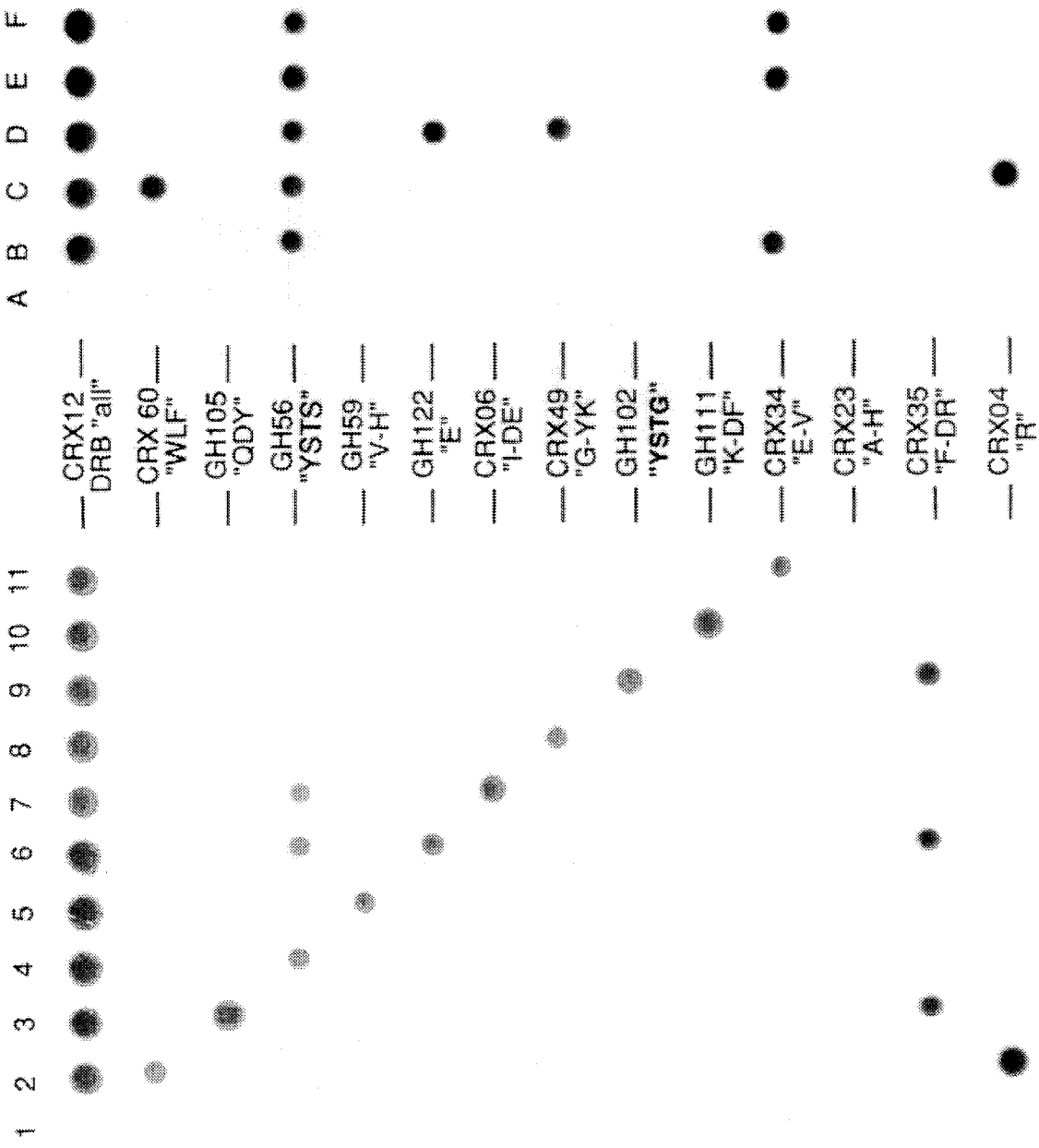
FIG. 7 shows the results of HLA DRB DNA typing of a number of different cell lines; see Examples 6 and 7.

To generate the results shown in FIG. 5, about 500 ng of HTC genomic DNA were amplified with the DRB1 specific primers GH46/CRX37 (SEQ ID NO: 67/SEQ ID NO: 73). Each pair of filters, A and B, was hybridized with the probes shown. The samples are: Row A: (1) No DNA control; (2) DR1 HTC "KAS9003"; (3) DR2 HTC "SCHU"; (4) DRw17 HTC "QBL"; (5) DRw18 HTC "RSH"; (6) DR4 HTC "BSM"; (7) DRw11 HTC"SPOO10"; (8) DRw12 HTC "HERLUF"; (9) DRw13/DRw14 "KOSE"; (10) DRw14 HTC "AMALA"; (11) DRw13 HTC "SLE"; Row B: (1) No DNA control; (2) DRw13 HTC "HAG"; (3) DR PEV "BAR P"; (4) DR7 HTC "MOU"; (5) DRw8.3 HTC "TAB"; (6) DRw8.1 HTC "ARC"; (7) DRw8.2 HTC "SPL"; (8) DR9 HTC "DKB"; and (9) DRw10 HTC "SHY". The data for the first panel of probes, which shows that GH56 (SEQ ID NO: 86) ("YSTS") hybridizes to DR3, DR5, and DRw6, and GH102 (SEQ ID NO: 89) ("YSTG") hybridizes to DRw8 is shown in FIG. 7 (see Example 7).

After the hybridization and wash steps, the bound probes were detected by enhanced chemiluminescence. By determining the pattern of probes that hybridize to each sample (see Table 8), the samples can be subtyped for specific alleles, as shown in FIG. 6. In FIG. 6, samples which hybridized to probes are shown with a "+" symbol. Blank cells indicate samples which did not hybridize to a particular probe. Except for "KOSE and BAR P", all the samples were homozygous typing cells.

The hybridization data and DR types for the DR3, DR5, DRw6 and DRw8 samples are shown in FIG. 6. The sample "KOSE" was typed serologically as homozygous for the DRw6 haplotype (though this sample has been shown to be Dw9 and Dw19); however, it types as DRB1*1302 (CRX06+CRX56 [SEQ ID NO: 61+SEQ ID NO: 77]) and DRB1*1401 (CRX23+CRX57 [SEQ ID NO: 66+SEQ ID NO:78]).

The sample "BAR P" is typed by serology and MLC as DR4 Dw10 and DRw6. Consequently, "BAR P" hybridizes to the probes CRX35 (SEQ ID NO: 70) and CRX56 (SEQ ID NO: 77) ("F-DR" and "G"), which types it as the newly discovered "DR PEV" DRw6 allele, and to the probes CRX06 (SEQ ID NO: 61) and CRX57 (SEQ ID NO: 78) ("I-DE" and "V"), reflecting the presence of the DR4 Dw10 allele (DRB1*0402).

EXAMPLE 7

DR Typing of Cell Lines

Many established cell lines do not express the Class II molecules, making it impossible to DR type them serologically. DNA samples from five Class II negative cell lines coded as a blind panel were amplified with the generic primer pair GH46/GH50 (SEQ ID NO: 67/SEQ ID NO: 75) and probed with the first panel of probes (Table 4) to establish the general serological DR types for the samples (FIG. 7).

For DR typing these and other cell lines, approximately 100 ng of cell line DNA were amplified for 30 cycles with the generic HLA DRB primers GH46/GH50 (SEQ ID NO: 67/SEQ ID NO: 75). Each filter containing amplified cell line DNA (samples A through F) was hybridized simultaneously with a control filter (samples 1 through 11) containing HTC DNAs amplified with the generic HLA DRB primers. All filters were prepared as described in Example 1. The results are shown in FIG. 7. Each pair of filters was hybridized to the SSO probes shown. The samples are: (1) No DNA control; (2) DR1 HTC "KAS9003"; (3) DR2 HTC "SCHU"; (4) DR3 HTC "QBL"; (5) DR4 HTC "BSM"; (6) DR5 (DRw11) HTC "SPOO1O"; (7) DRw6 HTC "OMW"; (8) DR7 HTC "MOU"; (9) DRw8 HTC "SPACH"; (10) DR9 HTC "DKB"; (11) DRw10 HTC "SHY;" (A) No DNA control; (B) Raji; (C) 616; (D) Beguit; (E) RM3; and (F) RS225.

The signal intensity for the CRX12 (SEQ ID NO: 63) probe demonstrates that all of the samples were equally well amplified. Raji, RM3, and RS225 hybridize to the probe CRX34 (SEQ ID NO: 70) which is specific for DRw10. Sample 616 hybridizes to the probes CRX60 (SEQ ID NO: 79) ("WLF") and CRX04 (SEQ ID NO: 60) ("R"), which is consistent with this sample having the DR1 allele.

The cell line Beguit hybridizes to the DR7 probe CRX49 (SEQ ID NO: 74) ("G-YK") and to two other probes, GH56 (SEQ ID NO: 86) ("YSTS") and GH122 (SEQ ID NO: 93) ("E"), suggesting that it is DR7 and DRw11. However, the putative DRw11 allele from this sample would be expected to hybridize either to CRX35 (SEQ ID NO: 71) ("F-DR"; DRB1*1101) or CRX06 (SEQ ID NO: 61) ("I-DE"; DRB1*1102), but it does not, suggesting that it may be a new variant of DRw11, as discussed further below.

This sample, derived from an individual with bare lymphocyte syndrome, was cloned and sequenced to determine the nature of the polymorphism at this position. Sequencing of the allele showed that there is indeed a sequence polymorphism at the third hypervariable region that codes for the epitope "F-DE"; this allele types as DRB1*1103 (see sequence "Beguit" in Table 3). Probe CRX68 (SEQ ID NO: 84) hybridizes specifically to this polymorphism in the third hypervariable region (see Table 4).

All of the other samples also hybridize to the GH56 "YSTS" probe, so they could be DR3, DRw11, or DRw6. Because these other samples do not hybridize to the "E" probe, it is likely they are DR3 or DRw6. However, the samples do not hybridize to the probes CRX06 (SEQ ID NO: 61) ("I-DE") or CRX23 (SEQ ID NO: 66) ("A-H"), which recognize sequences present in three common DRw6 alleles, DRB1*1301, DRB1*1302, and DRB1*1401; this suggests that they are not DRw6, but DR3.

To confirm this, the samples were amplified with the DRB1 specific primers GH46/CRX37 (SEQ ID NO: 67/SEQ ID NO: 73) and probed with the SSOs for DR3, GH125 ("Y") and CRX50 (SEQ ID NO: 75) ("K-GR"). About 100 ng of cell line genomic DNA were amplified with the DRB1 specific primers GH46/CRX37 (SEQ ID NO: 67/SEQ ID NO: 73) as described in Example 1. Each filter containing amplified cell line DNA (samples A through F) was hybridized simultaneously with a control filter (samples 1 through 11) containing HTC DNAs amplified with the DRB1 specific primers. All filters were prepared as described in Example 1. The results are shown in FIG. 8.

Each pair of filters was hybridized the SSO probes shown. The samples are: (1) No DNA control; (2) DR1 HTC "KAS9003"; (3) DR2 HTC "SCHU"; (4) DR3 HTC "QBL"; (5) DR4 HTC "BSM"; (6) DR3 (DRw11) HTC "SPOO1O"; (7) DRw6 HTC "OMW"; (8) DR7 HTC "MOU"; (9) DRw8 HTC "SPACH"; (10) DR9 HTC "DKB"; (11) DRw10 HTC "SHY"; (A) No DNA control; (B) Raji; (C) 616; (D) Beguit; (E) RM3; and (F) RS225. After the hybridization and wash steps, the bound probes were detected by enhanced chemiluminescence.

As FIG. 8 shows, Raji, 616, RM3, and RS225 hybridize to both the "Y" and "K-GR", which types them as DR3 (DRw17). In summary, Raji, RM3, and RS225 type as DRw10/DRw17. RM3 and RS225 are cell lines derived from Raji, so it is not surprising that they have the same DRB type. Cell line 616 types as DR1/DRw17, and Beguit types as DR7/DRw11 but, as noted above, the Beguit cell line contains the DRB1*1103 allele, which has the "F-DE" epitope. Previously, most DRw11 typing cells were observed to contain DRB1 alleles with the "F-DR" epitope. Thus, the Beguit cell line contains an unusual DRB1 allele for the DRw11 type.

In addition to cell line samples, DNA from three different sources was amplified and typed. One source is purified genomic DNA from a set of unrelated, heterozygous individuals from the Center for Study of Human Polymorphism (CEPH, Paris, France; samples 555 to 863). Another source was cDNA made from mRNA of cancer tissue from patients with bladder carcinoma (samples 2426, 2446, 2540, 2671, 2755). Normal human bladder cells do not express Class II molecules, but various carcinoma cells have been reported as expressing Class II molecules.

The remaining sample (PSW) is a buccal swab amplified for HLA DRB directly without DNA purification. For complete DR typing, the samples were amplified with both the generic DRB primers GH46/50 (SEQ ID NO: 67/SEQ ID NO: 75) and the DRB1 specific PCR primers GH46/CRX37 (SEQ ID NO: 67/SEQ ID NO: 73). Filter strips containing DNA samples amplified with the general probes were probed with the first panel of probes (Table 4), and filter strips containing DNA samples amplified specifically for DRB1 were probed with the second panel of probes (Table 5).

Comparing the pattern of hybridization with Table 3 and Table 8, one can unambiguously derive the DRB-type of the samples. The results for the typing of the heterozygous samples are shown in FIG. 9. In FIG. 9, samples which hybridized to a probe are shown with a "+" symbol. Blank cells indicate samples which did not hybridize to a particular probe.

Samples 555 to 863 are pure genomic DNA provided by CEPH. Sample "PSW" is a sample amplified directly from a buccal swab. This sample was heated for 5 minutes at 95° C. in 200 µl of 5% Chelex (Singer-Sam et al., 1989, *Amplifications* 3:11 ). About 50 µl of this solution were amplified directly in 200 µl of reaction volume, and generic DRB and DRB1 specific amplification reactions were conducted for the sample for 40 cycles.

Samples 2426, 2446, 2540, 2671, and 2755 were amplified from bladder carcinoma cDNA preparations. The bladder carcinoma samples 2426, 2446, 2540, 2671, and 2755 were not analyzed with the SSOs GH 125 (SEQ ID NO: 94), CRX50 (SEQ ID NO: 75), CRX56 (SEQ ID NO: 77), and GH54 (SEQ ID NO: 85), because these probes require amplification with the DRB1 specific primers GH46/CRX37 (SEQ ID NO: 67/SEQ ID NO: 73). Because CRX37 (SEQ ID NO: 73) is derived from intron sequence, it cannot be used to amplify cDNA. ND is not determined.

The buccal swab sample, PSW, is DR4 Dw14 (DRB1*0404) and DRw11.

These data show that the system is capable of typing heterozygous DNAs from a variety of sources, from standard purified genomic DNA, from cDNAs synthesized from RNA, and from unusual sources, such as a buccal swab or single hair.

EXAMPLE 8

DRB Typing—Reverse Dot Blot Format

In this embodiment of the invention, the DRB probes are fixed to a membrane, and the amplified target DNA is hybridized to the membrane-bound probe. The set of typing probes is designed so that each probe will hybridize to a specific target sequence at the same temperature and salt concentration (and stay hybridized under the same wash conditions) as all other probes in the set. The PCR primers used in the amplification are biotinylated, as described in the book *PCR Protocols*, incorporated herein by reference, so that any amplified DNA that hybridizes to the membrane-bound probes can be easily detected. In one embodiment, detection is carried out by reacting streptavidin (SA)-conjugated horseradish peroxidase with any biotinylated, amplified DNA hybridized to the membrane-bound probe. The HRP thus becomes bound, through the SA-biotin interaction, to the amplified DNA and can be used to generate a signal by a variety of well known means, such as the generation of a colored compound, e.g., by the oxidation of tetramethylbenzidine (see U.S. Pat. No. 4,789,630, incorporated herein by reference).

Although the probes can be fixed to the membrane by any means, a preferred method involves "tailing" an oligonucleotide probe about 13 to 25 nucleotides in length with a much longer sequence of poly-dT. The resulting poly-dT "tail" can then be reacted with amine groups on the membrane to fix the probe covalently to the membrane. This reaction can be facilitated by UV irradiation.

Terminal deoxyribonucleotidyl transferase (TdT, Ratlift Biochemicals; for the reactions below assume a concentration of abut 120 Units/µl, which is 100 pmol/µl) can be used to create a poly-dT tail on a probe, although one can also synthesize the tailed probe on a commercially available DNA synthesizer. When one uses a DNA synthesizer to make the tailed probe, however, one should place the tail on the 5' end of the probe, so that undesired premature chain termination occurs primarily in the tail region.

TdT reactions should be carried out in volume of about 100 µl containing 1× TdT salts, 200 pmol of oligonucleotide, 800 µM dTT, and 60 units of TdT. 10× TdT salts is 1,000 mM K-cacodylate, 10 mM $CoCl_2$, 2 mM dithiothreitol, 250 mM Tris-Cl, pH 7.6, and is prepared as described by Roychoudhury and Wu, *Meth. Enzymol.* 65:43–62, incorporated herein by reference. A 10× stock solution of 8 mM dTTP can be prepared (neutralized to pH 7 with NaOH) for convenience.

The TdT reaction should be carried out at 37° C. for two hours and then stopped by the addition of 100 µl of 10 mM EDTA, pH 8. The final concentration of tailed oligonucleotide is 1 µM (1 pmol/µl), and the length of the homopolymer tail is about 400 residues. Tail length can be changed by adjusting the molar ratio of dTTP to oligonucleotide. The tailed probes can be stored at −20° C. until use.

Two types of nylon membrane are preferred for the reverse dot blot format: Biodyne™ nylon membrane, 0.45 micron pore size, manufactured by Pall; and Biotrans™ nylon membrane, 0.45 micron pore size, manufactured by ICN. The probes can be spotted onto the membrane very conveniently with the Bio-Dot™ dot blot apparatus manufactured by BioRad. Each probe is spotted onto a unique, discrete location onto the membrane. About 5 to 10 picomoles of each tailed probe is premixed with 60–100 µl of TE buffer before application to the dot blot apparatus. After dot blotting, the membrane is briefly placed on absorbent paper to draw off excess liquid.

The membrane is then placed inside a UV light box, such as the Stratalinker™ light box manufactured by Stratagene, and exposed to 50 to 60 millijoules of flux to fix the tailed probe to the nylon membrane. After a brief rinse (for about 15 minutes in hybridization solution) to remove unbound probe, the membrane is then ready for hybridization with biotinylated PCR product. One-half to one picomole (one-quarter to one-half of a typical, 100 µl PCR mixture) of PCR product is added to each probe panel for hybridization. About 50 µl of streptavidin-horseradish peroxidase (SA-HRP, commercially available from PECI; see the instruction manual for the AmpliType™ DQα DNA Typing Kit, incorporated herein by reference) conjugate can be added at this time for convenience, but better signals will result if a separate SA-HRP incubation and wash, at room temperature, is performed after the stringency wash.

Hybridization is typically carried out at 50° C. for 30 minutes in a water bath and with hybridization buffer composed of 0.5% SDS and 3× to 5× SSPE, most commonly 4×. Stringency washing is carried out at 50° C. for 15 minutes in a water bath and with wash solution composed of 0.1% SDS and 1× SSPE. A post-wash of 1× PBS at room temperature for 30 minutes can enhance signal quality.

The biotinylated primers for the reverse dot blot method and other useful primers of the invention are shown below. Note, however, that one or both of the primers can be biotinylated in an amplification and that the primers can be used for amplification with any detection format.

| Primer | Seq. ID No. | Sequence |
| --- | --- | --- |
| CRX11 | SEQ ID NO: 62 | 5'-TCTAGAAGTACTCTACGTCT-3' |
| CRX28 | SEQ ID NO: 67 | B-CCGGATCCTTCGTGTCCCACAGCACG-3' |
| CRX29 | SEQ ID NO: 68 | B-CTCCCCAACCCCGTAGTTGTGTCTGCA-3' |
| DRB17 | SEQ ID NO: 73 | B-GAATTCCCGCGCCGCGCT-3' |
| DRB30 | SEQ ID NO: 107 | B-GAATTCCCGCGCCGCGCTCACCT-3' |
| DRB152 | SEQ ID NO: 228 | B-CCCCGTAGTTGTGTCTGCACACGG-3' |
| DB259 | SEQ ID NO: 95 | B-GAATTCCCGCGCCGCGCTCACCTCG-3' |
| DB260 | SEQ ID NO: 96 | B-GAATTCCCGCGCCGCGCTCACCTCGCC-3' |

B is biotin. CRX11 (SEQ ID NO: 62) is a left-end primer designed for use with GH50 (SEQ ID NO: 68) to amplify the DRB1 second exon of DR3, DR5, and DRw6 (13 and 14) haplotypes. CRX28 (SEQ ID NO: 67) is biotinylated left-end primer GH46 (SEQ ID NO: 67); CRX29 (SEQ ID NO: 68) is biotinylated right-end primer GH50 (SEQ ID NO: 68); and DRB17 (SEQ ID NO: 73) is biotinylated right-end primer CRX37 (SEQ ID NO: 73). DRB30 (SEQ ID NO: 107) is a right-end primer that includes the CRX37 (SEQ ID NO: 73) sequence and has the same DRB1 range as CRX37 (SEQ ID NO: 73) except that, unlike CRX37 (SEQ ID NO: 73), DRB30 (SEQ ID NO: 107) can amplify DR7 DRB1 sequences. DRB152 (SEQ ID NO: 228) is a group specific right-end primer for DR7 and DR9 alleles. DB259 (SEQ ID NO: 95) and DB260 (SEQ ID NO: 96) are also right-end primers designed to extend the range of DRB1 specific amplification to DR2 and DR9.

The hybridizing regions of the tailed probes for use in the reverse dot blot method are shown below. X is inosine. Where two probe names are shown, i.e., DRB01/CRX60 (SEQ ID NO: 79), the first name designates the hybridizing region (shown) of the tailed probe, the second designates the HRP-labeled, untailed probe.

| Primer | Seq. ID No. | | Sequence |
| --- | --- | --- | --- |
| CRX23 | SEQ ID NO: 66 | S | 5'-CCTGCTGCGGAGCACTG |
| GH54 | SEQ ID NO: 85 | U | 5'-GCTGTTCCAGGACTC |
| GH56 | SEQ ID NO: 86 | S | 5'-CAGACGTAGAGTACTCC |
| GH59 | SEQ ID NO: 87 | U | 5'-CATGTTTAACCTGCTCC |
| GH102 | SEQ ID NO: 89 | S | 5'-GAAATAACACTCACCCGTAG |
| GH104 | SEQ ID NO: 90 | S | 5'-TGACACTCCCTCTTAGGCT |
| GH105 | SEQ ID NO: 91 | U | 5'-CTTGCAGCAGGATAAGTATG |
| GH111 | SEQ ID NO: 92 | S | 5'-TTGAAGCAGGATAAGTTTGA |
| GH122 | SEQ ID NO: 93 | S | 5'-CAGTACTCCTCATCAGG |
| GH125 | SEQ ID NO: 94 | U | 5'-CTGTCCAGGTACCGCAC |
| DRB01/CRX60 | SEQ ID NO: 79 | S | 5'-CAAACTTAAGCTGCCAC |
| DRB02/CRX06 | SEQ ID NO: 61 | S | 5'-CATCCTGGAAGACGAGC |
| DRB03/CRX35 | SEQ ID NO: 71 | U | 5'-CCTGTCTTCCAGGAAGT |
| DRB04/CRX49 | SEQ ID NO: 74 | U | 5'-TGACACTTATACTTACC |
| DRB05/CRX34 | SEQ ID NO: 70 | U | 5'-CTCAAACTTAACCTCCTC |
| DRB06/CRX04 | SEQ ID NO: 60 | U | 5'-GAGCAGAGGCGGGCC |
| DRB07/CRX68 | SEQ ID NO: 84 | S | 5'-GACTTCCTGGAAGACGA |
| DRB08/CRX12 | SEQ ID NO: 63 | U | 5'-AGCTGGGGCGGCCT |
| DRB09/CRX50 | SEQ ID NO: 75 | U | 5'-CACCCGGCCCCGCTTCT |
| DRB10/CRX53 | SEQ ID NO: 76 | U | 5'-GAGCAGAAGCGGGCC |
| DRB11/CRX15 | SEQ ID NO: 64 | U | 5'-ACCTCGGCCCGCCTC |
| DRB12/CRX62 | SEQ ID NO: 81 | U | 5'-ACATCCTGGAAGACAAG |
| DRB13/CRX63 | SEQ ID NO: 82 | U | 5'-ACATCCTGGAAGACAGG |
| DRB14/CRX61 | SEQ ID NO: 80 | U | 5'-GCGGCCTAGCGCCGAGT |
| DRB15/CRX56 | SEQ ID NO: 77 | S | 5'-CGGGTTGGTGAGAGCT |
| DRB16/CRX57 | SEQ ID NO: 78 | S | 5'-CGGGTTGTGGAGAGCT |
| DRB19 | SEQ ID NO: 97 | S | 5'-TGACACTTATACTTACCGTC |
| DRB20 | SEQ ID NO: 98 | U | 5'-CTCAAACTTAACCTCCTCC |
| DRB21 | SEQ ID NO: 99 | S | 5'-GAGCAGAGGCGGGC |
| DRB22 | SEQ ID NO: 100 | U | 5'-GCCTGTCTTCCAGGAAGT |
| DRB23 | SEQ ID NO: 101 | U | 5'-GCCCGCTTCTGCTC |
| DRB24 | SEQ ID NO: 102 | U | 5'-GAGCAGAAGCXGGCC |
| DRB25 | SEQ ID NO. 103 | U | 5'-CATCCTGGAAGACAGG |
| DRB26 | SEQ ID NO: 104 | U | 5'-CATCCTGGAAGACAGGCGCG |
| DRB27 | SEQ ID NO: 105 | S | 5'-ACATCCTGGAAGACAAGC |
| DRB28 | SEQ ID NO: 106 | U | 5'-ACCTCGGCCCXCCTC |
| DRB31 | SEQ ID NO: 108 | S | 5'-CTCCCGTTTATGGATGTATC |
| DRB32 | SEQ ID NO: 109 | S | 5'-TGTCCAGGTACCGCA |
| DRB33 | SEQ ID NO: 110 | S | 5'-ACTCATGTTTAACCTGCTCC |
| DRB34 | SEQ ID NO: 111 | S | 5'-CTCATGTTTAACCTGCTCC |
| DRB35 | SEQ ID NO: 112 | S | 5'-TGTCGCCGAGTCCTGG |
| DRB36 | SEQ ID NO: 113 | S | 5'-CGCCTGTCTTCCAGGAAGT |
| DRB37 | SEQ ID NO: 114 | S | 5'-CCGCCTGTCTTCCAGGAAGT |
| DRB38 | SEQ ID NO: 115 | U | 5'-TCCACCCGGCCCCGCTTCT |
| DRB39 | SEQ ID NO: 116 | U | 5'-GAGCAGAAGCGGGC |
| DRB40 | SEQ ID NO: 117 | U | 5'-GAGXAGAAGCXGGCC |
| DRB41 | SEQ ID NO: 118 | U | 5'-GGCCCGCTTCTGCTC |
| DRB42 | SEQ ID NO: 119 | S | 5'-GACGGAGCTGGGGCGGCCT |

-continued

| Primer | Seq. ID No. | | Sequence |
|---|---|---|---|
| DRB43 | SEQ ID NO: 120 | U | 5'-GACTTCCTGGAGCGGAGG |
| DRB44 | SEQ ID NO: 121 | U | 5'-GACCTCCTGGAGCGGAGG |
| DRB45 | SEQ ID NO: 122 | S | 5'-GAGCGGAGGCGTGCC |
| DRB46 | SEQ ID NO: 123 | S | 5'-TCAGACGTAGAGTACTCC |
| DRB47 | SEQ ID NO: 124 | U | 5'-TCTTGCAGCAGGATAAGTATG |
| DRB48 | SEQ ID NO: 125 | S | 5'-CACTCATGTTTAACCTGCTCC |
| DRB49 | SEQ ID NO: 126 | U | 5'-TCAGACTTACGCAGCTCC |
| DRB50 | SEQ ID NO: 127 | U | 5'-TCAGACTTAAGCAGCTCC |
| DRB51 | SEQ ID NO: 128 | U | 5'-GAGCAGAGGCGGAGC |
| DRB52 | SEQ ID NO: 129 | U | 5'-GAGCAGAAGCGAGGCC |
| DRB53 | SEQ ID NO: 130 | U | 5'-GGCCCGCTTCTGCTCCA |
| DRB54 | SEQ ID NO: 131 | U | 5'-GCGGCCCGCTTCTGCTC |
| DRB55 | SEQ ID NO: 132 | U | 5'-GAGCAGAAGCGAGGC |
| DRB56 | SEQ ID NO: 133 | U | 5'-GGAGXAGAAGCXGGCCG |
| DRB57 | SEQ ID NO: 134 | U | 5'-CCACCCGGCCCGCTTCT |
| DRB58 | SEQ ID NO: 135 | U | 5'-CATCCTGGAAGACAGGCG |
| DRB59 | SEQ ID NO: 136 | U | 5'-CATCCTGGAAGACAGAGCG |
| DRB60 | SEQ ID NO: 137 | S | 5'-GGCGGCCTAGCGCCGAGT |
| DRB61 | SEQ ID NO: 138 | U | 5'-ACCTCCTGGAGCGGAGG |
| DRB62 | SEQ ID NO: 139 | S | 5'-GACTTCCTGGAGCGGAG |
| DRB63 | SEQ ID NO: 140 | S | 5'-CATCCTGGAGCAGGCG |
| DRB64 | SEQ ID NO: 141 | U | 5'-ACCTCGGCCCXCCTCTG |
| DRB66 | SEQ ID NO: 142 | U | 5'-GAGCAGAAGCGGG |
| DRB67 | SEQ ID NO: 143 | U | 5'-GAGXAGAAGCXGGCCG |
| DRB68 | SEQ ID NO: 144 | U | 5'-CCTCGGCCCXCCTCTGC |
| DRB69 | SEQ ID NO: 145 | U | 5'-CCTCCTGGAGCGGAGG |
| DRB70 | SEQ ID NO: 146 | U | 5'-CGCCTGTCTTCCAGGATG |
| DRB71 | SEQ ID NO: 147 | U | 5'-TTCTTGCAGCAGGATAAGTATG |
| DRB72 | SEQ ID NO: 148 | S | 5'-CGCCTGTCCTCCAGGATG |
| DRB73 | SEQ ID NO: 149 | U | 5'-AGAAGCGGGGCCGGGTG |
| DRB74 | SEQ ID NO: 150 | U | 5'-GAGCAGAGXCGGGCC |
| DRB75 | SEQ ID NO: 151 | U | 5'-GAGCAGAGAGCGGGC |
| DRB76 | SEQ ID NO: 152 | U | 5'-CTTCTGCTCCAGGAGG |
| DRB77 | SEQ ID NO: 153 | U | 5'-CTCCTGGAGCAGAAG |
| DRB78 | SEQ ID NO: 154 | U | 5'-CCTCCTGGAGCXGAAG |
| DRB79 | SEQ ID NO: 155 | U | 5'-CCTCCTGGAGCAAGAAG |
| DRB80 | SEQ ID NO: 156 | U | 5'-CGGCCCGCCTCTGCTC |
| DRB81 | SEQ ID NO: 157 | U | 5'-CGGGGCTGTGGAGAGCT |
| DRB82 | SEQ ID NO: 158 | U | 5'-CTTCTGCTCCAGGAGGTC |
| DRB83 | SEQ ID NO: 159 | U | 5'-ACCTCCTGGAGCAGAAG |
| DRB84 | SEQ ID NO: 160 | S | 5'-GGCCCGCCTCTGCTC |
| DRB85 | SEQ ID NO: 161 | U | 5'-GCCCGCCTCTGCTC |
| DRB86 | SEQ ID NO: 162 | U | 5'-GGCCCGCCTCTGC |
| DRB87 | SEQ ID NO: 163 | U | 5'-GAGGCGCGCCGAGGT |
| DRB88 | SEQ ID NO: 164 | U | 5'-GAGGCGCGCCGAGGTG |
| DRB89 | SEQ ID NO: 165 | U | 5'-GAGGCGCGCCGAGGTGGA |
| DRB90 | SEQ ID NO: 166 | S | 5'-AGAAGCGGGGCCGGGT |
| DRB91 | SEQ ID NO: 167 | S | 5'-AGAAGCGGGGCCGGG |
| DRB92 | SEQ ID NO: 168 | U | 5'-GGGGTTGGTGAGAGCT |
| DRB93 | SEQ ID NO: 169 | U | 5'-GGGGTTGTGGAGAGCT |
| DRB94 | SEQ ID NO: 170 | U | 5'-ACCTCGGCCCGCCTC |
| DRB95 | SEQ ID NO: 171 | S | 5'-CATCCTGGAAGACAGGC |
| DRB96 | SEQ ID NO: 172 | U | 5'-GAGCAGAAGCAGGCC |
| DRB97 | SEQ ID NO: 173 | U | 5'-GGCGGCCTAGCGCCGAGTAC |
| DRB98 | SEQ ID NO: 174 | U | 5'-TGTAGGACCTTCTGTCCG |
| DRB99 | SEQ ID NO: 175 | U | 5'-GTAGGACCTTCTGTCCG |
| DRB100 | SEQ ID NO: 176 | S | 5'-TTCTTGCAGCAGGATAAGTATGAG |
| DRB101 | SEQ ID NO: 177 | S | 5'-CTCCCGTTTATGGATGTATC |
| DRB102 | SEQ ID NO: 178 | S | 5'-CAGTACTCCTCATCAGGC |
| DRB103 | SEQ ID NO: 179 | S | 5'-CTGTCCAGGTACCGCA |
| DRB104 | SEQ ID NO: 180 | U | 5'-ACCTCGGCCCGCCTCT |
| DRB105 | SEQ ID NO: 181 | U | 5'-GAGGCGCGCCGAGGTGGAC |
| DRB106 | SEQ ID NO: 182 | U | 5'-AGAGGCGCGCCGAGGTGGAC |
| DRB107 | SEQ ID NO: 183 | S | 5'-AGAAGCGGGGCCGG |
| DRB108 | SEQ ID NO: 184 | S | 5'-GAAGCGGGGCCGGG |
| DRB109 | SEQ ID NO: 185 | S | 5'-GAAGACAGGCGGGCCCTGG |
| DRB110 | SEQ ID NO: 186 | U | 5'-GCCTGTCTTCCAGGAAGTCC |
| DRB111 | SEQ ID NO: 187 | U | 5'-CTCAGACGTAGAGTACTCC |
| DRB112 | SEQ ID NO: 188 | S | 5'-GCCTGCTGCGGAGCACTGG |
| DRB113 | SEQ ID NO: 189 | S | 5'-GACCTCCTGGAAGACAGG |
| DRB114 | SEQ ID NO: 190 | U | 5'-CCTGTCCTCCAGGAGGTC |
| DRB115 | SEQ ID NO: 191 | U | 5'-ACGGGGTTGGTGAGAGCTT |
| DRB116 | SEQ ID NO: 192 | U | 5'-ACGGGGTTGTGGAGAGCTT |
| DRB117 | SEQ ID NO: 193 | U | 5'-ACGGGGCTGTGGAGAGCTT |
| DRB118 | SEQ ID NO: 194 | S | 5'-GAGGCGGGCCGAGGT |
| DRB119 | SEQ ID NO: 195 | U | 5'-GAGGCGGGCCGAGGTG |
| DRB120 | SEQ ID NO: 196 | U | 5'-GAGGCGGGCCGAGGTGGA |
| DRB121 | SEQ ID NO: 197 | U | 5'-GAGGCGGGCCGAGGTGGAC |

-continued

| Primer | Seq. ID No. | | Sequence |
|---|---|---|---|
| DRB122 | SEQ ID NO: 198 | U | 5'-AGAGGCGGGCCGAGGTGGAC |
| DRB123 | SEQ ID NO: 199 | T | 5'-GGCGGCCTAGCGCCGAGTA |
| DRB124 | SEQ ID NO: 200 | T | 5'-CCACXCGGCCCCGCTTCT |
| DRB125 | SEQ ID NO: 201 | T | 5'-GAGGCGGGCCGCGGT |
| DRB126 | SEQ ID NO: 202 | T | 5'-ACCGCGGCCCGCCTC |
| DRB127 | SEQ ID NO: 203 | T | 5'-GAAGCGGGCCGCGGT |
| DRB128 | SEQ ID NO: 204 | T | 5'-ACCGCGGCCCGCTTC |
| DRB129 | SEQ ID NO: 205 | T | 5'-ACTTCCTGGAAGACAGG |
| DRB130 | SEQ ID NO: 206 | T | 5'-CGCAAGTCCTCCTCTTG |
| DRB131 | SEQ ID NO: 207 | T | 5'-CAAGAGGAGGACTTGCG |
| DRB132 | SEQ ID NO: 208 | T | 5'-GAAGACAGGCGGGCCCTG |
| DRB133 | SEQ ID NO: 209 | T | 5'-AAGACAGGCGGGCCCTGG |
| DRB134 | SEQ ID NO: 210 | T | 5'-ACTTCCTGGAAGACGAG |
| DRB135 | SEQ ID NO: 211 | T | 5'-ACTTCCTGGAAGACGAGC |
| DRB136 | SEQ ID NO: 212 | T | 5'-ACATCCTGGAAGACAGGC |
| DRB137 | SEQ ID NO: 213 | T | 5'-GCCTGTCTTCCAGGATG |
| DRB138 | SEQ ID NO: 214 | T | 5'-GCAGAAGCGGGCCGCG |
| DRB139 | SEQ ID NO: 215 | T | 5'-CGCGGCCCGCTTCTGC |
| DRB140 | SEQ ID NO: 216 | T | 5'-GCAGAGGCGGGCCGCG |
| DRB141 | SEQ ID NO: 217 | T | 5'-CGCGGCCCGCCTCTGC |
| DRB142 | SEQ ID NO: 218 | T | 5'-GCAGAGGCGGGCCGAG |
| DRB143 | SEQ ID NO: 219 | T | 5'-CTCGGCCCGCCTCTGC |
| DRB144 | SEQ ID NO: 220 | T | 5'-GCGGAGGCGGGCCGAG |
| DRB145 | SEQ ID NO: 221 | T | 5'-CTCGGCCCGCCTCCGC |
| DRB146 | SEQ ID NO: 222 | T | 5'-CTCCGCTCCAGGAAGTC |
| DRB147 | SEQ ID NO: 223 | T | 5'-CGGGGTTGGTGAGAGCT |
| DRB148 | SEQ ID NO: 224 | T | 5'-CGGGGTTGTGGAGAGCT |
| DRB149 | SEQ ID NO: 225 | T | 5'-CGGGGCTGTGGAGAGCTT |
| DRB150 | SEQ ID NO: 226 | | 5'-TGTCCACCGCGGCCCGCGCCT |
| DRB153 | SEQ ID NO: 229 | | 5'-GAATTCCCAGCTCACACGGGACT |
| DRB154 | SEQ ID NO: 230 | | 5'-GGTGTCCACCGCGGCCCGCGC |
| DRB155 | SEQ ID NO: 231 | | 5'-AACCCCGTAGTTGTGTCTGCACAC |
| DRB156 | SEQ ID NO: 232 | | 5'-GGGGGAGTTCCGGG |
| DRB157 | SEQ ID NO: 233 | | 5'-CCCGGTACTCCCCC |
| DRB158 | SEQ ID NO: 234 | | 5'-CGCGGCCCGCCTCTG |
| DRB159 | SEQ ID NO: 235 | | 5'-CCGCGGCCCGCCTCTG |
| DRB160 | SEQ ID NO: 236 | | 5'-CCGXGGCCCGCCTCTGC |
| DRB161 | SEQ ID NO: 237 | | 5'-CCAGCGGCCCGCCTCTGC |
| DRB162 | SEQ ID NO: 238 | | 5'-GCAGAAXCGGGCCGCXGT |
| DRB163 | SEQ ID NO: 239 | | 5'-GCAGAAAGCGGGCCGCXGT |
| DRB164 | SEQ ID NO: 240 | | 5'-CAGAAGCGGGCCGCG |
| DRB165 | SEQ ID NO: 241 | | 5'-ACCTXGGCCCGCCXCTGC |
| DRB166 | SEQ ID NO: 242 | | 5'-ACCTXGGCCCGCCXCTG |
| DRB167 | SEQ ID NO: 243 | | 5'-GGAGCAGAAACGGGCCG |
| DRB168 | SEQ ID NO: 244 | | 5'-GGAGCAGAAACGGGCCGC |
| DRB169 | SEQ ID NO: 245 | | 5'-GCAGAAGCGGGCCXCG |
| DRB170 | SEQ ID NO: 246 | | 5'-GTCCACCTCGGCCCG |
| DRB171 | SEQ ID NO: 247 | | 5'-CGGGCCGCGGTGGAC |
| DRB172 | SEQ ID NO: 248 | | 5'-CGCCTCCGCTCCAGGAG |
| DRB173 | SEQ ID NO: 249 | | 5'-CTCCTGGAGCAGAGGCG |
| DRB174 | SEQ ID NO: 250 | | 5'-ACCGCGGCCCGCCTCT |
| DRB175 | SEQ ID NO: 251 | | 5'-CACCTXGGCCCGCCXCTG |
| DRB176 | SEQ ID NO: 252 | | 5'-CGXGGCCCGCCTCTG |
| DRB177 | SEQ ID NO: 253 | | 5'-CCGXGGCCCOCCTCTG |
| DRB178 | SEQ ID NO: 254 | | 5'-GGGGGAGTTCCGGGCG |
| DRB179 | SEQ ID NO: 255 | | 5'-CGCCCGGTACTCCCCC |
| DRB180 | SEQ ID NO: 256 | | 5'-XCCTGATGCCGAGTACTG |
| DRB181 | SEQ ID NO: 257 | | 5'-XCGGGGCTGTGGAGAGCTT |
| DRB182 | SEQ ID NO: 258 | | 5'-CTACGGGGCTGTGGAGAG |
| DRB183 | SEQ ID NO: 259 | | 5'-CTACGGGXCTGTGGAGAG |
| DRB184 | SEQ ID NO: 260 | | 5'-GTTCCGGGCGGTGAC |
| DRB185 | SEQ ID NO: 261 | | 5'-GGGGGAGTTXCGGGG |
| DRB186 | SEQ ID NO: 262 | | 5'-CGTCACCGCCCGGTAC |
| DRB187 | SEQ ID NO: 263 | | 5'-CGTCACCGCCCGXTAC |
| DRB188 | SEQ ID NO: 264 | | 5'-CACCCCTCATXGCCC |
| DRB189 | SEQ ID NO: 265 | | 5'-GCGGGCCGCGGTGGAC |
| DRB190 | SEQ ID NO: 266 | | 5'-CAGAGGCXGGCCGCGGT |
| DRB191 | SEQ ID NO: 267 | | 5'-GTTXCGGGCGGTGAC |
| DRB192 | SEQ ID NO: 268 | | 5'-TTCCGGGCGGTGAC |
| DRB193 | SEQ ID NO: 269 | | 5'-GGGGAGTTCCGGG |
| DRB194 | SEQ ID NO: 270 | | 5'-TCACCGCCCGGAAC |
| DRB195 | SEQ ID NO: 271 | | 5'-AGATACTTCTATAACCAG |
| DRB196 | SEQ ID NO: 272 | | 5'-AGACACTTCTATAACCAG |
| DRB197 | SEQ ID NO: 273 | | 5'-CTGGTTATAGAAGTATCT |
| DRB198 | SEQ ID NO: 274 | | 5'-CTGTCGCCGAGTCCTGG |
| DRB199 | SEQ ID NO: 275 | | 5'-GGGCGGCCTAGCGCCGAGT |
| DRB200 | SEQ ID NO: 276 | | 5'-GCAGAAAGCGGGCCGCXGT |
| DRB201 | SEQ ID NO: 277 | | 5'-GCGXCTGTCTTCCAGGATG |

| Primer | Seq. ID No. | Sequence |
|---|---|---|
| DRB202 | SEQ ID NO: 278 | 5'-CGXCTGTCTTCCAGGATG |
| DRB203 | SEQ ID NO: 279 | 5'-ACCGXGGCCCGCCTCTG |
| DRB204 | SEQ ID NO: 280 | 5'-CCGTCACCGCCCGXTAC |
| DRB205 | SEQ ID NO: 281 | 5'-GGGGAGTTCCGGGG |
| DRB206 | SEQ ID NO: 282 | 5'-TCACCGCCCGGAACTC |
| DRB207 | SEQ ID NO: 283 | 5'-TGACACTTATACTTACCCTGC |
| DRB208 | SEQ ID NO: 284 | 5'-TTGAAGCAGGATAAGTTTGAG |
| DRB209 | SEQ ID NO: 285 | 5'-CTTGAAGCAGGATAAGTTG |
| DRB210 | SEQ ID NO: 286 | 5'-GAATTCCCGCGCCGCGCTCA |
| DRB211 | SEQ ID NO: 287 | 5'-GAATTCCCGCGCCGCG |
| DRB212 | SEQ ID NO: 288 | 5'-GAATTCCCGCGCCGCGCTCAC |
| DRB213 | SEQ ID NO: 289 | 5'-ATGACACTCCCTCTTAGGCTG |
| DRB214 | SEQ ID NO: 290 | 5'-ACATCCTGGAAGACGAG |
| DRB215 | SEQ ID NO: 291 | 5'-CCGCTCCGTCCCATTGAA |
| DRB216 | SEQ ID NO: 292 | 5'-TTCAATGAGACGGAGCGG |
| DRB217 | SEQ ID NO: 293 | 5'-CATCCTGGAAGACGAG |
| DRB218 | SEQ ID NO: 294 | 5'-GCTCGTCTTCCAGCATG |
| DRB219 | SEQ ID NO: 295 | 5'-CGCTCGTCTTCCAGGATG |
| DRB220 | SEQ ID NO: 296 | 5'-GCTGTCGCCGAGTCCTGG |
| DRB221 | SEQ ID NO: 297 | 5'-CCTGTCGCCGAGTCCTGG |
| DRB222 | SEQ ID NO: 298 | 5'-CTGTCCAGGTACCGCA |
| DRB223 | SEQ ID NO: 299 | 5'-GGCGGCCTAGCGCCGAGTA |
| DRB224 | SEQ ID NO: 300 | 5'-CCACXCGGCCCCGCTTCT |
| DRB225 | SEQ ID NO: 301 | 5'-GAGGCGGGCCGCGGT |
| DRB226 | SEQ ID NO: 302 | 5'-ACCGCGGCCCGCCTC |
| DRB227 | SEQ ID NO: 303 | 5'-GAAGCGGGCCGCGGT |
| DRB228 | SEQ ID NO: 304 | 5'-ACCGCGGCCCGCTTC |
| DRB229 | SEQ ID NO: 305 | 5'-ACTTCCTGGAAGACAGG |
| DRB230 | SEQ ID NO: 306 | 5'-GACCTCCTGGAAGACAGG |
| DRB231 | SEQ ID NO: 307 | 5'-ACATCCTGGAAGACAAGC |
| DRB232 | SEQ ID NO: 308 | 5'-GACATCCTGGAAGACAAGC |
| DRB233 | SEQ ID NO: 309 | 5'-ACATCCTGGAAGACAAGCG |
| DRB300 | SEQ ID NO: 310 | 5'-GAATTCCCGCGCCGCGCTCACCTC |
| DRB305 | SEQ ID NO: 311 | 5'-GAATTCACAGGGACTCCAGGCC |

Preliminary testing shows that some probes, marked "S" above are more preferred than other probes, marked "U" above. Other probes, marked "T" above, have not yet been tested.

The hybridization patterns and specificity (1989 allele set) for the preferred reverse dot blot probes are show below. Where an "X" is used in the "specificity" column, the "X" designates inclusivity of all alleles indicated by the first two digits after the "*".

| Epitope | Name | Specificity |
|---|---|---|
| W-L-F | CRX60\DRB01 | DRB1*0101, 0102, 0103 |
| W-P-R | GH104 | DRB1*1501, 1502, 1601, 1602 |
| QDY | DRB100 | DRB5*0101, 0102, 0201, 0202 |
| K-D-F | GH111 | DRB1*0901 |
| YSTS | DRB46 | DRB1*030X, 110X, 130X, 104X |
| YSTG | GH102 | DRB1*080X, 1201 |
| V--H | DRB48 | DRB1*040X |
| G-YK | DRB19 | DRB1*070X |
| EV | DRB20 | DRB1*1001 |
| LR-S | GH57 | DRB3*0101 |
| LL-S | GH58 | DRB3*0201, 0202, 0301 |
| F--DR | DRB37/DRB109 | DRB1*0801, 0802, 1101, 1104, 1601, PEV; DRB5*0101, 0102 |
| F--DE | CRX68 | DRB1*1103 |
| I--DE | CRX06/DRB02 | DRB1*0103, 0402, 1102, 1301, 1302 |
| I--DK | DRB27 | DRB1*1303 |
| RR | DRB45 | DRB1*1001 |
| F--RR-E | DRB62 | DRB1*0901 |
| I--A | DRB63 | DRB1*1501, 1502; DRB5*0201, 0202 |
| Y | DRB103 | DRB1*0301, DRB3*0101 |
| E | DRB102 | DRB1*110X |
| S | DRB60 | DRB1*0405, 0801, 0803, 1303 |
| A--H | DRB112 | DRB1*1401, LY10 |
| V--S | DRB35 | DRB1*070X, 0901, 1201; DRB3*0101, 0301 |
| R | — | DRB1*0101, 0102, 0404, 0405, 0408, 1402 |
| K | — | DRB1*0401 |
| R--E | — | DRB1*0403, 0406, 0407 |
| RR--E | — | DRB1*1401, LY10; DRB4*0101 |
| I--DR | DRB72 | DRB1*0701, 0702 |

-continued

| Epitope | Name | Specificity |
|---|---|---|
| I--DR | DRB95 | DRB1*0803, 1201 |
| K--GR | — | DRB1*0301, 0302; DRB3*0101 |
| DR | DRB113 | DRB1*1602 |
| G (pos. 86) | — | See Table 5 |
| V (pos. 86) | — | See Table 5 |
| AV (pos. 86) | — | DRB1*0102, 1201; DRB5 |
| WNIIN | GH51 | DRB4*0101 |
| IHKR | DRB101 | DRB2*0101 |

EXAMPLE 9

Reverse Dot-Blot Typing Kit

HLA DRB typing kits incorporating a rapid and simple reverse dot blot hybridization format were designed to provide a simple and fast prescreening of samples before proceeding to fine subtyping involving allele specific amplification. The kits contain the amplification reagents, DNA for use as a positive control, nylon strips on which the probes have been immobilized, colorimetric detection reagents, reaction tubes, and instructions.

Typing was carried out using two amplification reactions, one using DRB general primers and the other using DRB1 specific primers. The primer pairs amplify under the same thermocycler conditions so that the two reactions could be carried out concurrently. Two panels of probes, one specific for each amplification reaction, were used in the reverse dot blot hybridization format. Each panel of probes was immobilized on a single nylon strip for ease of handling.

Biotinylated primers were used in the amplification reactions to allow for later detection using a colorimetric assay as described in Example 8, above. The DRB amplification primers used were CRX28 (SEQ ID NO: 67) and CRX29 (SEQ ID NO: 68). The DRB1 amplification primers were CRX28 (SEQ ID NO: 67) and CRX 37 (SEQ ID NO: 73). Both sets of primers are described in Example 8, above.

The two probe panels, one for hybridizing with the amplification products of the DRB amplification and the other for hybridizing with the amplification product from the DRB1-specific amplification, are shown below. The nucleotide sequence for each probe is found in the Sequence Listing section; the SEQ ID NO: for each probe is provided below.

| Probe Panel for the DRB Amplification | | | |
|---|---|---|---|
| Probe | Seq. ID No. | AA Sequence | Reactivity |
| 1 DRB01 | SEQ ID NO: 79 | WLF | DR1 |
| 2 GH104 | SEQ ID NO: 90 | WPR | DR2 |
| 3 DRB46 | SEQ ID NO: 123 | YSTS | DR3, 11, 13, 14 |
| 4 DRB48 | SEQ ID NO: 125 | V-H | DR4 |
| 5 DRB207 | SEQ ID NO: 283 | G-YK | DR7 |
| 6 GH102 | SEQ ID NO: 89 | YSTG | DR8, 12, 1404 |
| 7 DRB209 | SEQ ID NO: 285 | K-D-F | DR9 |
| 8 DRB20 | SEQ ID NO: 98 | EV | DR10 |
| 9 DRB102 | SEQ ID NO: 178 | E | DR11 |
| 10 DRB112 | SEQ ID NO: 188 | A-H | 1401, 1404 |
| 11 DRB07 | SEQ ID NO: 84 | F-DE | 1103 |
| C DRB42 | SEQ ID NO: 119 | TELGRP | ALL |

| Probe Panel for the DRB1 Amplification | | | |
|---|---|---|---|
| Probe | Seq. ID No. | AA Sequence | Reactivity |
| 12 DRB223 | SEQ ID NO: 299 | S | * |
| 13 DRB37 | SEQ ID NO: 114 | F-DR | * |
| 14 DRB203 | SEQ ID NO: 279 | R | * |
| 15 DRB163 | SEQ ID NO: 239 | K | 0401, 0409 |
| 16 DRB118 | SEQ ID NO: 194 | R-E/RR-E | * |
| 17 DRB02 | SEQ ID NO: 61 | I-DE | * |
| 18 DRB38 | SEQ ID NO: 115 | K-GR | DR3 |
| 19 DRB222 | SEQ ID NO: 298 | Y | 0301 |
| 20 DRB232 | SEQ ID NO: 308 | I-DK | 1303 |
| 21 DRB136 | SEQ ID NO: 212 | I-DR | 0803, 1201 (not DR7) |
| 22 DRB198 | SEQ ID NO: 274 | V-S | DR7, 0803, 1201 |
| C DRB42 | SEQ ID NO: 119 | TELGRP | ALL |

*sequence is found on a number of different alleles (see DRB1 amino acid alignment).

DRB probes 1–8 are specific to the region about amino acids 9–13; probe 9 is specific for amino acid 58; probe 10 is specific for amino acids 57–60; and probe 11 is specific for amino acids 67–74. DRB1 probes 13–18, 20, and 21 are specific to amino acids 67–74; probe 12 is specific to amino acid 57; probe 20 is specific to amino acid 26; and probe 22 is specific for amino acids 57–60. The control probe is specific for amino acids 51–56.

It should be noted that the probes shown in the above panels can also be labeled and used in the DRB typing methods described in Example 7. The same hybridization and wash conditions would be used. Interpretation of the hybridization pattern would be as described below.

The kits were packaged as two boxes: one box contained the DRB reagents and the other box contained the DRB1 reagents. Packaged in each box was either DRB or DRB1 PCR mix, DNA control, and typing strips; 8 mM magnesium chloride solution; mineral oil; SA-HRP conjugate; chromogen (TMB); reaction tubes; and instructions. PCR contains the reagents necessary for a PCR with the exception of the magnesium chloride and the template DNA. Other reagents and equipment needed to perform the methods described were supplied by the kit user; all are commonly available commercially.

Several sample preparation procedures suitable for use in PCR amplifications are known in the art. A preferred procedure is the Chelex extraction method described in Singer-Sam et al., 1989, *Amplifications* 3:11, and Walsh et al., 1991, *BioTechniques* 10(4):506–513, both of which are incorporated herein by reference. For examples of other techniques for extracting nucleic acids from biological samples, see those described in Sambrook et al., *Molecular Cloning: A Laboratory Manual* (New York, Cold Spring Harbor Laboratory, 1989); Arrand, Preparation of Nucleic Acid Probes, in pp. 18–30, *Nucleic Acid Hybridization: A Practical Approach* (Ed Hames and Higgins, IRL Press, 1985); or, in *PCR Protocols*, Chapters 18–20 (Innis et al., ed., Academic Press, 1990), which are all incorporated herein by reference.

Primer pairs for amplifying all DRB sequences and for amplifying specifically DRB1 sequences are used in two separate PCR reactions. Amplification reactions are essentially as described in Saiki et al., 1989, *Proc. Natl. Acad. Sci. USA* 86:6230–6234, incorporated herein by reference, with the modifications described below. Reactions are carried out using 25 µl of sample in a total volume of 100 µl, each reaction containing 50 mM KCL, 10 mM TrisHCl (pH 8.4), 1.5 mM $MgCl_2$, 10 µg Gelatin, 200 µM each dATP, dCTP, dGTP, and dTTP, 0.2 µM each biotinylated amplification primer, and 2.5 units of Thermus aquaticus DNA polymerase (PECI).

The same temperature profile is used for both amplification reaction, allowing both reactions to be carried out concurrently in the same thermocycler. The thermocycler is programmed for 35 cycles of the following temperature profile: denature at 95° C. for 60 seconds, anneal at 60° C. for 30 seconds, extend at 72° C. for 60 seconds. The thermocycler is programmed to incubate the sample for an additional 7 minutes at 72° C. following the last cycle.

The amplified DNA from the PCR is in double stranded form and must be denatured to allow hybridization with the oligonucleotide probes. The amplified DNA is denatured at 95° C. for 5 to 10 minutes in the thermocycler and maintained at that temperature until used. Alternatively, amplified DNA which has been denatured can be transferred directly from the 95° C. temperature into an ice bath. The rapid cooling stabilizes the DNA in a denatured form. The amplified DNA is then kept in the ice bath until it is required for the hybridization.

Twelve probes are affixed to each of two nylon membrane strips; one strip contains the probes to be used for hybridization with the DRB amplification product and the other strip contains the probes for hybridization with the DRB1-specific amplification product. Hybridization reactions are carried out in trays which hold each probe-containing strip in a separate well. The hybridization trays are commercially available from PECI and are typically supplied with the kit. The hybridization conditions described below are specific for the DRB hybridization. The DRB1 DNA hybridization protocol differs from the DRB protocol in that the DRB1 hybridization is at 55° C. instead of the 50° C. All other aspects of the protocol are identical.

In each well containing a strip, 3 ml of pre-warmed hybridization solution (4× SSPE and 0.5% weight/volume SDS) are added followed by 25 µl of amplified DNA. After careful mixing of the tray contents, the tray is placed in a 50° C. shaking water bath and incubated at 50° C. for 20 minutes at about 50 rpm.

The strips are washed initially in 10 ml of wash solution (1.0× SSPE and 0.1% weight/volume SDS) at room temperature for several seconds prior to the stringent wash and each well is then aspirated. The temperature and timing of the stringent wash are critical. Pre-warmed wash solution (10 ml) are added to each well and the tray is incubated in a 50° C. shaking water bath for 12 (±2) minutes at about 50 rpm. After aspirating each well, 10 ml of wash solution are added to each well, the tray is incubated at room temperature for 5 minutes on an orbital shaker at about 50 rpm, and the wells are again aspirated.

To each well containing a strip are added 3 ml of wash/enzyme conjugate solution (from a solution of 3.3 ml of wash solution and 27 µl of enzyme conjugate prepared within 15 minutes of use). The tray is incubated at room temperature for 20 minutes on an orbital shaker at approximately 50 rpm. The solution is aspirated from each well and the strips are washed in 10 ml of wash solution at room temperature for 5 minutes on an orbital shaker at approximately 50 rpm. Finally, the wash solution is aspirated from each well and the strips are ready for the color development step.

The color development steps are identical for both DRB and DRB1. To each well is added 10 ml of citrate buffer (100 mM Sodium Citrate, pH=5.0) and the tray is place on an orbital shaker for 5 minutes at approximately 50 rpm. Preferably, the color development solution is prepared during this time (no more than 10 minutes before use). The color development solution for each well is made from 10 ml of citrate buffer, 10 µl of 3% hydrogen peroxide, and 0.5 ml [TMB] chromogen solution (commercially available from PECI) mixed gently (do not vortex).

The tray is removed from the orbital shaker, the citrate buffer is aspirated, and 10 ml of the freshly-made color development solution is added to each well. The tray is shielded from light beginning with the color development step using an aluminum foil covering. The strips are developed at room temperature for up to 30 minutes on an orbital shaker at about 50 rpm. The development can be terminated as soon as the desired signal intensity has been reached.

After the desired signal intensity has been reached, the tray is removed from the shaker and the contents of each well are aspirated. The color development is stopped by washing with 10 ml of deionized water in each well. The water is added, the way is then shaken at room temperature for 5 minutes on an orbital shaker at about 50 rpm, and the contents of each well are slowly poured off. At least three washes should be performed.

The strips can be stored protected from light in the typing trays at between 2° C. and 8° C. for 2 to 3 days. The strips should be photographed wet for a permanent record. Strips can also be dried and stored in the dark, though some fading can occur.

Results are interpreted by reading the pattern of blue dots on the DNA Probe strips; each blue dot indicates that a biotinylated amplified product hybridized with the immobilized probe. The internal control probe (DRB42) [SEQ ID NO: 719], which detects all of the DRB alleles, is designed to produce a dot of intensity equal to or less than the intensity of other positive dots on the strip. This provides a guide as to the minimum dot intensity that should be scored as a positive.

Figure 10B:
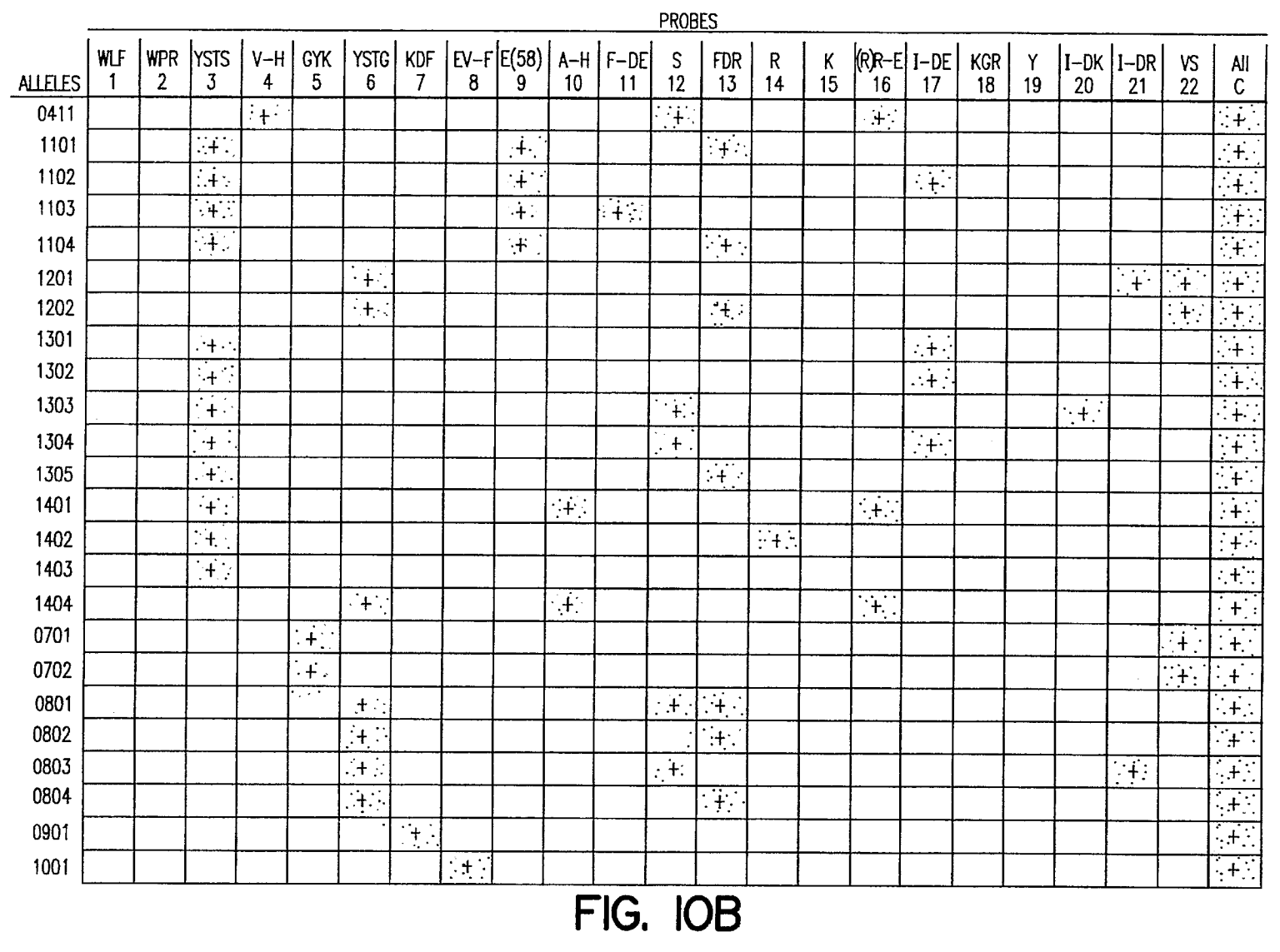
Figure 12A:
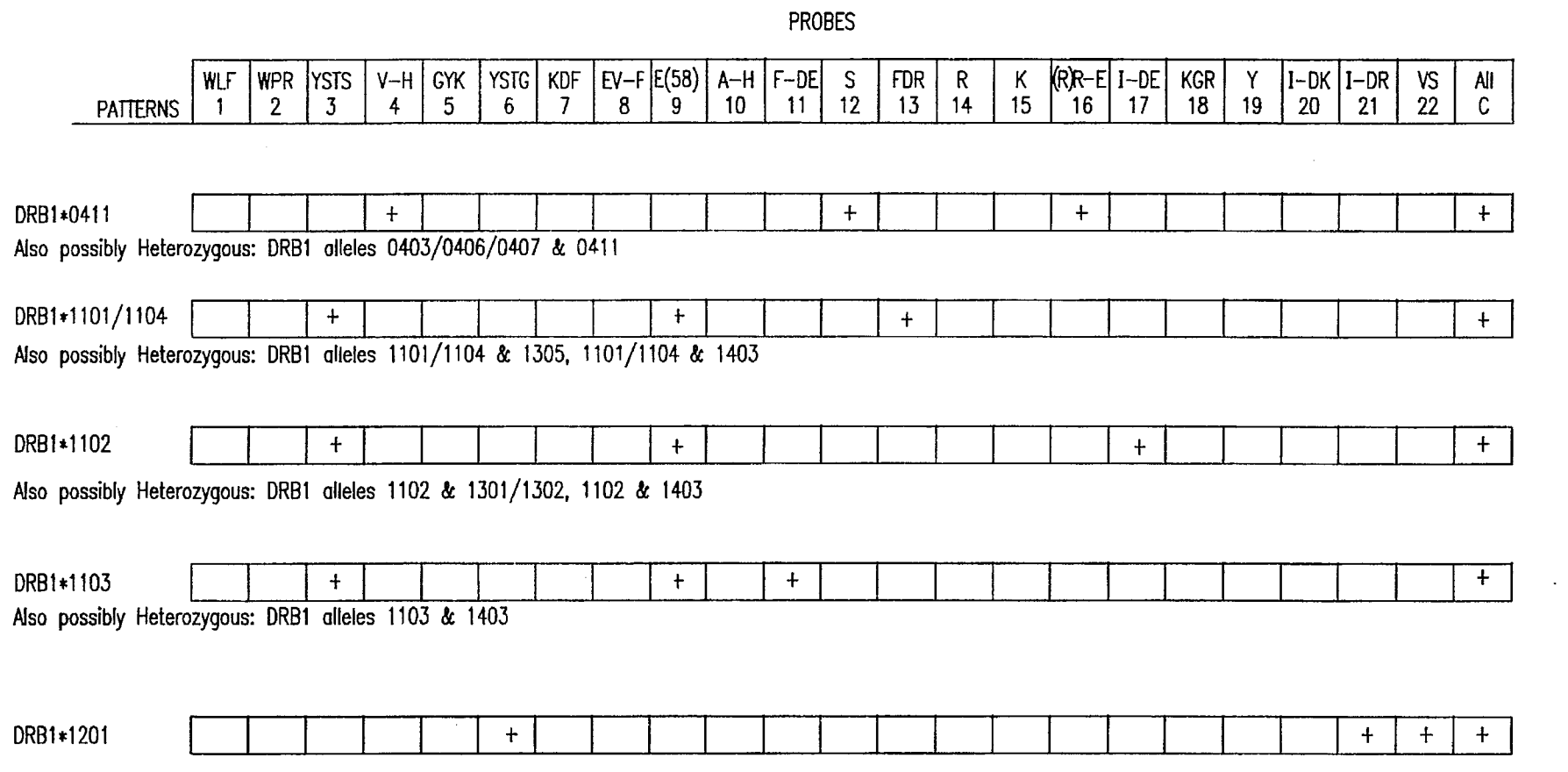

The probes of the above kit distinguish 31 HLA DRB1 types. Some of these probe-defined types are sets of related alleles. FIG. 10 shows the probe hybridization pattern for each allele of the 1990 allele set. FIGS. 11, 12, and 13 provide the possible interpretations for each probe hybridization pattern. Strip results can easily be interpreted directly using FIGS. 11–13.

A convenient alternative to manual interpretation of results is provided by a computer program which accepts the probe hybridization pattern as input, matches the input pattern to known allele patterns, and provides the possible interpretations. Suitable algorithms for matching the probe hybridization pattern to the possible allele combinations include simple table lookup and decision tree algorithms. Program input can be entered either manually or from an automated strip reader that detects the intensity of the blue hybridization dots.

As noted above, this reverse dot blot typing system does not fully descriminate among all possible types. For example, the system does not subtype DR2 serotypes. Certain heterozygous combinations also cannot be fully resolved. All of these can be resolved with additional primer pairs for allele-specific amplifications and probes, as discussed in Example 12, below.

Because of the hybridization positions of primers CRX28 (SEQ ID NO: 67) and CRX29 (SEQ ID NO: 68), it is not possible to detect amino acid variations which occur at position 86 when amplifying with this primer pair. Consequently, alleles which differ only at position 86 cannot be distinguished. There are seven pairs of alleles known which differ only in the present of a glycine or a valine at position 86; these allele pairs are listed below.

First Stage Typing

The first panel of probes is a similar to the probe panel shown in Table 4, differing by only a few probes. In the allele specificities shown in the probe panels below, an "X" as the last digit of an allele designation indicates that all alleles beginning with the specified number are recognized. For example, 030X is equivalent to 0301, 0302, and 0303.

| | | First Panel of HLA DRB Typing SSO Probes | | |
|---|---|---|---|---|
| Probe | SEQ ID NO: | Epitope | Alleles | Wash (SSPE, °C.) |
| CRX33 | SEQ ID NO: 69 | "W-L-F" | 010X | 0.4X, 42 |
| GH104 | SEQ ID NO: 90 | "W-P-R" | 150X, 160X | 0.2X, 42 |
| GH56 | SEQ ID NO: 86 | "YSTS" | 030X, 110X, 103X, 1401, 1402 | 0.2X, 42 |
| GH59 | SEQ ID NO: 87 | "V-H" | 040X | 0.2X, 42, 20 |
| CRX49 | SEQ ID NO: 74 | "G-YK" | 070X | 1.0X, 42 |
| GH102 | SEQ ID NO: 89 | "YSTG" | 080X, 120X, 1404 | 0.1X, 42 |
| GH111 | SEQ ID NO: 92 | "K-D-F" | 0901 | 0.4X, 42 |
| CRX34 | SEQ ID NO: 70 | "EV" | 1001 | 0.4X, 42 |
| GH122 | SEQ ID NO: 93 | "E" | 110X | 0.2X, 42 |
| CRX61 | SEQ ID NO: 80 | "S" | 0405, 0409, 0410, 0411, 0801, 0803, 1304, 1305 | 0.1X, 42 |
| CRX23 | SEQ ID NO: 66 | "A-H" | 1401, 1404 | 0.1X, 42 |
| CRX06 | SEQ ID NO: 61 | "I-DE" | 0103, 0402, 1102, 1301, 1302, 1304 | 0.1X, 42 |
| CRX35 | SEQ ID NO: 71 | "F-DR" | 1601, 1101, 1104, 1305, 0801, 0802, 0804, 1202 | 0.2X, 42 |
| CRX68 | SEQ ID NO: 84 | "F-DE" | 1103 | 0.2X, 42 |
| CRX62 | SEQ ID NO: 81 | "I-DK" | 1303 | 0.2X, 42 |
| CRX12 | SEQ ID NO: 63 | DRB "ALL" | All | 0.2X, 42 |

Allele Pairs Differing Only at Amino Acid Position 86

DRB1*1501 and DRB1*1502

DRB1*0302 and DRB1*0303

DRB1*0403 and DRB1*0407

DRB1*0404 and DRB1*0408

DRB1*1101 and DRB1*1104

DRB1*1301 and DRB1*1302

DRB1*0802 and DRB1*0804

EXAMPLE 10

General DRB1 Typing Strategy II

Example 4 describes one strategy for typing DRB1 alleles; an alternate strategy is described here. In order to obtain complete discrimination of all 45+ alleles at the DRB1 locus, a two stage assay is used. The first stage involves amplification of all samples with the DRB general primers, GH46 (SEQ ID NO: 67) and GH50 (SEQ ID NO: 68). The resulting PCR product is immobilized and probed (as in Example 4) with a first panel of probes to determine which allele specific amplifications, if any, need to be performed and the amplification products screened in the second stage. The amplification and hybridization protocols are essentially as described in Example 4. Interpretation of the hybridization pattern by reference to the allele specificities listed with each probe panel.

The probes are hybridized and then washed for 15 minutes at 42° C., except for GH59, which is washed for 20 minutes at 42° C. All SSPE wash solutions contain 0.1% SDS. Each probe is conjugated to HRP at the 5'-end. Based on the hybridization pattern obtained from the first probe panel, a subtyping step may be necessary using allele-specific amplification.

Each of the types, DR7, DR9, and DR10 have only one identifiable allele and are identified directly from the first stage probe panel. There are actually two alleles specifying the DR7 type, DRB1*0701 and DRB1*0702. However, these two alleles differ only in the third exon and cannot be distinguished by the present methods which amplify and detect sequences from the second exon. Therefore, only one distinct allele is identifiable by the methods of the present invention.

Second Stage Subtyping

DR2

Samples that contained a positive signal for W-P-R (GH104) [SEQ ID NO: 90], which all type as DR2 serologically, are amplified with a primer pair specific for alleles with the W-P-R epitope, AB83 (SEQ ID NO: 59) and AB60 (SEQ ID NO: 57). The resulting product is probed with the following panel.

Panel of HLA DR2 Typing SSO Probes

| Probe | SEQ ID NO: | Epitope | Alleles | Wash (SSPE, °C.) |
|---|---|---|---|---|
| DRB63 | SEQ ID NO: 140 | "I-A" | 150X | 0.1X, 42 |
| DRB113 | SEQ ID NO: 189 | "-DR" | 1602 | 0.1X, 42 OR 0.4X, 50 |
| CRX35 | SEQ ID NO: 71 | "F-DR" | 1601 | 0.2X, 42 |
| CRX57 | SEQ ID NO: 78 | "V" | 1501, 1502 | 0.2X, 42 |
| CRX56 | SEQ ID NO: 77 | "G" | 1502, 160X | 0.2X, 42 |
| DRB196 | SEQ ID NO: 272 | "H" (30) | 1503 | 1.0X, 42 |
| DRB197 | SEQ ID NO: 273 | "Y" (30) | 1501, 1502, 160X | 1.0X, 42 |
| GH104 | SEQ ID NO: 90 | "W-P-R" | DR2 | 0.2X, 42 |
| CRX12 | SEQ ID NO: 63 | DRB "ALL" | All | 0.2X, 42 |

The probes shown are hybridized and then washed for 15 minutes at 42° C. All SSPE wash solutions contain 0.1% SDS. Each probe is conjugated to HRP at the 5'-end.

DR3, DR5, DRw6

Samples that contained a positive signal for the YSTS epitope with probe GH56 (SEQ ID NO: 86) are either DR3, DR5, or DRw6. These alleles are amplified specifically with AB82 (SEQ ID NO: 58) and AB60 (SEQ ID NO: 57). The alleles can then be distinguished using the probe panel shown below.

Panel of HLA DR3, 5, w6 Typing SSO Probes

| Probe | SEQ ID NO: | Epitope | Alleles | Wash (SSPE, °C.) |
|---|---|---|---|---|
| CRX50 | SEQ ID NO: 75 | KGR | 030X | 0.2X, 50 |
| GH125 | SEQ ID NO: 94 | Y | 0301 | 0.2X, 50 |
| DRB180 | SEQ ID NO: 256 | A | 030X, 1301, 1302, 1305, 1402, 1403, 1405 | 0.2X, 42 |
| GH122 | SEQ ID NO: 93 | E | 110X | 0.2X, 42 |
| CRX61 | SEQ ID NO: 80 | S | 1303, 1304 | 0.2X, 42 |
| CRX61 | SEQ ID NO: 80 | S | 1303, 1304 | 0.2X, 42 |
| CRX23 | 66 | A-h | 1401 | 0.1X, 42 |
| CRX61 | SEQ ID NO: 80 | S | 1303, 1304 | 0.2X, 42 |
| CRX06 | 61 | I-DE | 1102, 1301-02 | 0.2X, 42 |
| CRX61 | SEQ ID NO: 80 | S | 1303, 1304 | 0.2X, 42 |
| CRX68 | 84 | FDE | 1103 | 0.2X, 42 |
| CRX61 | SEQ ID NO: 80 | S | 1303, 1304 | 0.2X, 42 |
| CRX35 | 71 | FDR | 1101, 1104, 1305 | 0.2X, 42 |
| CRX61 | SEQ ID NO: 80 | S | 1303, 1304 | 0.2X, 42 |
| CRX04 | 60 | R | 1402 | 0.1X, 42 |
| CRX61 | SEQ ID NO: 80 | S | 1303, 1304 | 0.2X, 42 |
| CRX57 | 78 | V | 0301, 0303, 1102, 1104, 1301, 1304, 1305, 1405 | 0.2X, 42 |
| CRX61 | SEQ ID NO: 80 | S | 1303, 1304 | 0.2X, 42 |
| CRX56 | 77 | G | 0302, 1101, 1302, 1303, 1305, 1402, 1403 | 0.2X, 42 |
| CRX61 | SEQ ID NO: 80 | S | 1303, 1304 | 0.2X, 42 |
| GH56 | 86 | YSTS | DR3, DR5, DRw6 | 0.2X, 42 |
| CRX61 | SEQ ID NO: 80 | S | 1303, 1304 | 0.2X, 42 |
| CRX12 | 63 | DRB "ALL" | ALL | 0.2X, 42 |

The probes shown are hybridized and then washed for 15 minutes at 42° C. All SSPE wash solutions contain 0.1% SDS. Each probe is conjugated to HRP at the 5'-end.

DR4

Samples that contained a positive signal for the VH epitope with probe GH59 (SEQ ID NO: 87) are DR4. These alleles are amplified specifically with AB54 (SEQ ID NO: 56) and AB60 (SEQ ID NO: 57). The alleles can then be distinguished using the probe panel shown below.

| Probe | Epitope | Allele | Wash |
|---|---|---|---|
| CRX61 | S | 0405, 0409, 0410, 0411 | 0.2X, 42 |
| CRX64 | K | 0401, 0409 | 2X, 40 |
| CRX04 | R | 0403, 0404, 0405, 0406, 0407, 0408, 0410, 0411 | 0.1X, 42 |
| CRX15 | R-E | 0403, 0406, 0407, 0411 | 0.4X, 55 |
| CRX06 | IDE | 0402 | |
| CRX57 | V | 0402, 0403, 0404, 0406, 0410, 0411 | 0.2X, 42 |
| CRX56 | G | 0401, 0405, 0407, 0408, 0409 | 0.2X, 42 |
| GH59 | V-H | DR4 | 0.2X, 42 |
| CRX12 | DRB "ALL" | ALL | 0.2X, 42 |

The probes shown are hybridized and then washed for 15 minutes at 42° C. with the exception of GH59 (SEQ ID NO: 87), which is washed for 20 minutes. All SSPE wash solutions contain 0.1% SDS. Each probe is conjugated to HRP at the 5'-end.

DR1, DRw8, and DRw12

Samples that contained a positive signal for the WLF epitope with probe CRX33 or positive for the YSTG epitope with probe GH102 (SEQ ID NO: 89) are amplified with the DRB1-specific primers, GH46 (SEQ ID NO: 67) and CRX37 (SEQ ID NO: 73). This also amplifies all DRB1 alleles except DR2, DR7, and DR9. The alleles can then be distinguished using the probe panel shown below.

| Probe | Epitope | Allele | Wash (SSPE, °C.) |
|---|---|---|---|
| CRX33 | WLF | 010X | 0.4X, 42 |
| CRX04 | R | 0101, 0102, 0403, 0404, 0405, 0406, 0407, 0408, 0410, 0411 | 0.1X, 42 |
| CRX06 | IDE | 0103, 1102, 1301, 1302 | 0.2X, 42 |
| CRX57 | V | 0301, 0402, 0403, 0404, 0406, 0410, 0411, 1102, 1103, 1104, 1301, 1304, 1401, 1404, 1405, 0804 | 0.2X, 42 |
| DRB181 | AV | 0102, 1201, 1202 | 0.1X, 42 |
| CRX56 | G | 0101, 0103, 0302, 0401, 0405, 0407, 0408, 0409, 1101, 1302, 1303, 0801, 0802, 0803, 1305, 1402, 1403 | 0.2X, 42 |
| GH102 | YSTG | 0801, 0802, 0803, 0804, 1201, 1202, 1404 | 0.1X, 42 |
| GH54 | V-S | 1201, 1202 | 0.4X, 42 |
| CRX63 | I-DR | 1201, 0803 | 0.2X, 42 |
| CRX35 | F-DR | 0801, 0802, 1202, 1101, 1104, 1305 | 0.2X, 42 |
| CRX12 | DRB "ALL" | ALL | 0.2X, 42 |

The probes shown are hybridized and then washed for 15 minutes at 42° C. All SSPE wash solutions contain 0.1% SDS. Each probe is conjugated to HRP at the 5'-end.

Since some epitopes recognized by the probes are shared in many alleles (such as FDR), the results obtained from the hybridization pattern with the above probe panel are compared to other allele specific amplifications to determine if the probe is associated with a DR1, DRw8, or DRw12, or is associated with another allele also amplified with the DRB1-specific primers. The design of primers specific for the WLF and YSTG epitopes will simplify the interpretation of the typing results.

EXAMPLE 11

Allele Subtyping in Heterozygotes

The pattern of hybridization with the probe panels of Example 10 alone may not be sufficient to unambiguously determine which alleles are present in certain heterozygous individuals. The probe hybridization pattern indicates which allele epitopes are present in the sample, but to determine the specific alleles present, it may be necessary to know which epitopes occur on which allele. Most frequently, such ambiguity does not arise because the epitope origin can usually be inferred from the limited possibilities of allelic combinations. The few cases which do arise can be resolved using allele-specific amplification.

In some DR5/DRw6 heterozygotes, the following probe pattern can result:

| Probe: | GH56 + | GH122 + | DRB180 + | CRX06 + | CRX35 + | CRX56 + | CRX57 |
|---|---|---|---|---|---|---|---|
| Epitope: | YSTS | E | DA | I-DE | F-DR | G | V |

Three different DR5/DRw6 heterozygote allele combinations produce this probe hybridization pattern; these combinations are listed below. These heterozygote allele combinations cannot be distinguished by any other probe.

DRB1*1101 and DRB1*1301

DRB1*1104 and DRB1*1302

DRB1*1102 and DRB1*1305

To distinguish these possibilities, additional primers were designed to take advantage of the unique dimorphism at position 86. All DRB1 alleles contain either a valine or a glycine at position 86. In each of the heterozygotes listed above, one of the alleles contains a valine at position 86 and the other contains a glycine. DRB1*1301, DRB1*1104, and DRB1*1102 each contain a valine at position 86; DRB1*1101, DRB1*1302, and DRB1*1305 each contain a glycine. Amplification using either a V or G specific primer in combination with a group specific primer (W-PR, VH, or YSTS) allows single allele amplification based on the polymorphism at position 86. In this manner, one of the two alleles present in each heterozygote can be selectively amplified and determined by direct probe hybridization. The second allele can be inferred from knowledge of the first allele based on the possible allelic combinations.

Subtyping DR5/DRw6 heterozygotes by single allele amplification was achieved using the PCR primer pairs AB82/RAP05 (SEQ ID NO: 58/SEQ ID NO: 312) and AB82/RAP06 (SEQ ID NO: 58/SEQ ID NO: 313). Amplification was carried out as in Example 10 except that the PCR buffer contained a final concentration of 1.0 mM MgCl$_2$. The thermocycler was programmed for 35 cycles, each with the following temperature profile: ramp to 94° C.; 30 seconds denaturation at 94° C.; 30 seconds annealing and extension at 70° C. Probe hybridization was carried out as before. The sequences of the V-specific (RAP06) [SEQ ID NO: 313] and G-specific (RAP05) [SEQ ID NO: 312] primers are shown below and in the sequence listing section. Although each was used in combination with AB82 (SEQ ID NO: 58), other group specific primers would be suitable.

| Primer | SEQ ID NO: | Specificity | Sequence |
|---|---|---|---|
| RAP05 | SEQ ID NO: 312 | G (86) | 5'-CGCTCACTGTGAAGCTCTCACCA |
| RAP06 | SEQ ID NO: 313 | V (86) | 5'-CGCTGCACTGTGAAGCTCTCCACA |

EXAMPLE 12

DRB Two-Stage Typing Kit

The typing kit described here is designed to uniquely identify the greatest number of types possible. The primers and probes are designed to provide rapid yet complete typing for the DRB1 and DRB3 loci in a reverse dot blot format. In order to obtain complete discrimination of all 45+ alleles at the DRB1 locus and the 3 alleles at the DRB3 locus, a two stage assay is used. The first stage involves amplification of all samples with the DRB general primers, DRB27 (SEQ ID NO: 105) and DRB28 (SEQ ID NO: 106). The resulting PCR product is screened against a strip with 13 probes to determine which allele specific amplifications, if any, need to be done and screened in the second stage.

Amplification and hybridization are carried out as in Example 9. The amplification product from the DRB general amplification is screened against a panel of probes containing eight probes specific for the first region of variability in the DRB1 locus, four probes specific for the three DRB3 alleles (52a, 52b, 52c), and one control probe. Additional probes can be added to this strip to type for the DRB5 locus which has three alleles and is found on DR2 haplotypes. The specific hybridization regions and types recognized are listed below.

| | Type recognized | Sequence Probed |
|---|---|---|
| 1 | DR1 | WLF |
| 2 | DR2 | WPR |
| 3 | DR3, 5, 6 | YSTS |
| 4 | DR4 | VH |
| 5 | DR7 | GYK |
| 6 | DR8, 12 | YSTG |
| 7 | DR9 | KDF |
| 8 | DR10 | EV |
| 9 | 52a | LRS |
| 10 | 52b, 52c | LLS |
| 11 | 52b | to be designed |
| 12 | 52c | to be designed |
| 13 | All | TELGRP |

The DRB3 type is determined from the results of this assay and, based on the results of this assay, it is determined which allele-specific amplifications (ASAs), if any, need to be done. Primers for five different ASAs are provided, though the most needed for typing any one sample is two. The same 3' primer, AB60 (SEQ ID NO: 57), for example, can be used for all five ASAs and typically would be included as a component of the PCR reaction mix provided in a kit. Amplification specificity is conferred by the 5' primers. The DRB type amplified and the epitope recognized by each of the 5' primers are listed below. Primers 2, 3, and 4 have been designed and tested extensively and are discussed in the examples, above.

| | Type Amplified | Hybridization Sequence |
|---|---|---|
| 1 | DR1 | WLF |
| 2 | DR2 | WPR |
| 3 | DR3, 5, 6 | YSTS |
| 4 | DR4 | VH |
| 5 | DR8, 12 | YSTG |

The second stage involves a series of probes which permit fine typing of the amplified products from the ASAs. In one embodiment, all probes are attached to a single strip and this single strip is used to type the product from all ASAs. Probes specific to the following regions are sufficient for typing the results of the ASAs.

| Region | Epitopes |
|---|---|
| 57–60 | DAE, S, E, A-H, V-S |
| 67–74 | R, I-DE, I-A, F-DR, DR, KGR, K, R-E/RR-E, F-DE, I-DK, I-DR,DR-L |
| 85–86 G, V, AV | |
| Other | E (a.a. 20), H (a.a. 30), Y (a.a. 26), S (aa. 37) |

The "other" region polymorphisms are very rare in Caucasian populations. However, an important goal of the present method is to be able to type non-Caucasian populations. Additional probes at these positions can be included to deal with possible ambiguities in recognizing heterozygotes versus homozygotes.

TABLE 9

Alleles not in the 1989 Allele Set

| Allele | | | | | ** | *** | *** | *** | *** | | | | | |
|---|---|---|---|---|---|---|---|---|---|---|---|---|---|---|
| **DRB1*0303 (SEQ ID NO: 6):** | | | | | | | | | | | | | | |
| TTC | AAT | GGG | ACG | | GAG | CGG | GTG | CGG | TTC | TAC | TCT | ACG | TCT | GAG |
| GAG | GAG | TCA | GTG | CA | CGC | CGG | GAC | AGC | TTC | CTG | GAG | AGA | TAC | TTT |
| GAG | CTG | GGG | CGG | GAG | CCT | TTC | GAC | GAG | GAC | GTG | GGG | GAG | TAC | CGG |
| GAC | CAG | AAG | CGG | CGC | GAT | GCC | GTG | GAG | TAC | TGG | AAC | AGC | CAG | AAG |
| GTG | GAG | AGC | TTC | ACA | GTG | CAG | CGG | CGA | TAC | TAC | TGC | AGA | CAC | AAC |
| **DRB1*0409 (SEQ ID NO: 15):** | | | | | | | | | | | | | | |
| TTC | AAC | GGG | ACG | | GAG | CGG | TTC | TTG | GAG | CAG | GTT | AAA | CAT | GAG |
| GAG | GAG | TCA | GTG | CA | CGC | CGG | GTG | CGG | TTC | CTG | GAC | AGA | TAC | TTC |
| GAG | CTG | GGG | CGG | GAG | TTC | GAC | GAC | AGC | GAC | GTG | GGG | GAG | TAC | CGG |
| GAC | CAG | AAG | CGG | CGT | GAT | GCC | GCC | GAG | TAC | TGG | AAC | AGC | CAG | AAG |
| GTG | GAG | AGC | TTC | ACA | GTG | CAG | CGG | CGG | ACC | TAC | TGC | AGA | CAC | AAC |
| **DRB1*0410 (SEQ ID NO: 16):** | | | | | | | | | | | | | | |
| TTC | AAC | GGG | ACG | | GAG | CGG | TTC | TTG | GAG | CAG | GTT | AAA | CAT | GAG |
| GAG | CTG | TCA | GTG | CA | CGC | CGG | GTG | CGG | TTC | CTG | GAC | AGA | TAC | TTC |
| GAG | CTG | GGG | CGG | GAG | TTC | TTC | GAC | AGC | GAC | GTG | GGG | GAG | TAC | CGG |
| GAC | CAG | AAG | CGG | CGT | AGC | GCC | GAC | GAG | TAC | TGG | AAC | AGC | CAG | AAG |
| GTG | GAG | AGC | TTC | ACA | GCG | GTG | CGG | CGG | ACC | TAC | TGC | AGA | CAC | AAC |
| **DRB1*0411 (SEQ ID NO: 17):** | | | | | | | | | | | | | | |
| TTC | AAC | GGG | ACG | | GAG | CGG | TTC | TTG | GAG | CAG | GTT | AAA | CAT | GAG |
| GAG | CTG | TCA | GTG | CA | CGC | CGG | GTG | CGG | TTC | CTG | GAC | AGA | TAC | TTC |
| GAG | CTG | GGG | CGG | GAG | TTC | TTC | GAC | AGC | GAC | GTG | GGG | GAG | TAC | CGG |
| GAC | CAG | AAG | CGG | CGT | AGC | GAC | GCC | GAC | TAC | TGG | AAC | AGC | CAG | AAG |
| GTG | GAG | AGC | TTC | ACA | GTG | CAG | CGG | CGG | ACC | TAC | TGC | AGA | CAC | AAC |
| **DRB1*0804 (SEQ ID NO: 22):** | | | | | | | | | | | | | | |
| TTC | AAT | GGG | ACG | | GAG | CGG | TTG | GAG | CAG | TAC | TCT | ACG | CAT | GAG |
| GAG | GAG | TAC | GTG | CA | CGG | CGG | GTG | TTC | GAC | CTG | GAC | AGA | TAC | TTC |
| GAG | CTG | GGG | CGG | GAG | TTC | AGC | GAC | GAC | TAC | GTG | GGG | GAG | TAC | CGG |
| GAC | CAG | AAG | CGG | CGC | GAT | GAG | GAG | GAC | ACC | TGG | AAC | AGC | CAG | AAG |
| GTG | GAG | AGC | TTC | ACA | GTG | CAG | CGG | CGG | CGA | TAC | TGC | AGA | CAC | AAC |
| **DRB1*1105 (SEQ ID NO: 29):** | | | | | | | | | | | | | | |
| TTC | AAT | GGG | ACG | | GAG | CGG | TTG | GAG | CAG | TAC | TCT | ACG | GGT | GAG |
| TAT | GAG | TAC | GTG | CA | CGC | CGG | GTG | TTC | GAC | CTG | GAC | AGA | TAC | TTC |
| GCG | CTG | GGG | CGG | GAG | TTC | AGC | GAC | GAC | TAC | GTG | GGG | GAG | TAC | CGG |
| GAC | GAC | AGG | CGG | CGC | GTC | GAG | GAG | TCC | ACC | TGG | AAC | AGC | TTC | AAG |
| TAC | GAG | AGC | TTC | ACA | GTG | CAG | CGG | CGG | CGA | TAC | TGC | AGA | CAC | AAC |
| **DRB1*1202 (SEQ ID NO: 31):** | | | | | | | | | | | | | | |
| TGT | TAT | GGG | ACG | | GAG | CGG | TTG | GAG | CAG | TAC | TCT | ACG | GGT | GAG |
| CAT | AAC | CTC | GTG | CA | CGG | CGG | GTG | TTC | TTA | CTG | GAC | AGA | TAC | TTC |
| GCG | GTG | GGG | CGG | GAG | TTC | GTC | GAC | AGC | TCC | GTG | GGG | GAG | TTC | CGG |
| GAC | TTC | AGG | CGC | CCT | GTC | GTG | GAG | GAC | ACC | TGG | AAC | AGC | CAG | AAG |
| TAC | GGG | AGC | TTC | GCT | GTG | CAG | CGG | CGG | CGA | TAT | TGC | AGA | CAC | AAC |

TABLE 9-continued

Alleles not in the 1989 Allele Set

```
DRB1*1304 (SEQ ID NO: 35):
TGT  CAT  TTC  TTC  AAT  GGG  ACG  CA   CGT  TTC  TTG  GGG  TAC  TCT  ACG  TCT  GAG
TAT  AAC  CAA  GAG  GAG  TAC  GTG  GAG  CGG  GTG  CGG  TTC  CTG  GAC  AGA  TAC  TTC
GCG  GTG  ACG  GAG  CTG  GGG  CGG  CGC  TTC  GAC  AGC  GAC  GTG  GGG  GAG  TTC  CGG
GAC  ATC  CTG  GAA  GAC  GAG  CGG  CCT  AGC  GCC  GAG  TAC  AGC  AAC  AGC  CAG  AAG
TAC  GGG  GTT  GTG  GAG  AGC  TTC  ACA  GTG  CAG  CGG  ACC  TAC  TGC  AGA  CAC  AAC

DRB1*1403 (SEQ ID NO: 39):
TGT  CAT  TTC  TTC  AAT  GGG  ACG  CA   CGT  TTC  TTG  GGG  TAC  TCT  ACG  TCT  GAG
CAT  AAC  CAG  GAG  GAG  AAC  GTG  GAG  CGG  GTG  CGG  TTC  CTG  GAC  AGA  TAC  TTC
GCG  GTG  ACG  GAG  CTG  GGG  CGC  CGC  TTC  GAC  AGC  GAC  GTG  GGG  GAG  TAC  CGG
GAC  CTC  CTG  GAA  GAC  GAG  CGG  CCT  AGG  GCC  GCT  TAC  AAC  AAC  AGC  CAG  AAG
TAC  GGG  GTT  GGT  GAG  AGC  TTC  ACA  GTG  CAG  CGG  ACC  TAC  TGC  AGA  CAC  AAC

DRB1*1405 (SEQ ID NO: 41):
TGT  CAA  TTC  TTC  AAT  GGG  ACG  CA   CGT  TTC  TTG  GGG  TAC  TCT  ACG  TCT  GAG
CAT  AAC  CAG  GAG  GAG  TTC  GTG  GAG  CGG  GTG  CGG  TTC  CTG  GAC  AGA  TAC  TTC
GCG  GTG  ACG  GAG  CTG  GGG  CGG  CGC  GAT  GCT  AGC  GAG  GTG  GGG  GAG  TAC  CGG
GAC  CTC  CTG  GAA  GAC  GAG  CGG  CCT  GAG  GTG  GAC  TGC  AAC  AAC  AGC  CAG  AAG
TAC  GGG  GTT  GTG  GAG  AGC  TTC  ACA  GTG  CAG  CGA  CGA  TAT  TGC  AGA  CAC  AAC

DRB1*1503 (SEQ ID NO: 44):
TGT  CAT  TTC  TTC  AAT  GGG  ACG  CA   CGT  TTC  TTG  CTG  CAG  CCT  AAG  AGG  GAG
TAT  AAC  CAG  GAG  GAG  TCC  GTG  GAG  CGG  GTG  CGG  TTC  CTG  GAC  AGA  CAC  TTC
GCG  GTG  ACG  GAG  CTG  GGG  CGG  CGG  TTC  GAC  AGC  GAC  GTG  GGG  GAG  TTC  CGG
GAC  ATC  CTG  GAA  GAC  GAG  CGG  CCT  GAC  GCT  GAG  TAC  TGG  AAC  AGC  CAG  AAG
TAC  GGG  GTT  GTG  GAG  AGC  TTC  ACA  GTG  CGA  CGG  CGA  TAC  TGC  AGA  CAC  AAC
```

We claim:

1. A primer selected from the group consisting of RAP05 (SEQ ID NO: 312), and RAP06 (SEQ ID NO: 313).

2. An oligonucleotide primer for amplifying a region of the second exon of a DRB locus, wherein said primer is selected from the group consisting of GH46 (SEQ ID NO: (SEQ ID NO: 67), CRX28 (SEQ ID NO: 67), GH50 (SEQ ID NO: 68), and CRX29 (SEQ ID NO: 68).

3. A pair of oligonucleotide primers for amplifying a region of the second exon of a DRB1 locus from all haplotypes except DR2, DR7, and DR9, wherein said pair consists of GH46 (SEQ ID NO: 67) or CRX28 (SEQ ID NO: 67) and CRX37 (SEQ ID NO: 73) or DRB17 (SEQ ID NO: 73).

* * * * *

SEQUENCE LISTING ( 1 ) GENERAL INFORMATION:

( i i i ) NUMBER OF SEQUENCES: 315

( 2 ) INFORMATION FOR SEQ ID NO:1:

( i ) SEQUENCE CHARACTERISTICS:
( A ) LENGTH: 269 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

| | | | | | | |
|---|---|---|---|---|---|---|
| CACGTTTCTT | GTGGCAGCTT | AAGTTTGAAT | GTCATTTCTT | CAATGGGACG | GAGCGGGTGC | 60 |
| GGTTGCTGGA | AAGATGCATC | TATAACCAAG | AGGAGTCCGT | GCGCTTCGAC | AGCGACGTGG | 120 |
| GGGAGTACCG | GGCGGTGACG | GAGCTGGGGC | GGCCTGATGC | CGAGTACTGG | AACAGCCAGA | 180 |
| AGGACCTCCT | GGAGCAGAGG | CGGGCCGCGG | TGGACACCTA | CTGCAGACAC | AACTACGGGG | 240 |
| TTGGTGAGAG | CTTCACAGTG | CAGCGGCGA | | | | 269 |

( 2 ) INFORMATION FOR SEQ ID NO:2:

( i ) SEQUENCE CHARACTERISTICS:
( A ) LENGTH: 269 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

| | | | | | | |
|---|---|---|---|---|---|---|
| CACGTTTCTT | GTGGCAGCTT | AAGTTTGAAT | GTCATTTCTT | CAATGGGACG | GAGCGGGTGC | 60 |
| GGTTGCTGGA | AAGATGCATC | TATAACCAAG | AGGAGTCCGT | GCGCTTCGAC | AGCGACGTGG | 120 |
| GGGAGTACCG | GGCGGTGACG | GAGCTGGGGC | GGCCTGATGC | CGAGTACTGG | AACAGCCAGA | 180 |
| AGGACCTCCT | GGAGCAGAGG | CGGGCCGCGG | TGGACACCTA | TTGCAGACAC | AACTACGGGG | 240 |
| CTGTGGAGAG | CTTCACAGTG | CAGCGGCGA | | | | 269 |

( 2 ) INFORMATION FOR SEQ ID NO:3:

( i ) SEQUENCE CHARACTERISTICS:
( A ) LENGTH: 269 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

| | | | | | | |
|---|---|---|---|---|---|---|
| CACGTTTCTT | GTGGCAGCTT | AAGTTTGAAT | GTCATTTCTT | CAATGGGACG | GAGCGGGTGC | 60 |
| GGTTGCTGGA | AAGATGCATC | TATAACCAAG | AGGAGTCCGT | GCGCTTCGAC | AGCGACGTGG | 120 |
| GGGAGTACCG | GGCGGTGACG | GAGCTGGGGC | GGCCTGATGC | CGAGTACTGG | AACAGCCAGA | 180 |
| AGGACATCCT | GGAAGACGAG | CGGGCCGCGG | TGGACACCTA | CTGCAGACAC | AACTACGGGG | 240 |
| TTGGTGAGAG | CTTCACAGTG | CAGCGGCGA | | | | 269 |

( 2 ) INFORMATION FOR SEQ ID NO:4:

( i ) SEQUENCE CHARACTERISTICS:

(A) LENGTH: 269 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:4:

| | | | | | | |
|---|---|---|---|---|---|---|
| CACGTTTCTT | GGAGTACTCT | ACGTCTGAGT | GTCATTTCTT | CAATGGGACG | GAGCGGGTGC | 60 |
| GGTACCTGGA | CAGATACTTC | CATAACCAGG | AGGAGAACGT | GCGCTTCGAC | AGCGACGTGG | 120 |
| GGGAGTTCCG | GGCGGTGACG | GAGCTGGGGC | GGCCTGATGC | CGAGTACTGG | AACAGCCAGA | 180 |
| AGGACCTCCT | GGAGCAGAAG | CGGGGCCGGG | TGGACAACTA | CTGCAGACAC | AACTACGGGG | 240 |
| TTGTGGAGAG | CTTCACAGTG | CAGCGGCGA  |            |            |            | 269 |

(2) INFORMATION FOR SEQ ID NO:5:

(i) SEQUENCE CHARACTERISTICS:
(A) LENGTH: 269 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:5:

| | | | | | | |
|---|---|---|---|---|---|---|
| CACGTTTCTT | GGAGTACTCT | ACGTCTGAGT | GTCATTTCTT | CAATGGGACG | GAGCGGGTGC | 60 |
| GGTTCCTGGA | GAGATACTTC | CATAACCAGG | AGGAGAACGT | GCGCTTCGAC | AGCGACGTGG | 120 |
| GGGAGTACCG | GGCGGTGACG | GAGCTGGGGC | GGCCTGATGC | CGAGTACTGG | AACAGCCAGA | 180 |
| AGGACCTCCT | GGAGCAGAAG | CGGGGCCGGG | TGGACAACTA | CTGCAGACAC | AACTACGGGG | 240 |
| TTGGTGAGAG | CTTCACAGTG | CAGCGGCGA  |            |            |            | 269 |

(2) INFORMATION FOR SEQ ID NO:6:

(i) SEQUENCE CHARACTERISTICS:
(A) LENGTH: 269 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:6:

| | | | | | | |
|---|---|---|---|---|---|---|
| CACGTTTCTT | GGAGTACTCT | ACGTCTGAGT | GTCATTTCTT | CAATGGGACG | GAGCGGGTGC | 60 |
| GGTTCCTGGA | GAGATACTTC | CATAACCAGG | AGGAGAACGT | GCGCTTCGAC | AGCGACGTGG | 120 |
| GGGAGTACCG | GGCGGTGACG | GAGCTGGGGC | GGCCTGATGC | CGAGTACTGG | AACAGCCAGA | 180 |
| AGGACCTCCT | GGAGCAGAAG | CGGGGCCGGG | TGGACAACTA | CTGCAGACAC | AACTACGGGG | 240 |
| TTGTGGAGAG | CTTCACAGTG | CAGCGGCGA  |            |            |            | 269 |

(2) INFORMATION FOR SEQ ID NO:7:

(i) SEQUENCE CHARACTERISTICS:
(A) LENGTH: 269 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:7:

| | | | | | | |
|---|---|---|---|---|---|---|
| CACGTTTCTT | GGAGCAGGTT | AAACATGAGT | GTCATTTCTT | CAACGGGACG | GAGCGGGTGC | 60 |

| GGTTCCTGGA | CAGATACTTC | TATCACCAAG | AGGAGTCAGT | GCGCTTCGAC | AGCGACGTGG | 120 |
| GGGAGTACCG | GGCGGTGACG | GAGCTGGGGC | GGCCTGATGC | CGAGTACTGG | AACAGCCAGA | 180 |
| AGGACCTCCT | GGAGCAGAAG | CGGGCCGCGG | TGGACACCTA | CTGCAGACAC | AACTACGGGG | 240 |
| TTGGTGAGAG | CTTCACAGTG | CAGCGGCGA  |            |            |            | 269 |

( 2 ) INFORMATION FOR SEQ ID NO:8:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

| CACGTTTCTT | GGAGCAGGTT | AAACATGAGT | GTCATTTCTT | CAACGGGACG | GAGCGGGTGC | 60 |
| GGTTCCTGGA | CAGATACTTC | TATCACCAAG | AGGAGTCAGT | GCGCTTCGAC | AGCGACGTGG | 120 |
| GGGAGTACCG | GGCGGTGACG | GAGCTGGGGC | GGCCTGATGC | CGAGTACTGG | AACAGCCAGA | 180 |
| AGGACATCCT | GGAAGACGAG | CGGGCCGCGG | TGGACACCTA | CTGCAGACAC | AACTACGGGG | 240 |
| TTGTGGAGAG | CTTCACAGTG | CAGCGGCGA  |            |            |            | 269 |

( 2 ) INFORMATION FOR SEQ ID NO:9:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

| CACGTTTCTT | GGAGCAGGTT | AAACATGAGT | GTCATTTCTT | CAACGGGACG | GAGCGGGTGC | 60 |
| GGTTCCTGGA | CAGATACTTC | TATCACCAAG | AGGAGTCAGT | GCGCTTCGAC | AGCGACGTGG | 120 |
| GGGAGTACCG | GGCGGTGACG | GAGCTGGGGC | GGCCTGATGC | CGAGTACTGG | AACAGCCAGA | 180 |
| AGGACCTCCT | GGAGCAGAGG | CGGGCCGAGG | TGGACACCTA | CTGCAGACAC | AACTACGGGG | 240 |
| TTGTGGAGAG | CTTCACAGTG | CAGCGGCGA  |            |            |            | 269 |

( 2 ) INFORMATION FOR SEQ ID NO:10:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

| CACGTTTCTT | GGAGCAGGTT | AAACATGAGT | GTCATTTCTT | CAACGGGACG | GAGCGGGTGC | 60 |
| GGTTCCTGGA | CAGATACTTC | TATCACCAAG | AGGAGTCAGT | GCGCTTCGAC | AGCGACGTGG | 120 |
| GGGAGTACCG | GGCGGTGACG | GAGCTGGGGC | GGCCTGATGC | CGAGTACTGG | AACAGCCAGA | 180 |
| AGGACCTCCT | GGAGCAGAGG | CGGGCCGCGG | TGGACACCTA | CTGCAGACAC | AACTACGGGG | 240 |
| TTGTGGAGAG | CTTCACAGTG | CAGCGGCGA  |            |            |            | 269 |

( 2 ) INFORMATION FOR SEQ ID NO:11:

( i ) SEQUENCE CHARACTERISTICS:
    ( A ) LENGTH: 269 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:11:

```
CACGTTTCTT  GGAGCAGGTT  AAACATGAGT  GTCATTTCTT  CAACGGGACG  GAGCGGGTGC      60
GGTTCCTGGA  CAGATACTTC  TATCACCAAG  AGGAGTCAGT  GCGCTTCGAC  AGCGACGTGG     120
GGGAGTACCG  GGCGGTGACG  GAGCTGGGGC  GGCCTAGCGC  CGAGTACTGG  AACAGCCAGA     180
AGGACCTCCT  GGAGCAGAGG  CGGGCCGCGG  TGGACACCTA  CTGCAGACAC  AACTACGGGG     240
TTGGTGAGAG  CTTCACAGTG  CAGCGGCGA                                          269
```

( 2 ) INFORMATION FOR SEQ ID NO:12:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
CACGTTTCTT  GGAGCAGGTT  AAACATGAGT  GTCATTTCTT  CAACGGGACG  GAGCGGGTGC      60
GGTTCCTGGA  CAGATACTTC  TATCACCAAG  AGGAGTCCGT  GCGCTTCGAC  AGCGACGTGG     120
GGGAGTACCG  GGCGGTGACG  GAGCTGGGGC  GGCCTGATGC  CGAGTACTGG  AACAGCCAGA     180
AGGACCTCCT  GGAGCAGAGG  CGGGCCGAGG  TGGACACCTA  CTGCAGACAC  AACTACGGGG     240
TTGTGGAGAG  CTTCACAGTG  CAGCGGCGA                                          269
```

( 2 ) INFORMATION FOR SEQ ID NO:13:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

```
CACGTTTCTT  GGAGCAGGTT  AAACATGAGT  GTCATTTCTT  CAACGGGACG  GAGCGGGTGC      60
GGTTCCTGGA  CAGATACTTC  TATCACCAAG  AGGAGTCAGT  GCGCTTCGAC  AGCGACGTGG     120
GGGAGTACCG  GGCGGTGACG  GAGCTGGGGC  GGCCTGATGC  CGAGTACTGG  AACAGCCAGA     180
AGGACCTCCT  GGAGCAGAGG  CGGGCCGAGG  TGGACACCTA  CTGCAGACAC  AACTACGGGG     240
TTGGTGAGAG  CTTCACAGTG  CAGCGGCGA                                          269
```

( 2 ) INFORMATION FOR SEQ ID NO:14:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

```
CACGTTTCTT  GGAGCAGGTT  AAACATGAGT  GTCATTTCTT  CAACGGGACG  GAGCGGGTGC      60
```

| GGTTCCTGGA | CAGATACTTC | TATCACCAAG | AGGAGTCAGT | GCGCTTCGAC | AGCGACGTGG | 120 |
| GGGAGTACCG | GGCGGTGACG | GAGCTGGGGC | GGCCTGATGC | CGAGTACTGG | AACAGCCAGA | 180 |
| AGGACCTCCT | GGAGCAGAGG | CGGGCCGCGG | TGGACACCTA | CTGCAGACAC | AACTACGGGG | 240 |
| TTGGTGAGAG | CTTCACAGTG | CAGCGGCGA  |            |            |            | 269 |

( 2 ) INFORMATION FOR SEQ ID NO:15:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

| CACGTTTCTT | GGAGCAGGTT | AAACATGAGT | GTCATTTCTT | CAACGGGACG | GAGCGGGTGC | 60 |
| GGTTCCTGGA | CAGATACTTC | TATCACCAAG | AGGAGTCAGT | GCGCTTCGAC | AGCGACGTGG | 120 |
| GGGAGTACCG | GGCGGTGACG | GAGCTGGGGC | GGCCTAGCGC | CGAGTACTGG | AACAGCCAGA | 180 |
| AGGACCTCCT | GGAGCAGAAG | CGGGCCGCGG | TGGACACCTA | CTGCAGACAC | AACTACGGGG | 240 |
| TTGGTGAGAG | CTTCACAGTG | CAGCGGCGA  |            |            |            | 269 |

( 2 ) INFORMATION FOR SEQ ID NO:16:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

| CACGTTTCTT | GGAGCAGGTT | AAACATGAGT | GTCATTTCTT | CAACGGGACG | GAGCGGGTGC | 60 |
| GGTTCCTGGA | CAGATACTTC | TATCACCAAG | AGGAGTCAGT | GCGCTTCGAC | AGCGACGTGG | 120 |
| GGGAGTACCG | GGCGGTGACG | GAGCTGGGGC | GGCCTAGCGC | CGAGTACTGG | AACAGCCAGA | 180 |
| AGGACCTCCT | GGAGCAGAGG | CGGGCCGCGG | TGGACACCTA | CTGCAGACAC | AACTACGGGG | 240 |
| TTGTGGAGAG | CTTCACAGTG | CAGCGGCGA  |            |            |            | 269 |

( 2 ) INFORMATION FOR SEQ ID NO:17:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

| CACGTTTCTT | GGAGCAGGTT | AAACATGAGT | GTCATTTCTT | CAACGGGACG | GAGCGGGTGC | 60 |
| GGTTCCTGGA | CAGATACTTC | TATCACCAAG | AGGAGTCAGT | GCGCTTCGAC | AGCGACGTGG | 120 |
| GGGAGTACCG | GGCGGTGACG | GAGCTGGGGC | GGCCTAGCGC | CGAGTACTGG | AACAGCCAGA | 180 |
| AGGACCTCCT | GGAGCAGAGG | CGGGCCGAGG | TGGACACCTA | CTGCAGACAC | AACTACGGGG | 240 |
| TTGTGGAGAG | CTTCACAGTG | CAGCGGCGA  |            |            |            | 269 |

( 2 ) INFORMATION FOR SEQ ID NO:18:

( i ) SEQUENCE CHARACTERISTICS:
 ( A ) LENGTH: 269 base pairs
 ( B ) TYPE: nucleic acid
 ( C ) STRANDEDNESS: single
 ( D ) TOPOLOGY: linear ( i i ) MOLECULE TYPE: DNA (genomic)

( x i ) SEQUENCE DESCRIPTION: SEQ ID NO:18:

| | | | | | | |
|---|---|---|---|---|---|---|
| CACGTTTCCT | GTGGCAGGGT | AAGTATAAGT | GTCATTTCTT | CAACGGGACG | GAGCGGGTGC | 60 |
| AGTTCCTGGA | AAGACTCTTC | TATAACCAGG | AGGAGTTCGT | GCGCTTCGAC | AGCGACGTGG | 120 |
| GGGAGTACCG | GGCGGTGACG | GAGCTAGGGC | GGCCTGTCGC | CGAGTCCTGG | AACAGCCAGA | 180 |
| AGGACATCCT | GGAGGACAGG | CGGGGCCAGG | TGGACACCGT | GTGCAGACAC | AACTACGGGG | 240 |
| TTGGTGAGAG | CTTCACAGTG | CAGCGGCGA | | | | 269 |

( 2 ) INFORMATION FOR SEQ ID NO:19:

( i ) SEQUENCE CHARACTERISTICS:
 ( A ) LENGTH: 269 base pairs
 ( B ) TYPE: nucleic acid
 ( C ) STRANDEDNESS: single
 ( D ) TOPOLOGY: linear ( i i ) MOLECULE TYPE: DNA (genomic)

( x i ) SEQUENCE DESCRIPTION: SEQ ID NO:19:

| | | | | | | |
|---|---|---|---|---|---|---|
| CACGTTTCTT | GGAGTACTCT | ACGGGTGAGT | GTTATTTCTT | CAATGGGACG | GAGCGGGTGC | 60 |
| GGTTCCTGGA | CAGATACTTC | TATAACCAAG | AGGAGTACGT | GCGCTTCGAC | AGCGACGTGG | 120 |
| GGGAGTACCG | GGCGGTGACG | GAGCTGGGGC | GGCCTAGCGC | CGAGTACTGG | AACAGCCAGA | 180 |
| AGGACTTCCT | GGAAGACAGG | CGGGCCCTGG | TGGACACCTA | CTGCAGACAC | AACTACGGGG | 240 |
| TTGGTGAGAG | CTTCACAGTG | CAGCGGCGA | | | | 269 |

( 2 ) INFORMATION FOR SEQ ID NO:20:

( i ) SEQUENCE CHARACTERISTICS:
 ( A ) LENGTH: 269 base pairs
 ( B ) TYPE: nucleic acid
 ( C ) STRANDEDNESS: single
 ( D ) TOPOLOGY: linear ( i i ) MOLECULE TYPE: DNA (genomic)

( x i ) SEQUENCE DESCRIPTION: SEQ ID NO:20:

| | | | | | | |
|---|---|---|---|---|---|---|
| CACGTTTCTT | GGAGTACTCT | ACGGGTGAGT | GTTATTTCTT | CAATGGGACG | GAGCGGGTGC | 60 |
| GGTTCCTGGA | CAGATACTTC | TATAACCAAG | AGGAGTACGT | GCGCTTCGAC | AGCGACGTGG | 120 |
| GGGAGTACCG | GGCGGTGACG | GAGCTGGGGC | GGCCTGATGC | CGAGTACTGG | AACAGCCAGA | 180 |
| AGGACTTCCT | GGAAGACAGG | CGGGCCCTGG | TGGACACCTA | CTGCAGACAC | AACTACGGGG | 240 |
| TTGGTGAGAG | CTTCACGGTG | CAGCGGCGA | | | | 269 |

( 2 ) INFORMATION FOR SEQ ID NO:21:

( i ) SEQUENCE CHARACTERISTICS:
 ( A ) LENGTH: 269 base pairs
 ( B ) TYPE: nucleic acid
 ( C ) STRANDEDNESS: single
 ( D ) TOPOLOGY: linear ( i i ) MOLECULE TYPE: DNA (genomic)

( x i ) SEQUENCE DESCRIPTION: SEQ ID NO:21:

```
CACGTTTCTT  GGAGTACTCT  ACGGGTGAGT  GTTATTTCTT  CAATGGGACG  GAGCGGGTGC      60
GGTTCCTGGA  CAGATACTTC  TATAACCAAG  AGGAATACGT  GCGCTTCGAC  AGCGACGTGG     120
GGGAGTACCG  GGCGGTGACG  GAGCTGGGGC  GGCCTAGCGC  CGAGTACTGG  AACAGCCAGA     180
AGGACATCCT  GGAAGACAGG  CGGGCCCTGG  TGGACACCTA  CTGCAGACAC  AACTACGGGG     240
TTGGTGAGAG  CTTCACAGTG  CAGCGGCGA                                          269
```

( 2 ) INFORMATION FOR SEQ ID NO:22:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

```
CACGTTTCTT  GGAGTACTCT  ACGGGTGAGT  GTTATTTCTT  CAATGGGACG  GAGCGGGTGC      60
GGTTCCTGGA  CAGATACTTC  TATAACCAAG  AGGAGTACGT  GCGCTTCGAC  AGCGACGTGG     120
GGGAGTACCG  GGCGGTGACG  GAGCTGGGGC  GGCCTGATGC  CGAGTACTGG  AACAGCCAGA     180
AGGACTTCCT  GGAAGACAGG  CGGGCCCTGG  TGGACACCTA  CTGCAGACAC  AACTACGGGG     240
TTGTGGAGAG  CTTCACAGTG  CAGCGGCGA                                          269
```

( 2 ) INFORMATION FOR SEQ ID NO:23:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

```
CACGTTTCTT  GAAGCAGGAT  AAGTTTGAGT  GTCATTTCTT  CAACGGGACG  GAGCGGGTGC      60
GGTATCTGCA  CAGAGGCATC  TATAACCAAG  AGGAGAACGT  GCGCTTCGAC  AGCGACGTGG     120
GGGAGTACCG  GGCGGTGACG  GAGCTGGGGC  GGCCTGTTGC  CGAGTCCTGG  AACAGCCAGA     180
AGGACTTCCT  GGAGCGGAGG  CGGGCCGAGG  TGGACACCGT  GTGCAGACAC  AACTACGGGG     240
TTGGTGAGAG  CTTCACAGTG  CAGAGGCGA                                          269
```

( 2 ) INFORMATION FOR SEQ ID NO:24:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

```
CACGTTTCTT  GGAGGAGGTT  AAGTTTGAGT  GTCATTTCTT  CAACGGGACG  GAGCGGGTGC      60
GGTTGCTGGA  AAGACGCGTC  CATAACCAAG  AGGAGTACGC  GCGCTACGAC  AGCGACGTGG     120
GGGAGTACCG  GGCGGTGACG  GAGCTGGGGC  GGCCTGATGC  CGAGTACTGG  AACAGCCAGA     180
AGGACCTCCT  GGAGCGGAGG  CGTGCCGCGG  TGGACACCTA  CTGCAGACAC  AACTACGGGG     240
TTGGTGAGAG  CTTCACAGTG  CAGCGGCGA                                          269
```

( 2 ) INFORMATION FOR SEQ ID NO:25:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

```
CACGTTTCTT  GGAGTACTCT  ACGTCTGAGT  GTCATTTCTT  CAATGGGACG  GAGCGGGTGC    60
GGTTCCTGGA  CAGATACTTC  TATAACCAAG  AGGAGTACGT  GCGCTTCGAC  AGCGACGTGG   120
GGGAGTTCCG  GGCGGTGACG  GAGCTGGGGC  GGCCTGATGA  GGAGTACTGG  AACAGCCAGA   180
AGGACTTCCT  GGAAGACAGG  CGGGCCGCGG  TGGACACCTA  CTGCAGACAC  AACTACGGGG   240
TTGGTGAGAG  CTTCACAGTG  CAGCGGCGA                                        269
```

( 2 ) INFORMATION FOR SEQ ID NO:26:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

```
CACGTTTCTT  GGAGTACTCT  ACGTCTGAGT  GTCATTTCTT  CAATGGGACG  GAGCGGGTGC    60
GGTTCCTGGA  CAGATACTTC  TATAACCAAG  AGGAGTACGT  GCGCTTCGAC  AGCGACGTGG   120
GGGAGTTCCG  GGCGGTGACG  GAGCTGGGGC  GGCCTGATGA  GGAGTACTGG  AACAGCCAGA   180
AGGACATCCT  GGAAGACGAG  CGGGCCGCGG  TGGACACCTA  CTGCAGACAC  AACTACGGGG   240
TTGTGGAGAG  CTTCACAGTG  CAGCGGCGA                                        269
```

( 2 ) INFORMATION FOR SEQ ID NO:27:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

```
CACGTTTCTT  GGAGTACTCT  ACGTCTGAGT  GTCATTTCTT  CAATGGGACG  GAGCGGGTGC    60
GGTTCCTGGA  CAGATACTTC  TATAACCAAG  AGGAGTACGT  GCGCTTCGAC  AGCGACGTGG   120
GGGAGTTCCG  GGCGGTGACG  GAGCTGGGGC  GGCCTGATGA  GGAGTACTGG  AACAGCCAGA   180
AGGACTTCCT  GGAAGACGAG  CGGGCCGCGG  TGGACACCTA  CTGCAGACAC  AACTACGGGG   240
TTGTGGAGAG  CTTCACAGTG  CAGCGGCGA                                        269
```

( 2 ) INFORMATION FOR SEQ ID NO:28:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

```
CACGTTTCTT GGAGTACTCT ACGTCTGAGT GTCATTTCTT CAATGGGACG GAGCGGGTGC        60
GGTTCCTGGA CAGATACTTC TATAACCAAG AGGAGTACGT GCGCTTCGAC AGCGACGTGG       120
GGGAGTTCCG GGCGGTGACG GAGCTGGGGC GGCCTGATGA GGAGTACTGG AACAGCCAGA       180
AGGACTTCCT GGAAGACAGG CGGGCCGCGG TGGACACCTA CTGCAGACAC AACTACGGGG       240
TTGTGGAGAG CTTCACAGTG CAGCGGCGA                                         269
```

( 2 ) INFORMATION FOR SEQ ID NO:29:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

```
CACGTTTCTT GGAGTACTCT ACGGGTGAGT GTCATTTCTT CAATGGGACG GAGCGGGTGC        60
GGTTCCTGGA CAGATACTTC TATAACCAAG AGGAGTACGT GCGCTTCGAC AGCGACGTGG       120
GGGAGTTCCG GGCGGTGACG GAGCTGGGGC GGCCTGATGA GGAGTACTGG AACAGCCAGA       180
AGGACTTCCT GGAAGACAGG CGGGCCGCGG TGGACACCTA CTGCAGACAC AACTACGGGG       240
TTGGTGAGAG CTTCACAGTG CAGCGGCGA                                         269
```

( 2 ) INFORMATION FOR SEQ ID NO:30:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

```
CACGTTTCTT GGAGTACTCT ACGGGTGAGT GTTATTTCTT CAATGGGACG GAGCGGGTGC        60
GGTTACTGGA GAGACACTTC CATAACCAGG AGGAGCTCCT GCGCTTCGAC AGCGACGTGG       120
GGGAGTTCCG GGCGGTGACG GAGCTGGGGC GGCCTGTCGC CGAGTCCTGG AACAGCCAGA       180
AGGACATCCT GGAAGACAGG CGCGCCGCGG TGGACACCTA TTGCAGACAC AACTACGGGG       240
CTGTGGAGAG CTTCACAGTG CAGCGGCGA                                         269
```

( 2 ) INFORMATION FOR SEQ ID NO:31:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

```
CACGTTTCTT GGAGTACTCT ACGGGTGAGT GTTATTTCTT CAATGGGACG GAGCGGGTGC        60
GGTTACTGGA GAGACACTTC CATAACCAGG AGGAGCTCCT GCGCTTCGAC AGCGACGTGG       120
GGGAGTTCCG GGCGGTGACG GAGCTGGGGC GGCCTGTCGC CGAGTCCTGG AACAGCCAGA       180
AGGACTTCCT GGAAGACAGG CGCGCCGCGG TGGACACCTA TTGCAGACAC AACTACGGGG       240
CTGTGGAGAG CTTCACAGTG CAGCGGCGA                                         269
```

5,567,809

87

-continued

88

( 2 ) INFORMATION FOR SEQ ID NO:32:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

```
CACGTTTCTT  GGAGTACTCT  ACGTCTGAGT  GTCATTTCTT  CAATGGGACG  GAGCGGGTGC      60
GGTTCCTGGA  CAGATACTTC  CATAACCAGG  AGGAGAACGT  GCGCTTCGAC  AGCGACGTGG     120
GGGAGTTCCG  GGCGGTGACG  GAGCTGGGGC  GGCCTGATGC  CGAGTACTGG  AACAGCCAGA     180
AGGACATCCT  GGAAGACGAG  CGGGCCGCGG  TGGACACCTA  CTGCAGACAC  AACTACGGGG     240
TTGTGGAGAG  CTTCACAGTG  CAGCGGCGA                                         269
```

( 2 ) INFORMATION FOR SEQ ID NO:33:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

```
CACGTTTCTT  GGAGTACTCT  ACGTCTGAGT  GTCATTTCTT  CAATGGGACG  GAGCGGGTGC      60
GGTTCCTGGA  CAGATACTTC  CATAACCAGG  AGGAGAACGT  GCGCTTCGAC  AGCGACGTGG     120
GGGAGTTCCG  GGCGGTGACG  GAGCTGGGGC  GGCCTGATGC  CGAGTACTGG  AACAGCCAGA     180
AGGACATCCT  GGAAGACGAG  CGGGCCGCGG  TGGACACCTA  CTGCAGACAC  AACTACGGGG     240
TTGGTGAGAG  CTTCACAGTG  CAGCGGCGA                                         269
```

( 2 ) INFORMATION FOR SEQ ID NO:34:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

```
CACGTTTCTT  GGGGTACTCT  ACGTCTGAGT  GTCATTTCTT  CAATGGGACG  GAGCGGGTGC      60
GGTTCCTGGA  CAGATACTTC  TATAACCAAG  AGGAGTACGT  GCGCTTCGAC  AGCGACGTGG     120
GGGAGTACCG  GGCGGTGACG  GAGCTGGGGC  GGCCTAGCGC  CGAGTACTGG  AACAGCCAGA     180
AGGACATCCT  GGAAGACAAG  CGGGCCGCGG  TGGACACCTA  CTGCAGACAC  AACTACGGGG     240
TTGGTGAGAG  CTTCACGGTG  CAGCGGCGA                                         269
```

( 2 ) INFORMATION FOR SEQ ID NO:35:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

| | | | | | | |
|---|---|---|---|---|---|---|
| CACGTTTCTT | GGGGTACTCT | ACGTCTGAGT | GTCATTTCTT | CAATGGGACG | GAGCGGGTGC | 60 |
| GGTTCCTGGA | CAGATACTTC | TATAACCAAG | AGGAGTACGT | GCGCTTCGAC | AGCGACGTGG | 120 |
| GGGAGTTCCG | GGCGGTGACG | GAGCTGGGGC | GGCCTAGCGC | CGAGTACTGG | AACAGCCAGA | 180 |
| AGGACATCCT | GGAAGACGAG | CGGGCCGCGG | TGGACACCTA | CTGCAGACAC | AACTACGGGG | 240 |
| TTGTGGAGAG | CTTCACAGTG | CAGCGGCGA | | | | 269 |

( 2 ) INFORMATION FOR SEQ ID NO:36:

( i ) SEQUENCE CHARACTERISTICS:
          ( A ) LENGTH: 269 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:36:

| | | | | | | |
|---|---|---|---|---|---|---|
| CACGTTTCTT | GGGGTACTCT | ACGTCTGAGT | GTCATTTCTT | CAATGGGACG | GAGCGGGTGC | 60 |
| GGTTCCTGGA | CAGATACTTC | CATAACCAGG | AGGAGAACGT | GCGCTTCGAC | AGCGACGTGG | 120 |
| GGGAGTTCCG | GGCGGTGACG | GAGCTGGGGC | GGCCTGATGC | CGAGTACTGG | AACAGCCAGA | 180 |
| AGGACTTCCT | GGAAGACAGG | CGGGCCGCGG | TGGACACCTA | CTGCAGACAC | AACTACGGGG | 240 |
| TTGGTGAGAG | CTTCACAGTG | CAGCGGCGA | | | | 269 |

( 2 ) INFORMATION FOR SEQ ID NO:37:

( i ) SEQUENCE CHARACTERISTICS:
          ( A ) LENGTH: 269 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:37:

| | | | | | | |
|---|---|---|---|---|---|---|
| CACGTTTCTT | GGGGTACTCT | ACGTCTGAGT | GTCATTTCTT | CAATGGGACG | GAGCGGGTGC | 60 |
| GGTTCCTGGA | CAGATACTTC | CATAACCAGG | AGGAGTTCGT | GCGCTTCGAC | AGCGACGTGG | 120 |
| GGGAGTACCG | GGCGGTGACG | GAGCTGGGGC | GGCCTGCTGC | GGAGCACTGG | AACAGCCAGA | 180 |
| AGGACCTCCT | GGAGCGGAGG | CGGGCCGAGG | TGGACACCTA | TTGCAGACAC | AACTACGGGG | 240 |
| TTGTGGAGAG | CTTCACAGTG | CAGCGGCGA | | | | 269 |

( 2 ) INFORMATION FOR SEQ ID NO:38:

( i ) SEQUENCE CHARACTERISTICS:
          ( A ) LENGTH: 269 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:38:

| | | | | | | |
|---|---|---|---|---|---|---|
| CACGTTTCTT | GGGGTACTCT | ACGTCTGAGT | GTCATTTCTT | CAATGGGACG | GAGCGGGTGC | 60 |
| GGTTCCTGGA | GAGATACTTC | CATAACCAGG | AGGAGAACGT | GCGCTTCGAC | AGCGACGTGG | 120 |
| GGGAGTACCG | GGCGGTGACG | GAGCTGGGGC | GGCCTGATGC | CGAGTACTGG | AACAGCCAGA | 180 |
| AGGACCTCCT | GGAGCAGAGG | CGGGCCGCGG | TGGACACCTA | CTGCAGACAC | AACTACGGGG | 240 |
| TTGGTGAGAG | CTTCACAGTG | CAGCGGCGA | | | | 269 |

( 2 ) INFORMATION FOR SEQ ID NO:39:

( i ) SEQUENCE CHARACTERISTICS:
    ( A ) LENGTH: 269 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:39:

```
CACGTTTCTT  GGGGTACTCT  ACGTCTGAGT  GTCATTTCTT  CAATGGGACG  GAGCGGGTGC    60
GGTTCCTGGA  GAGATACTTC  CATAACCAGG  AGGAGAACGT  GCGCTTCGAC  AGCGACGTGG   120
GGGAGTACCG  GGCGGTGACG  GAGCTGGGGC  GGCCTGATGC  CGAGTACTGG  AACAGCCAGA   180
AGGACCTCCT  GGAAGACAGG  CGGGCCCTGG  TGGACACCTA  CTGCAGACAC  AACTACGGGG   240
TTGGTGAGAG  CTTCACAGTG  CAGCGGCGA                                       269
```

( 2 ) INFORMATION FOR SEQ ID NO:40:

( i ) SEQUENCE CHARACTERISTICS:
    ( A ) LENGTH: 269 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:40:

```
CACGTTTCTT  GGGGTACTCT  ACGGGTGAGT  GTTATTTCTT  CAATGGGACG  GAGCGGGTGC    60
GGTTCCTGGA  CAGATACTTC  CATAACCAGG  AGGAGTTCGT  GCGCTTCGAC  AGCGACGTGG   120
GGGAGTACCG  GGCGGTGACG  GAGCTGGGGC  GGCCTGCTGC  GGAGCACTGG  AACAGCCAGA   180
AGGACCTCCT  GGAGCGGAGG  CGGGCCGAGG  TGGACACCTA  TTGCAGACAC  AACTACGGGG   240
TTGTGGAGAG  CTTCACAGTG  CAGCGGCGA                                       269
```

( 2 ) INFORMATION FOR SEQ ID NO:41:

( i ) SEQUENCE CHARACTERISTICS:
    ( A ) LENGTH: 269 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:41:

```
CACGTTTCTT  GGGGTACTCT  ACGTCTGAGT  GTCAATTCTT  CAATGGGACG  GAGCGGGTGC    60
GGTTCCTGGA  CAGATACTTC  CATAACCAGG  AGGAGTTCGT  GCGCTTCGAC  AGCGACGTGG   120
GGGAGTACCG  GGCGGTGACG  GAGCTGGGGC  GGCCTGATGC  TGAGTACTGG  AACAGCCAGA   180
AGGACCTCCT  GGAGCGGAGG  CGGGCCGAGG  TGGACACCTA  TTGCAGACAC  AACTACGGGG   240
TTGTGGAGAG  CTTCACAGTG  CAGCGGCGA                                       269
```

( 2 ) INFORMATION FOR SEQ ID NO:42:

( i ) SEQUENCE CHARACTERISTICS:
    ( A ) LENGTH: 269 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:42:

```
CACGTTTCCT GTGGCAGCCT AAGAGGGAGT GTCATTTCTT CAATGGGACG GAGCGGGTGC        60
GGTTCCTGGA CAGATACTTC TATAACCAGG AGGAGTCCGT GCGCTTCGAC AGCGACGTGG       120
GGGAGTTCCG GGCGGTGACG GAGCTGGGGC GGCCTGACGC TGAGTACTGG AACAGCCAGA      180
AGGACATCCT GGAGCAGGCG CGGGCCGCGG TGGACACCTA CTGCAGACAC AACTACGGGG      240
TTGTGGAGAG CTTCACAGTG CAGCGGCGA                                        269
```

( 2 ) INFORMATION FOR SEQ ID NO:43:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:43:

```
CACGTTTCCT GTGGCAGCCT AAGAGGGAGT GTCATTTCTT CAATGGGACG GAGCGGGTGC        60
GGTTCCTGGA CAGATACTTC TATAACCAGG AGGAGTCCGT GCGCTTCGAC AGCGACGTGG       120
GGGAGTTCCG GGCGGTGACG GAGCTGGGGC GGCCTGACGC TGAGTACTGG AACAGCCAGA      180
AGGACATCCT GGAGCAGGCG CGGGCCGCGG TGGACACCTA CTGCAGACAC AACTACGGGG      240
TTGGTGAGAG CTTCACAGTG CAGCGGCGA                                        269
```

( 2 ) INFORMATION FOR SEQ ID NO:44:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:44:

```
CACGTTTCCT GTGGCAGCCT AAGAGGGAGT GTCATTTCTT CAATGGGACG GAGCGGGTGC        60
GGTTCCTGGA CAGACACTTC TATAACCAGG AGGAGTCCGT GCGCTTCGAC AGCGACGTGG       120
GGGAGTTCCG GGCGGTGACG GAGCTGGGGC GGCCTGACGC TGAGTACTGG AACAGCCAGA      180
AGGACATCCT GGAGCAGGCG CGGGCCGCGG TGGACACCTA CTGCAGACAC AACTACGGGG      240
TTGTGGAGAG CTTCACAGTG CAGCGGCGA                                        269
```

( 2 ) INFORMATION FOR SEQ ID NO:45:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

```
CACGTTTCCT GTGGCAGCCT AAGAGGGAGT GTCATTTCTT CAATGGGACG GAGCGGGTGC        60
GGTTCCTGGA CAGATACTTC TATAACCAGG AGGAGTCCGT GCGCTTCGAC AGCGACGTGG       120
GGGAGTACCG GGCGGTGACG GAGCTGGGGC GGCCTGACGC TGAGTACTGG AACAGCCAGA      180
AGGACTTCCT GGAAGACAGG CGCGCCGCGG TGGACACCTA CTGCAGACAC AACTACGGGG      240
```

TTGGTGAGAG CTTCACAGTG CAGCGGCGA 269

( 2 ) INFORMATION FOR SEQ ID NO:46:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:46:

CACGTTTCCT GTGGCAGCCT AAGAGGGAGT GTCATTTCTT CAATGGGACG GAGCGGGTGC 60

GGTTCCTGGA CAGATACTTC TATAACCAGG AGGAGTCCGT GCGCTTCGAC AGCGACGTGG 120

GGGAGTACCG GGCGGTGACG GAGCTGGGGC GGCCTGACGC TGAGTACTGG AACAGCCAGA 180

AGGACCTCCT GGAAGACAGG CGCGCCGCGG TGGACACCTA CTGCAGACAC AACTACGGGG 240

TTGGTGAGAG CTTCACAGTG CAGCGGCGA 269

( 2 ) INFORMATION FOR SEQ ID NO:47:

( i ) SEQUENCE CHARACTERISTICS:
        ( A ) LENGTH: 226 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:47:

CACGTTTCTT GGAGCAGGCT AAGTGTGAGT GTCATATCTT CAATGGGATG AAGCGGGTGC 60

AGTACCTGAA CAGATACATC CATAAACGGG AGGAGAACCT GCCCTTCGAC AGCGACGTGG 120

AGGAGTTCCA GGCAGTTACG GAACTGGGGC GGCCTGTCGC AGAGAACTGG AACAGCCAGA 180

AGGGAATCCT GGAGGAGAAT CGGGACAAGG TGGACACCTA CTGCAG 226

( 2 ) INFORMATION FOR SEQ ID NO:48:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:48:

CACGTTTCTT GGAGCTGCGT AAGTCTGAGT GTCATTTCTT CAATGGGACG GAGCGGGTGC 60

GGTACCTGGA CAGATACTTC CATAACCAGG AGGAGTTCCT GCGCTTCGAC AGCGACGTGG 120

GGGAGTACCG GGCGGTGACG GAGCTGGGGC GGCCTGTCGC CGAGTCCTGG AACAGCCAGA 180

AGGACCTCCT GGAGCAGAAG CGGGGCCGGG TGGACAATTA CTGCAGACAC AACTACGGGG 240

TTGGTGAGAG CTTCACAGTG CAGCGGCGA 269

( 2 ) INFORMATION FOR SEQ ID NO:49:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:49:

| | | | | | |
|---|---|---|---|---|---|
| CACGTTTCTT | GGAGCTGCTT | AAGTCTGAGT | GTCATTTCTT | CAATGGGACG | GAGCGGGTGC | 60
| GGTTCCTGGA | GAGACACTTC | CATAACCAGG | AGGAGTACGC | GCGCTTCGAC | AGCGACGTGG | 120
| GGGAGTACCG | GGCGGTGAGG | GAGCTGGGGC | GGCCTGATGC | CGAGTACTGG | AACAGCCAGA | 180
| AGGACCTCCT | GGAGCAGAAG | CGGGGCCAGG | TGGACAATTA | CTGCAGACAC | AACTACGGGG | 240
| TTGTGGAGAG | CTTCACAGTG | CAGCGGCGA | | | | 269

( 2 ) INFORMATION FOR SEQ ID NO:50:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:50:

| | | | | | |
|---|---|---|---|---|---|
| CACGTTTCTT | GGAGCTGCTT | AAGTCTGAGT | GTCATTTCTT | CAATGGGACG | GAGCGGGTGC | 60
| GGTTCCTGGA | GAGATACTTC | CATAACCAGG | AGGAGTTCGT | GCGCTTCGAC | AGCGACGTGG | 120
| GGGAGTACCG | GGCGGTGACG | GAGCTGGGGC | GGCCTGTCGC | CGAGTCCTGG | AACAGCCAGA | 180
| AGGACCTCCT | GGAGCAGAAG | CGGGGCCAGG | TGGACAATTA | CTGCAGACAC | AACTACGGGG | 240
| TTGTGGAGAG | CTTCACAGTG | CAGCGGCGA | | | | 269

( 2 ) INFORMATION FOR SEQ ID NO:51:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:51:

| | | | | | |
|---|---|---|---|---|---|
| CACGTTTCTT | GGAGCAGGCT | AAGTGTGAGT | GTCATTTCCT | GAATGGGACG | GAGCGAGTGT | 60
| GGAACCTGAT | CAGATACATC | TATAACCAAG | AGGAGTACGC | GCGCTACAAC | AGTGACCTGG | 120
| GGGAGTACCA | GGCGGTGACG | GAGCTGGGGC | GGCCTGACGC | TGAGTACTGG | AACAGCCAGA | 180
| AGGACCTCCT | GGAGCGGAGG | CGGGCCGAGG | TGGACACCTA | CTGCAGATAC | AACTACGGGG | 240
| TTGTGGAGAG | CTTCACAGTG | CAGCGGCGA | | | | 269

( 2 ) INFORMATION FOR SEQ ID NO:52:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:52:

| | | | | | |
|---|---|---|---|---|---|
| CACGTTTCTT | GCAGCAGGAT | AAGTATGAGT | GTCATTTCTT | CAACGGGACG | GAGCGGGTGC | 60
| GGTTCCTGCA | CAGAGGCATC | TATAACCAAG | AGGAGGACTT | GCGCTTCGAC | AGCGACGTGG | 120
| GGGAGTACCG | GGCGGTGACG | GAGCTGGGGC | GGCCTGACGC | TGAGTACTGG | AACAGCCAGA | 180
| AGGACTTCCT | GGAAGACAGG | CGCGCCGCGG | TGGACACCTA | CTGCAGACAC | AACTACGGGG | 240
| TTGGTGAGAG | CTTCACAGTG | CAGCGGCGA | | | | 269

(2) INFORMATION FOR SEQ ID NO:53:

(i) SEQUENCE CHARACTERISTICS:
        (A) LENGTH: 269 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:53:

```
CACGTTTCTT  GCAGCAGGAT  AAGTATGAGT  GTCATTTCTT  CAACGGGACG  GAGCGGGTGC     60
GGTTCCTGCA  CAGAGGCATC  TATAACCAAG  AGGAGAACGT  GCGCTTCGAC  AGCGACGTGG    120
GGGAGTACCG  GGCGGTGACG  GAGCTGGGGC  GGCCTGACGC  TGAGTACTGG  AACAGCCAGA    180
AGGACTTCCT  GGAAGACAGG  CGCGCCGCGG  TGGACACCTA  CTGCAGACAC  AACTACGGGG    240
TTGGTGAGAG  CTTCACAGTG  CAGCGGCGA                                        269
```

(2) INFORMATION FOR SEQ ID NO:54:

(i) SEQUENCE CHARACTERISTICS:
        (A) LENGTH: 269 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:54:

```
CATGTTTCTT  GCAGCAGGAT  AAGTATGAGT  GTCATTTCTT  CAACGGGACG  GAGCGGGTGC     60
GGTTCCTGCA  CAGAGGCATC  TATAACCAAG  AGGAGAACGT  GCGCTTCGAC  AGCGACGTGG    120
GGGAGTACCG  GGCGGTGACG  GAGCTGGGGC  GGCCTGACGC  TGAGTACTGG  AACAGCCAGA    180
AGGACATCCT  GGAGCAGGCG  CGGGCCGCGG  TGGACACCTA  CTGCAGACAC  AACTACGGGG    240
CTGTGGAGAG  CTTCACAGTG  CAGCGGCGA                                        269
```

(2) INFORMATION FOR SEQ ID NO:55:

(i) SEQUENCE CHARACTERISTICS:
        (A) LENGTH: 269 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:55:

```
CATGTTTCTT  GCAGCAGGAT  AAGTATGAGT  GTCATTTCTT  CAACGGGACG  GAGCGGGTGC     60
GGTTCCTGCA  CAGAGGCATC  TATAACCAAG  AGGAGAACGT  GCGGTTCGAC  AGCGACGTGG    120
GGGAGTACCG  GGCGGTGACG  GAGCTGGGGC  GGCCTGACGC  TGAGTACTGG  AACAGCCAGA    180
AGGACATCCT  GGAGCAGGCG  CGGGCCGCGG  TGGACACCTA  CTGCAGACAC  AACTACGGGG    240
CTGTGGAGAG  CTTCACAGTG  CAGCGGCGA                                        269
```

(2) INFORMATION FOR SEQ ID NO: 56:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: genomic DNA ( x i ) SEQUENCE DESCRIPTION: SEQ ID NO: 56:

GGGGATCCTG GAGCAGGTTA AACA 24

( 2 ) INFORMATION FOR SEQ ID NO: 57:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 57:

CCGAATTCCG CTGCACTGTG AAGCTCTC 28

( 2 ) INFORMATION FOR SEQ ID NO: 58:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 58:

GGGGATCCTG GAGTACTCTA CGTC 24

( 2 ) INFORMATION FOR SEQ ID NO: 59:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 59:

GGGGATCCTG TGGCAGCCTA AGAGG 25

( 2 ) INFORMATION FOR SEQ ID NO: 60:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 60:

GAGCAGAGGC GGGCC 15

( 2 ) INFORMATION FOR SEQ ID NO: 61:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 61:

CATCCTGGAA GACGAGC 17

( 2 ) INFORMATION FOR SEQ ID NO: 62:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 62:

TCTAGAAGTA CTCTACGTCT                    20

( 2 ) INFORMATION FOR SEQ ID NO: 63:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 63:

AGCTGGGGCG GCCT                          14

( 2 ) INFORMATION FOR SEQ ID NO: 64:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 64:

ACCTCGGCCC GCCTC                         15

( 2 ) INFORMATION FOR SEQ ID NO: 65:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 65:

GAGCTGCTTA AGTCT                         15

( 2 ) INFORMATION FOR SEQ ID NO: 66:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 66:

CCTGCTGCGG AGCACTG                       17

( 2 ) INFORMATION FOR SEQ ID NO: 67:

( i ) SEQUENCE CHARACTERISTICS:
    ( A ) LENGTH: 27 base pairs (B) TYPE: nucleic acid
(C) STRANDEDNESS: single
(D) TOPOLOGY: linear (ii) MOLECULE TYPE: genomic DNA (xi) SEQUENCE DESCRIPTION: SEQ ID NO: 67:

CCGGATCCTT CGTGTCCCCA CAGCACG  27

(2) INFORMATION FOR SEQ ID NO: 68:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: genomic DNA (xi) SEQUENCE DESCRIPTION: SEQ ID NO: 68:

CTCCCCAACC CCGTAGTTGT GTCTGCA  27

(2) INFORMATION FOR SEQ ID NO:69:

(i) SEQUENCE CHARACTERISTICS:
(A) LENGTH: 269 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:69:

CACGTTTCTT GGAGCTGCTT AAGTCTGAGT GTCATTTCTT CAATGGGACG GAGCGGGTGC  60

GGTTCCTGGA GAGACACTTC CATAACCAGG AGGAGTACGC GCGCTTCGAC AGCGACGTGG  120

GGGAGTACCG GGCGGTGAGG GAGCTGGGGC GGCCTGATGC CGAGTACTGG AACAGCCAGA  180

AGGACCTCCT GGAGCAGAAG CGGGGCCAGG TGGACAATTA CTGCAGACAC AACTACGGGG  240

TTGGTGAGAG CTTCACAGTG CAGCGGCGA  269

(2) INFORMATION FOR SEQ ID NO: 70:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: genomic DNA (xi) SEQUENCE DESCRIPTION: SEQ ID NO: 70:

CTCAAACTTA ACCTCCTC  18

(2) INFORMATION FOR SEQ ID NO: 71:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: genomic DNA (xi) SEQUENCE DESCRIPTION: SEQ ID NO: 71:

CCTGTCTTCC AGGAAGT  17

(2) INFORMATION FOR SEQ ID NO: 72:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 72:

CCCGCCTCCG CTCCA 15

( 2 ) INFORMATION FOR SEQ ID NO: 73:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 73:

GAATTCCCGC GCCGCGCT 18

( 2 ) INFORMATION FOR SEQ ID NO: 74:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 74:

TGACACTTAT ACTTACC 17

( 2 ) INFORMATION FOR SEQ ID NO: 75:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 75:

CACCCGGCCC CGCTTCT 17

( 2 ) INFORMATION FOR SEQ ID NO: 76:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 76:

GAGCAGAAGC GGGCC 15

( 2 ) INFORMATION FOR SEQ ID NO: 77:

( i ) SEQUENCE CHARACTERISTICS:
        ( A ) LENGTH: 16 base pairs
        ( B ) TYPE: nucleic acid
        ( C ) STRANDEDNESS: single ( D ) TOPOLOGY: linear ( i i ) MOLECULE TYPE: genomic DNA ( x i ) SEQUENCE DESCRIPTION: SEQ ID NO: 77:

CGGGTTGGTG AGAGCT 16

( 2 ) INFORMATION FOR SEQ ID NO: 78:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 78:

CGGGTTGTGG AGAGCT 16

( 2 ) INFORMATION FOR SEQ ID NO: 79:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 79:

CAAACTTAAG CTGCCAC 17

( 2 ) INFORMATION FOR SEQ ID NO: 80:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 80:

GCGGCCTAGC GCCGAGT 17

( 2 ) INFORMATION FOR SEQ ID NO: 81:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 81:

ACATCCTGGA AGACAAG 17

( 2 ) INFORMATION FOR SEQ ID NO: 82:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 82:

ACATCCTGGA AGACAGG 17

( 2 ) INFORMATION FOR SEQ ID NO: 83:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 83:

GAGGANAAGC NGGCC 15

( 2 ) INFORMATION FOR SEQ ID NO: 84:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 84:

GACTTCCTGG AAGACGA 17

( 2 ) INFORMATION FOR SEQ ID NO: 85:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 85:

GCTGTTCCAG GACTC 15

( 2 ) INFORMATION FOR SEQ ID NO: 86:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 86:

CAGACGTAGA GTACTCC 17

( 2 ) INFORMATION FOR SEQ ID NO: 87:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 87:

CATGTTTAAC CTGCTCC 17

( 2 ) INFORMATION FOR SEQ ID NO: 88:

( i ) SEQUENCE CHARACTERISTICS:
   ( A ) LENGTH: 19 base pairs
   ( B ) TYPE: nucleic acid
   ( C ) STRANDEDNESS: single
   ( D ) TOPOLOGY: linear ( i i ) MOLECULE TYPE: genomic DNA ( x i ) SEQUENCE DESCRIPTION: SEQ ID NO: 88:

CTCCCGTTTA TGGATGTAT 19

( 2 ) INFORMATION FOR SEQ ID NO: 89:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: genomic DNA ( x i ) SEQUENCE DESCRIPTION: SEQ ID NO: 89:

GAAATAACAC TCACCCGTAG 20

( 2 ) INFORMATION FOR SEQ ID NO: 90:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear ( i i ) MOLECULE TYPE: genomic DNA ( x i ) SEQUENCE DESCRIPTION: SEQ ID NO: 90:

TGACACTCCC TCTTAGGCT 19

( 2 ) INFORMATION FOR SEQ ID NO: 91:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: genomic DNA ( x i ) SEQUENCE DESCRIPTION: SEQ ID NO: 91:

CTTGCAGCAG GATAAGTATG 20

( 2 ) INFORMATION FOR SEQ ID NO: 92:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: genomic DNA ( x i ) SEQUENCE DESCRIPTION: SEQ ID NO: 92:

TTGAAGCAGG ATAAGTTTGA 20

( 2 ) INFORMATION FOR SEQ ID NO: 93:

( i ) SEQUENCE CHARACTERISTICS:
      ( A ) LENGTH: 17 base pairs
      ( B ) TYPE: nucleic acid
      ( C ) STRANDEDNESS: single ( D ) TOPOLOGY: linear ( i i ) MOLECULE TYPE: genomic DNA ( x i ) SEQUENCE DESCRIPTION: SEQ ID NO: 93:

CAGTACTCCT CATCAGG 17

( 2 ) INFORMATION FOR SEQ ID NO: 94:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 94:

CTGTCCAGGT ACCGCAC 17

( 2 ) INFORMATION FOR SEQ ID NO: 95:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 95:

GAATTCCCGC GCCGCGCTCA CCTCG 25

( 2 ) INFORMATION FOR SEQ ID NO: 96:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 96:

GAATTCCCGC GCCGCGCTCA CCTCGCC 27

( 2 ) INFORMATION FOR SEQ ID NO: 97:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 97:

TGACACTTAT ACTTACCGTC 20

( 2 ) INFORMATION FOR SEQ ID NO: 98:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 98:

CTCAAACTTA ACCTCCTCC 19

(2) INFORMATION FOR SEQ ID NO: 99:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 99:

GAGCAGAGGC GGGC 14

(2) INFORMATION FOR SEQ ID NO: 100:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 100:

GCCTGTCTTC CAGGAAGT 18

(2) INFORMATION FOR SEQ ID NO: 101:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 101:

GCCCGCTTCT GCTC 14

(2) INFORMATION FOR SEQ ID NO: 102:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 102:

GAGCAGAAGC NGGCC 15

(2) INFORMATION FOR SEQ ID NO: 103:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 103:

CATCCTGGAA GACAGG 16

(2) INFORMATION FOR SEQ ID NO: 104:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: genomic DNA ( x i ) SEQUENCE DESCRIPTION: SEQ ID NO: 104:

CATCCTGGAA GACAGGCGCG 20

( 2 ) INFORMATION FOR SEQ ID NO: 105:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 105:

ACATCCTGGA AGACAAGC 18

( 2 ) INFORMATION FOR SEQ ID NO: 106:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 106:

ACCTCGGCCC NCCTC 15

( 2 ) INFORMATION FOR SEQ ID NO: 107:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 107:

GAATTCCCGC GCCGCGCTCA CCT 23

( 2 ) INFORMATION FOR SEQ ID NO: 108:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 108:

CTCCCGTTTA TGGATGTATC 20

( 2 ) INFORMATION FOR SEQ ID NO: 109:

( i ) SEQUENCE CHARACTERISTICS:
    ( A ) LENGTH: 15 base pairs
    ( B ) TYPE: nucleic acid
    ( C ) STRANDEDNESS: single (D) TOPOLOGY: linear (ii) MOLECULE TYPE: genomic DNA (xi) SEQUENCE DESCRIPTION: SEQ ID NO: 109:

TGTCCAGGTA CCGCA                                                                                                    15

(2) INFORMATION FOR SEQ ID NO: 110:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 110:

ACTCATGTTT AACCTGCTCC                                                                                         20

(2) INFORMATION FOR SEQ ID NO: 111:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 111:

CTCATGTTTA ACCTGCTCC                                                                                          19

(2) INFORMATION FOR SEQ ID NO: 112:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 112:

TGTCGCCGAG TCCTGG                                                                                              16

(2) INFORMATION FOR SEQ ID NO: 113:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 113:

CGCCTGTCTT CCAGGAAGT                                                                                          19

(2) INFORMATION FOR SEQ ID NO: 114:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 114:

CCGCCTGTCT TCCAGGAAGT                                                                                          20

( 2 ) INFORMATION FOR SEQ ID NO: 115:

( i ) SEQUENCE CHARACTERISTICS:
                ( A ) LENGTH: 19 base pairs
                ( B ) TYPE: nucleic acid
                ( C ) STRANDEDNESS: single
                ( D ) TOPOLOGY: linear ( i i ) MOLECULE TYPE: genomic DNA ( x i ) SEQUENCE DESCRIPTION: SEQ ID NO: 115:

TCCACCCGGC CCCGCTTCT                                                                                           19

( 2 ) INFORMATION FOR SEQ ID NO: 116:

( i ) SEQUENCE CHARACTERISTICS:
                ( A ) LENGTH: 14 base pairs
                ( B ) TYPE: nucleic acid
                ( C ) STRANDEDNESS: single
                ( D ) TOPOLOGY: linear ( i i ) MOLECULE TYPE: genomic DNA ( x i ) SEQUENCE DESCRIPTION: SEQ ID NO: 116:

GAGCAGAAGC GGGC                                                                                                14

( 2 ) INFORMATION FOR SEQ ID NO: 117:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( i i ) MOLECULE TYPE: genomic DNA ( x i ) SEQUENCE DESCRIPTION: SEQ ID NO: 117:

GAGNAGAAGC NGGCC                                                                                               15

( 2 ) INFORMATION FOR SEQ ID NO: 118:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( i i ) MOLECULE TYPE: genomic DNA ( x i ) SEQUENCE DESCRIPTION: SEQ ID NO: 118:

GGCCCGCTTC TGCTC                                                                                               15

( 2 ) INFORMATION FOR SEQ ID NO: 119:

( i ) SEQUENCE CHARACTERISTICS:
                ( A ) LENGTH: 19 base pairs
                ( B ) TYPE: nucleic acid
                ( C ) STRANDEDNESS: single
                ( D ) TOPOLOGY: linear ( i i ) MOLECULE TYPE: genomic DNA ( x i ) SEQUENCE DESCRIPTION: SEQ ID NO: 119:

GACGGAGCTG GGGCGGCCT                                                                                           19

( 2 ) INFORMATION FOR SEQ ID NO: 120:

( i ) SEQUENCE CHARACTERISTICS:
   ( A ) LENGTH: 18 base pairs
   ( B ) TYPE: nucleic acid
   ( C ) STRANDEDNESS: single
   ( D ) TOPOLOGY: linear ( i i ) MOLECULE TYPE: genomic DNA ( x i ) SEQUENCE DESCRIPTION: SEQ ID NO: 120:

GACTTCCTGG AGCGGAGG  18

( 2 ) INFORMATION FOR SEQ ID NO: 121:

( i ) SEQUENCE CHARACTERISTICS:
   ( A ) LENGTH: 18 base pairs
   ( B ) TYPE: nucleic acid
   ( C ) STRANDEDNESS: single
   ( D ) TOPOLOGY: linear ( i i ) MOLECULE TYPE: genomic DNA ( x i ) SEQUENCE DESCRIPTION: SEQ ID NO: 121:

GACCTCCTGG AGCGGAGG  18

( 2 ) INFORMATION FOR SEQ ID NO: 122:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( i i ) MOLECULE TYPE: genomic DNA ( x i ) SEQUENCE DESCRIPTION: SEQ ID NO: 122:

GAGCGGAGGC GTGCC  15

( 2 ) INFORMATION FOR SEQ ID NO: 123:

( i ) SEQUENCE CHARACTERISTICS:
   ( A ) LENGTH: 18 base pairs
   ( B ) TYPE: nucleic acid
   ( C ) STRANDEDNESS: single
   ( D ) TOPOLOGY: linear ( i i ) MOLECULE TYPE: genomic DNA ( x i ) SEQUENCE DESCRIPTION: SEQ ID NO: 123:

TCAGACGTAG AGTACTCC  18

( 2 ) INFORMATION FOR SEQ ID NO: 124:

( i ) SEQUENCE CHARACTERISTICS:
   ( A ) LENGTH: 21 base pairs
   ( B ) TYPE: nucleic acid
   ( C ) STRANDEDNESS: single
   ( D ) TOPOLOGY: linear ( i i ) MOLECULE TYPE: genomic DNA ( x i ) SEQUENCE DESCRIPTION: SEQ ID NO: 124:

TCTTGCAGCA GGATAAGTAT G  21

( 2 ) INFORMATION FOR SEQ ID NO: 125:

( i ) SEQUENCE CHARACTERISTICS:
   ( A ) LENGTH: 21 base pairs
   ( B ) TYPE: nucleic acid
   ( C ) STRANDEDNESS: single ( D ) TOPOLOGY: linear ( i i ) MOLECULE TYPE: genomic DNA ( x i ) SEQUENCE DESCRIPTION: SEQ ID NO: 125:

CACTCATGTT TAACCTGCTC C 21

( 2 ) INFORMATION FOR SEQ ID NO: 126:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 126:

TCAGACTTAC GCAGCTCC 18

( 2 ) INFORMATION FOR SEQ ID NO: 127:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 127:

TCAGACTTAA GCAGCTCC 18

( 2 ) INFORMATION FOR SEQ ID NO: 128:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 128:

GAGCAGAGGC GGAGC 15

( 2 ) INFORMATION FOR SEQ ID NO: 129:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 129:

GAGCAGAAGC GAGGCC 16

( 2 ) INFORMATION FOR SEQ ID NO: 130:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 130:

GGCCCGCTTC TGCTCCA 17

( 2 ) INFORMATION FOR SEQ ID NO: 131:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 131:

GCGGCCCGCT TCTGCTC 17

( 2 ) INFORMATION FOR SEQ ID NO: 132:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 132:

GAGCAGAAGC GAGGC 15

( 2 ) INFORMATION FOR SEQ ID NO: 133:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 133:

GGAGNAGAAG CNGGCCG 17

( 2 ) INFORMATION FOR SEQ ID NO: 134:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 134:

CCACCCGGCC CCGCTTCT 18

( 2 ) INFORMATION FOR SEQ ID NO: 135:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 135:

CATCCTGGAA GACAGGCG 18

( 2 ) INFORMATION FOR SEQ ID NO: 136:

( i ) SEQUENCE CHARACTERISTICS:
   ( A ) LENGTH: 19 base pairs
   ( B ) TYPE: nucleic acid
   ( C ) STRANDEDNESS: single
   ( D ) TOPOLOGY: linear ( i i ) MOLECULE TYPE: genomic DNA ( x i ) SEQUENCE DESCRIPTION: SEQ ID NO: 136:

CATCCTGGAA GACAGAGCG 19

( 2 ) INFORMATION FOR SEQ ID NO: 137:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: genomic DNA ( x i ) SEQUENCE DESCRIPTION: SEQ ID NO: 137:

GGCGGCCTAG CGCCGAGT 18

( 2 ) INFORMATION FOR SEQ ID NO: 138:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( i i ) MOLECULE TYPE: genomic DNA ( x i ) SEQUENCE DESCRIPTION: SEQ ID NO: 138:

ACCTCCTGGA GCGGAGG 17

( 2 ) INFORMATION FOR SEQ ID NO: 139:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( i i ) MOLECULE TYPE: genomic DNA ( x i ) SEQUENCE DESCRIPTION: SEQ ID NO: 139:

GACTTCCTGG AGCGGAG 17

( 2 ) INFORMATION FOR SEQ ID NO: 140:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: genomic DNA ( x i ) SEQUENCE DESCRIPTION: SEQ ID NO: 140:

CATCCTGGAG CAGGCG 16

( 2 ) INFORMATION FOR SEQ ID NO: 141:

( i ) SEQUENCE CHARACTERISTICS:
      ( A ) LENGTH: 17 base pairs
      ( B ) TYPE: nucleic acid
      ( C ) STRANDEDNESS: single ( D ) TOPOLOGY: linear ( i i ) MOLECULE TYPE: genomic DNA ( x i ) SEQUENCE DESCRIPTION: SEQ ID NO: 141:

ACCTCGGCCC NCCTCTG                                                                    17

( 2 ) INFORMATION FOR SEQ ID NO: 142:

( i ) SEQUENCE CHARACTERISTICS:
                ( A ) LENGTH: 13 base pairs
                ( B ) TYPE: nucleic acid
                ( C ) STRANDEDNESS: single
                ( D ) TOPOLOGY: linear ( i i ) MOLECULE TYPE: genomic DNA ( x i ) SEQUENCE DESCRIPTION: SEQ ID NO: 142:

GAGCAGAAGC GGG                                                                        13

( 2 ) INFORMATION FOR SEQ ID NO: 143:

( i ) SEQUENCE CHARACTERISTICS:
                ( A ) LENGTH: 16 base pairs
                ( B ) TYPE: nucleic acid
                ( C ) STRANDEDNESS: single
                ( D ) TOPOLOGY: linear ( i i ) MOLECULE TYPE: genomic DNA ( x i ) SEQUENCE DESCRIPTION: SEQ ID NO: 143:

GAGNAGAAGC NGGCCG                                                                     16

( 2 ) INFORMATION FOR SEQ ID NO: 144:

( i ) SEQUENCE CHARACTERISTICS:
                ( A ) LENGTH: 17 base pairs
                ( B ) TYPE: nucleic acid
                ( C ) STRANDEDNESS: single
                ( D ) TOPOLOGY: linear ( i i ) MOLECULE TYPE: genomic DNA ( x i ) SEQUENCE DESCRIPTION: SEQ ID NO: 144:

CCTCGGCCCN CCTCTGC                                                                    17

( 2 ) INFORMATION FOR SEQ ID NO: 145:

( i ) SEQUENCE CHARACTERISTICS:
                ( A ) LENGTH: 16 base pairs
                ( B ) TYPE: nucleic acid
                ( C ) STRANDEDNESS: single
                ( D ) TOPOLOGY: linear ( i i ) MOLECULE TYPE: genomic DNA ( x i ) SEQUENCE DESCRIPTION: SEQ ID NO: 145:

CCTCCTGGAG CGGAGG                                                                     16

( 2 ) INFORMATION FOR SEQ ID NO: 146:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( i i ) MOLECULE TYPE: genomic DNA ( x i ) SEQUENCE DESCRIPTION: SEQ ID NO: 146:

CGCCTGTCTT CCAGGATG    18

( 2 ) INFORMATION FOR SEQ ID NO: 147:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 147:

TTCTTGCAGC AGGATAAGTA TG    22

( 2 ) INFORMATION FOR SEQ ID NO: 148:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 148:

CGCCTGTCCT CCAGGATG    18

( 2 ) INFORMATION FOR SEQ ID NO: 149:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 149:

AGAAGCGGGG CCGGGTG    17

( 2 ) INFORMATION FOR SEQ ID NO: 150:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 150:

GAGCAGAGNC GGGCC    15

( 2 ) INFORMATION FOR SEQ ID NO: 151:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 151:

GAGCAGAGAG CGGGC    15

( 2 ) INFORMATION FOR SEQ ID NO: 152:

( i ) SEQUENCE CHARACTERISTICS:
 ( A ) LENGTH: 16 base pairs
 ( B ) TYPE: nucleic acid
 ( C ) STRANDEDNESS: single
 ( D ) TOPOLOGY: linear ( i i ) MOLECULE TYPE: genomic DNA ( x i ) SEQUENCE DESCRIPTION: SEQ ID NO: 152:

CTTCTGCTCC AGGAGG 16

( 2 ) INFORMATION FOR SEQ ID NO: 153:

( i ) SEQUENCE CHARACTERISTICS:
 ( A ) LENGTH: 15 base pairs
 ( B ) TYPE: nucleic acid
 ( C ) STRANDEDNESS: single
 ( D ) TOPOLOGY: linear ( i i ) MOLECULE TYPE: genomic DNA ( x i ) SEQUENCE DESCRIPTION: SEQ ID NO: 153:

CTCCTGGAGC AGAAG 15

( 2 ) INFORMATION FOR SEQ ID NO: 154:

( i ) SEQUENCE CHARACTERISTICS:
 ( A ) LENGTH: 16 base pairs
 ( B ) TYPE: nucleic acid
 ( C ) STRANDEDNESS: single
 ( D ) TOPOLOGY: linear ( i i ) MOLECULE TYPE: genomic DNA ( x i ) SEQUENCE DESCRIPTION: SEQ ID NO: 154:

CCTCCTGGAG CNGAAG 16

( 2 ) INFORMATION FOR SEQ ID NO: 155:

( i ) SEQUENCE CHARACTERISTICS:
 ( A ) LENGTH: 17 base pairs
 ( B ) TYPE: nucleic acid
 ( C ) STRANDEDNESS: single
 ( D ) TOPOLOGY: linear ( i i ) MOLECULE TYPE: genomic DNA ( x i ) SEQUENCE DESCRIPTION: SEQ ID NO: 155:

CCTCCTGGAG CAAGAAG 17

( 2 ) INFORMATION FOR SEQ ID NO: 156:

( i ) SEQUENCE CHARACTERISTICS:
 ( A ) LENGTH: 16 base pairs
 ( B ) TYPE: nucleic acid
 ( C ) STRANDEDNESS: single
 ( D ) TOPOLOGY: linear ( i i ) MOLECULE TYPE: genomic DNA ( x i ) SEQUENCE DESCRIPTION: SEQ ID NO: 156:

CGGCCCGCCT CTGCTC 16

( 2 ) INFORMATION FOR SEQ ID NO: 157:

( i ) SEQUENCE CHARACTERISTICS:
 ( A ) LENGTH: 17 base pairs
 ( B ) TYPE: nucleic acid
 ( C ) STRANDEDNESS: single (D) TOPOLOGY: linear (i i) MOLECULE TYPE: genomic DNA (x i) SEQUENCE DESCRIPTION: SEQ ID NO: 157:

CGGGGCTGTG GAGAGCT 17

(2) INFORMATION FOR SEQ ID NO: 158:

(i) SEQUENCE CHARACTERISTICS:
(A) LENGTH: 18 base pairs
(B) TYPE: nucleic acid
(C) STRANDEDNESS: single
(D) TOPOLOGY: linear (i i) MOLECULE TYPE: genomic DNA (x i) SEQUENCE DESCRIPTION: SEQ ID NO: 158:

CTTCTGCTCC AGGAGGTC 18

(2) INFORMATION FOR SEQ ID NO: 159:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: genomic DNA (x i) SEQUENCE DESCRIPTION: SEQ ID NO: 159:

ACCTCCTGGA GCAGAAG 17

(2) INFORMATION FOR SEQ ID NO: 160:

(i) SEQUENCE CHARACTERISTICS:
(A) LENGTH: 15 base pairs
(B) TYPE: nucleic acid
(C) STRANDEDNESS: single
(D) TOPOLOGY: linear (i i) MOLECULE TYPE: genomic DNA (x i) SEQUENCE DESCRIPTION: SEQ ID NO: 160:

GGCCCGCCTC TGCTC 15

(2) INFORMATION FOR SEQ ID NO: 161:

(i) SEQUENCE CHARACTERISTICS:
(A) LENGTH: 14 base pairs
(B) TYPE: nucleic acid
(C) STRANDEDNESS: single
(D) TOPOLOGY: linear (i i) MOLECULE TYPE: genomic DNA (x i) SEQUENCE DESCRIPTION: SEQ ID NO: 161:

GCCCGCCTCT GCTC 14

(2) INFORMATION FOR SEQ ID NO: 162:

(i) SEQUENCE CHARACTERISTICS:
(A) LENGTH: 13 base pairs
(B) TYPE: nucleic acid
(C) STRANDEDNESS: single
(D) TOPOLOGY: linear (i i) MOLECULE TYPE: genomic DNA (x i) SEQUENCE DESCRIPTION: SEQ ID NO: 162:

GGCCCGCCTC TGC 13

( 2 ) INFORMATION FOR SEQ ID NO: 163:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 163:

GAGGCGCGCC GAGGT 15

( 2 ) INFORMATION FOR SEQ ID NO: 164:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 164:

GAGGCGCGCC GAGGTG 16

( 2 ) INFORMATION FOR SEQ ID NO: 165:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 165:

GAGGCGCGCC GAGGTGGA 18

( 2 ) INFORMATION FOR SEQ ID NO: 166:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 166:

AGAAGCGGGG CCGGGT 16

( 2 ) INFORMATION FOR SEQ ID NO: 167:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 167:

AGAAGCGGGG CCGGG 15

( 2 ) INFORMATION FOR SEQ ID NO: 168:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (ii) MOLECULE TYPE: genomic DNA (xi) SEQUENCE DESCRIPTION: SEQ ID NO: 168:

GGGGTTGGTG AGAGCT 16

(2) INFORMATION FOR SEQ ID NO: 169:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (ii) MOLECULE TYPE: genomic DNA (xi) SEQUENCE DESCRIPTION: SEQ ID NO: 169:

GGGGTTGTGG AGAGCT 16

(2) INFORMATION FOR SEQ ID NO: 170:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (ii) MOLECULE TYPE: genomic DNA (xi) SEQUENCE DESCRIPTION: SEQ ID NO: 170:

ACCTCGGCCC GCCTC 15

(2) INFORMATION FOR SEQ ID NO: 171:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: genomic DNA (xi) SEQUENCE DESCRIPTION: SEQ ID NO: 171:

CATCCTGGAA GACAGGC 17

(2) INFORMATION FOR SEQ ID NO: 172:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (ii) MOLECULE TYPE: genomic DNA (xi) SEQUENCE DESCRIPTION: SEQ ID NO: 172:

GAGCAGAAGC AGGCC 15

(2) INFORMATION FOR SEQ ID NO: 173:

(i) SEQUENCE CHARACTERISTICS:
    (A) LENGTH: 20 base pairs
    (B) TYPE: nucleic acid
    (C) STRANDEDNESS: single ( D ) TOPOLOGY: linear ( i i ) MOLECULE TYPE: genomic DNA ( x i ) SEQUENCE DESCRIPTION: SEQ ID NO: 173:

GGCGGCCTAG CGCCGAGTAC 20

( 2 ) INFORMATION FOR SEQ ID NO: 174:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 174:

TGTAGGACCT TCTGTCCG 18

( 2 ) INFORMATION FOR SEQ ID NO: 175:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 175:

GTAGGACCTT CTGTCCG 17

( 2 ) INFORMATION FOR SEQ ID NO: 176:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 176:

TTCTTGCAGC AGGATAAGTA TGAG 24

( 2 ) INFORMATION FOR SEQ ID NO: 177:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 177:

CTCCCGTTTA TGGATGTATC 20

( 2 ) INFORMATION FOR SEQ ID NO: 178:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 178:

CAGTACTCCT CATCAGGC                                                                            18

( 2 ) INFORMATION FOR SEQ ID NO: 179:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 179:

CTGTCCAGGT ACCGCA                                                                              16

( 2 ) INFORMATION FOR SEQ ID NO: 180:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 180:

ACCTCGGCCC GCCTCT                                                                              16

( 2 ) INFORMATION FOR SEQ ID NO: 181:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 181:

GAGGCGCGCC GAGGTGGAC                                                                           19

( 2 ) INFORMATION FOR SEQ ID NO: 182:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 182:

AGAGGCGCGC CGAGGTGGAC                                                                          20

( 2 ) INFORMATION FOR SEQ ID NO: 183:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 183:

AGAAGCGGGG CCGG                                                                                14

( 2 ) INFORMATION FOR SEQ ID NO: 184:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 184:

GAAGCGGGGC CGGG 14

( 2 ) INFORMATION FOR SEQ ID NO: 185:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 185:

GAAGACAGGC GGGCCCTGG 19

( 2 ) INFORMATION FOR SEQ ID NO: 186:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 186:

GCCTGTCTTC CAGGAAGTCC 20

( 2 ) INFORMATION FOR SEQ ID NO: 187:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 187:

CTCAGACGTA GAGTACTCC 19

( 2 ) INFORMATION FOR SEQ ID NO: 188:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 188:

GCCTGCTGCG GAGCACTGG 19

( 2 ) INFORMATION FOR SEQ ID NO: 189:

( i ) SEQUENCE CHARACTERISTICS:
    ( A ) LENGTH: 18 base pairs
    ( B ) TYPE: nucleic acid
    ( C ) STRANDEDNESS: single ( D ) TOPOLOGY: linear ( i i ) MOLECULE TYPE: genomic DNA ( x i ) SEQUENCE DESCRIPTION: SEQ ID NO: 189:

GACCTCCTGG AAGACAGG 18

( 2 ) INFORMATION FOR SEQ ID NO: 190:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 190:

CCTGTCCTCC AGGAGGTC 18

( 2 ) INFORMATION FOR SEQ ID NO: 191:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 191:

ACGGGGTTGG TGAGAGCTT 19

( 2 ) INFORMATION FOR SEQ ID NO: 192:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 192:

ACGGGGTTGT GGAGAGCTT 19

( 2 ) INFORMATION FOR SEQ ID NO: 193:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 193:

ACGGGGCTGT GGAGAGCTT 19

( 2 ) INFORMATION FOR SEQ ID NO: 194:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 194:

GAGGCGGGCC GAGGT                                                                15

( 2 ) INFORMATION FOR SEQ ID NO: 195:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 195:

GAGGCGGGCC GAGGTG                                                               16

( 2 ) INFORMATION FOR SEQ ID NO: 196:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 196:

GAGGCGGGCC GAGGTGGA                                                             18

( 2 ) INFORMATION FOR SEQ ID NO: 197:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 197:

GAGGCGGGCC GAGGTGGAC                                                            19

( 2 ) INFORMATION FOR SEQ ID NO: 198:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 198:

AGAGGCGGGC CGAGGTGGAC                                                           20

( 2 ) INFORMATION FOR SEQ ID NO: 199:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 199:

GGCGGCCTAG CGCCGAGTA                                                            19

( 2 ) INFORMATION FOR SEQ ID NO: 200:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: genomic DNA ( x i ) SEQUENCE DESCRIPTION: SEQ ID NO: 200:

CCACNCGGCC CCGCTTCT                     18

( 2 ) INFORMATION FOR SEQ ID NO: 201:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( i i ) MOLECULE TYPE: genomic DNA ( x i ) SEQUENCE DESCRIPTION: SEQ ID NO: 201:

GAGGCGGGCC GCGGT                        15

( 2 ) INFORMATION FOR SEQ ID NO: 202:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( i i ) MOLECULE TYPE: genomic DNA ( x i ) SEQUENCE DESCRIPTION: SEQ ID NO: 202:

ACCGCGGCCC GCCTC                        15

( 2 ) INFORMATION FOR SEQ ID NO: 203:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( i i ) MOLECULE TYPE: genomic DNA ( x i ) SEQUENCE DESCRIPTION: SEQ ID NO: 203:

GAAGCGGGCC GCGGT                        15

( 2 ) INFORMATION FOR SEQ ID NO: 204:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( i i ) MOLECULE TYPE: genomic DNA ( x i ) SEQUENCE DESCRIPTION: SEQ ID NO: 204:

ACCGCGGCCC GCTTC                        15

( 2 ) INFORMATION FOR SEQ ID NO: 205:

( i ) SEQUENCE CHARACTERISTICS:
            ( A ) LENGTH: 17 base pairs
            ( B ) TYPE: nucleic acid
            ( C ) STRANDEDNESS: single (D) TOPOLOGY: linear (ii) MOLECULE TYPE: genomic DNA (xi) SEQUENCE DESCRIPTION: SEQ ID NO: 205:

ACTTCCTGGA AGACAGG 17

(2) INFORMATION FOR SEQ ID NO: 206:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: genomic DNA (xi) SEQUENCE DESCRIPTION: SEQ ID NO: 206:

CGCAAGTCCT CCTCTTG 17

(2) INFORMATION FOR SEQ ID NO: 207:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: genomic DNA (xi) SEQUENCE DESCRIPTION: SEQ ID NO: 207:

CAAGAGGAGG ACTTGCG 17

(2) INFORMATION FOR SEQ ID NO: 208:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: genomic DNA (xi) SEQUENCE DESCRIPTION: SEQ ID NO: 208:

GAAGACAGGC GGGCCCTG 18

(2) INFORMATION FOR SEQ ID NO: 209:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: genomic DNA (xi) SEQUENCE DESCRIPTION: SEQ ID NO: 209:

AAGACAGGCG GGCCCTGG 18

(2) INFORMATION FOR SEQ ID NO: 210:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: genomic DNA (xi) SEQUENCE DESCRIPTION: SEQ ID NO: 210:

ACTTCCTGGA AGACGAG    17

( 2 ) INFORMATION FOR SEQ ID NO: 211:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 211:

ACTTCCTGGA AGACGAGC    18

( 2 ) INFORMATION FOR SEQ ID NO: 212:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 212:

ACATCCTGGA AGACAGGC    18

( 2 ) INFORMATION FOR SEQ ID NO: 213:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 213:

GCCTGTCTTC CAGGATG    17

( 2 ) INFORMATION FOR SEQ ID NO: 214:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 214:

GCAGAAGCGG GCCGCG    16

( 2 ) INFORMATION FOR SEQ ID NO: 215:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 215:

CGCGGCCCGC TTCTGC    16

( 2 ) INFORMATION FOR SEQ ID NO: 216:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (ii) MOLECULE TYPE: genomic DNA (xi) SEQUENCE DESCRIPTION: SEQ ID NO: 216:

GCAGAGGCGG GCCGCG                                                                                       16

(2) INFORMATION FOR SEQ ID NO: 217:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (ii) MOLECULE TYPE: genomic DNA (xi) SEQUENCE DESCRIPTION: SEQ ID NO: 217:

CGCGGCCCGC CTCTGC                                                                                       16

(2) INFORMATION FOR SEQ ID NO: 218:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (ii) MOLECULE TYPE: genomic DNA (xi) SEQUENCE DESCRIPTION: SEQ ID NO: 218:

GCAGAGGCGG GCCGAG                                                                                       16

(2) INFORMATION FOR SEQ ID NO: 219:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (ii) MOLECULE TYPE: genomic DNA (xi) SEQUENCE DESCRIPTION: SEQ ID NO: 219:

CTCGGCCCGC CTCTGC                                                                                       16

(2) INFORMATION FOR SEQ ID NO: 220:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (ii) MOLECULE TYPE: genomic DNA (xi) SEQUENCE DESCRIPTION: SEQ ID NO: 220:

GCGGAGGCGG GCCGAG                                                                                       16

(2) INFORMATION FOR SEQ ID NO: 221:

(i) SEQUENCE CHARACTERISTICS:
    (A) LENGTH: 16 base pairs
    (B) TYPE: nucleic acid
    (C) STRANDEDNESS: single (D) TOPOLOGY: linear (ii) MOLECULE TYPE: genomic DNA (xi) SEQUENCE DESCRIPTION: SEQ ID NO: 221:

CTCGGCCCGC CTCCGC 16

(2) INFORMATION FOR SEQ ID NO: 222:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 222:

CTCCGCTCCA GGAAGTC 17

(2) INFORMATION FOR SEQ ID NO: 223:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 223:

CGGGGTTGGT GAGAGCT 17

(2) INFORMATION FOR SEQ ID NO: 224:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 224:

CGGGGTTGTG GAGAGCT 17

(2) INFORMATION FOR SEQ ID NO: 225:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 225:

CGGGGCTGTG GAGAGCTT 18

(2) INFORMATION FOR SEQ ID NO: 226:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 226:

TGTCCACCGC GGCCCGCGCC T                                                                           21

( 2 ) INFORMATION FOR SEQ ID NO: 227:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 227:

CCGAATTCGC CGCTGCACTG TGAAGCT                                                                     27

( 2 ) INFORMATION FOR SEQ ID NO: 228:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 228:

CCCCGTAGTT GTGTCTGCAC ACGG                                                                        24

( 2 ) INFORMATION FOR SEQ ID NO: 229:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 229:

GAATTCCCAG CTCACACGGG ACT                                                                         23

( 2 ) INFORMATION FOR SEQ ID NO: 230:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 230:

GGTGTCCACC GCGGCCCGCG C                                                                           21

( 2 ) INFORMATION FOR SEQ ID NO: 231:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 231:

AACCCCGTAG TTGTGTCTGC ACAC                                                                        24

( 2 ) INFORMATION FOR SEQ ID NO: 232:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 232:

GGGGGAGTTC CGGG 14

( 2 ) INFORMATION FOR SEQ ID NO: 233:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 233:

CCCGGTACTC CCCC 14

( 2 ) INFORMATION FOR SEQ ID NO: 234:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 234:

CGCGGCCCGC CTCTG 15

( 2 ) INFORMATION FOR SEQ ID NO: 235:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 235:

CCGCGGCCCG CCTCTG 16

( 2 ) INFORMATION FOR SEQ ID NO: 236:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 236:

CCGNGGCCCG CCTCTGC 17

( 2 ) INFORMATION FOR SEQ ID NO: 237:

( i ) SEQUENCE CHARACTERISTICS:
        ( A ) LENGTH: 18 base pairs
        ( B ) TYPE: nucleic acid
        ( C ) STRANDEDNESS: single (D) TOPOLOGY: linear (ii) MOLECULE TYPE: genomic DNA (xi) SEQUENCE DESCRIPTION: SEQ ID NO: 237:

CCAGCGGCCC GCCTCTGC 18

(2) INFORMATION FOR SEQ ID NO: 238:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 238:

GCAGAANCGG GCCGCNGT 18

(2) INFORMATION FOR SEQ ID NO: 239:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 239:

GCAGAAAGCG GGCCGCNGT 19

(2) INFORMATION FOR SEQ ID NO: 240:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 240:

CAGAAGCGGG CCGCG 15

(2) INFORMATION FOR SEQ ID NO: 241:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 241:

ACCTNGGCCC GCCNCTGC 18

(2) INFORMATION FOR SEQ ID NO: 242:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 242:

ACCTNGGCCC GCCNCTG                                                                17

( 2 ) INFORMATION FOR SEQ ID NO: 243:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 243:

GGAGCAGAAA CGGGCCG                                                                17

( 2 ) INFORMATION FOR SEQ ID NO: 244:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 244:

GGAGCAGAAA CGGGCCGC                                                               18

( 2 ) INFORMATION FOR SEQ ID NO: 245:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 245:

GCAGAAGCGG GCCNCG                                                                 16

( 2 ) INFORMATION FOR SEQ ID NO: 246:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 246:

GTCCACCTCG GCCCG                                                                  15

( 2 ) INFORMATION FOR SEQ ID NO: 247:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 247:

CGGGCCGCGG TGGAC                                                                  15

( 2 ) INFORMATION FOR SEQ ID NO: 248:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 248:

CGCCTCCGCT CCAGGAG 17

( 2 ) INFORMATION FOR SEQ ID NO: 249:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 249:

CTCCTGGAGC AGAGGCG 17

( 2 ) INFORMATION FOR SEQ ID NO: 250:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 250:

ACCGCGGCCC GCCTCT 16

( 2 ) INFORMATION FOR SEQ ID NO: 251:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 251:

CACCTNGGCC CGCCNCTG 18

( 2 ) INFORMATION FOR SEQ ID NO: 252:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 252:

CGNGGCCCGC CTCTG 15

( 2 ) INFORMATION FOR SEQ ID NO: 253:

( i ) SEQUENCE CHARACTERISTICS:
    ( A ) LENGTH: 16 base pairs
    ( B ) TYPE: nucleic acid
    ( C ) STRANDEDNESS: single ( D ) TOPOLOGY: linear ( i i ) MOLECULE TYPE: genomic DNA ( x i ) SEQUENCE DESCRIPTION: SEQ ID NO: 253:

CCGNGGCCCG CCTCTG 16

( 2 ) INFORMATION FOR SEQ ID NO: 254:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 254:

GGGGGAGTTC CGGGCG 16

( 2 ) INFORMATION FOR SEQ ID NO: 255:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 255:

CGCCCGGTAC TCCCCC 16

( 2 ) INFORMATION FOR SEQ ID NO: 256:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 256:

NCCTGATGCC GAGTACTG 18

( 2 ) INFORMATION FOR SEQ ID NO: 257:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 257:

NCGGGGCTGT GGAGAGCTT 19

( 2 ) INFORMATION FOR SEQ ID NO: 258:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 258:

CTACGGGGCT GTGGAGAG    18

( 2 ) INFORMATION FOR SEQ ID NO: 259:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 259:

CTACGGGNCT GTGGAGAG    18

( 2 ) INFORMATION FOR SEQ ID NO: 260:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 260:

GTTCCGGGCG GTGAC    15

( 2 ) INFORMATION FOR SEQ ID NO: 261:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 261:

GGGGGAGTTN CGGGG    15

( 2 ) INFORMATION FOR SEQ ID NO: 262:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 262:

CGTCACCGCC CGGTAC    16

( 2 ) INFORMATION FOR SEQ ID NO: 263:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 263:

CGTCACCGCC CGNTAC    16

( 2 ) INFORMATION FOR SEQ ID NO: 264:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 264:

CACCCCTCAT NGCCC     15

( 2 ) INFORMATION FOR SEQ ID NO: 265:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 265:

GCGGGCCGCG GTGGAC     16

( 2 ) INFORMATION FOR SEQ ID NO: 266:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 266:

CAGAGGCNGG CCGCGGT     17

( 2 ) INFORMATION FOR SEQ ID NO: 267:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 267:

GTTNCGGGCG GTGAC     15

( 2 ) INFORMATION FOR SEQ ID NO: 268:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 268:

TTCCGGGCGG TGAC     14

( 2 ) INFORMATION FOR SEQ ID NO: 269:

( i ) SEQUENCE CHARACTERISTICS:
        ( A ) LENGTH: 13 base pairs
        ( B ) TYPE: nucleic acid
        ( C ) STRANDEDNESS: single ( D ) TOPOLOGY: linear ( i i ) MOLECULE TYPE: genomic DNA ( x i ) SEQUENCE DESCRIPTION: SEQ ID NO: 269:

GGGGAGTTCC GGG                                                                                  13

( 2 ) INFORMATION FOR SEQ ID NO: 270:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 270:

TCACCGCCCG GAAC                                                                                 14

( 2 ) INFORMATION FOR SEQ ID NO: 271:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 271:

AGATACTTCT ATAACCAG                                                                             18

( 2 ) INFORMATION FOR SEQ ID NO: 272:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 272:

AGACACTTCT ATAACCAG                                                                             18

( 2 ) INFORMATION FOR SEQ ID NO: 273:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 273:

CTGGTTATAG AAGTATCT                                                                             18

( 2 ) INFORMATION FOR SEQ ID NO: 274:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 274:

CTGTCGCCGA GTCCTGG                                                                                          17

( 2 ) INFORMATION FOR SEQ ID NO: 275:

( i ) SEQUENCE CHARACTERISTICS:
           ( A ) LENGTH: 19 base pairs
           ( B ) TYPE: nucleic acid
           ( C ) STRANDEDNESS: single
           ( D ) TOPOLOGY: linear ( i i ) MOLECULE TYPE: genomic DNA ( x i ) SEQUENCE DESCRIPTION: SEQ ID NO: 275:

GGGCGGCCTA GCGCCGAGT                                                                                       19

( 2 ) INFORMATION FOR SEQ ID NO: 276:

( i ) SEQUENCE CHARACTERISTICS:
           ( A ) LENGTH: 19 base pairs
           ( B ) TYPE: nucleic acid
           ( C ) STRANDEDNESS: single
           ( D ) TOPOLOGY: linear ( i i ) MOLECULE TYPE: genomic DNA ( x i ) SEQUENCE DESCRIPTION: SEQ ID NO: 276:

GCAGAAAGCG GGCCGCNGT                                                                                       19

( 2 ) INFORMATION FOR SEQ ID NO: 277:

( i ) SEQUENCE CHARACTERISTICS:
           ( A ) LENGTH: 19 base pairs
           ( B ) TYPE: nucleic acid
           ( C ) STRANDEDNESS: single
           ( D ) TOPOLOGY: linear ( i i ) MOLECULE TYPE: genomic DNA ( x i ) SEQUENCE DESCRIPTION: SEQ ID NO: 277:

GCGNCTGTCT TCCAGGATG                                                                                       19

( 2 ) INFORMATION FOR SEQ ID NO: 278:

( i ) SEQUENCE CHARACTERISTICS:
           ( A ) LENGTH: 18 base pairs
           ( B ) TYPE: nucleic acid
           ( C ) STRANDEDNESS: single
           ( D ) TOPOLOGY: linear ( i i ) MOLECULE TYPE: genomic DNA ( x i ) SEQUENCE DESCRIPTION: SEQ ID NO: 278:

CGNCTGTCTT CCAGGATG                                                                                        18

( 2 ) INFORMATION FOR SEQ ID NO: 279:

( i ) SEQUENCE CHARACTERISTICS:
           ( A ) LENGTH: 17 base pairs
           ( B ) TYPE: nucleic acid
           ( C ) STRANDEDNESS: single
           ( D ) TOPOLOGY: linear ( i i ) MOLECULE TYPE: genomic DNA ( x i ) SEQUENCE DESCRIPTION: SEQ ID NO: 279:

ACCGNGGCCC GCCTCTG                                                                                         17

( 2 ) INFORMATION FOR SEQ ID NO: 280:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( i i ) MOLECULE TYPE: genomic DNA ( x i ) SEQUENCE DESCRIPTION: SEQ ID NO: 280:

CCGTCACCGC CCGNTAC                                                                17

( 2 ) INFORMATION FOR SEQ ID NO: 281:

( i ) SEQUENCE CHARACTERISTICS:
  ( A ) LENGTH: 14 base pairs
  ( B ) TYPE: nucleic acid
  ( C ) STRANDEDNESS: single
  ( D ) TOPOLOGY: linear ( i i ) MOLECULE TYPE: genomic DNA ( x i ) SEQUENCE DESCRIPTION: SEQ ID NO: 281:

GGGGAGTTCC GGGG                                                                   14

( 2 ) INFORMATION FOR SEQ ID NO: 282:

( i ) SEQUENCE CHARACTERISTICS:
  ( A ) LENGTH: 16 base pairs
  ( B ) TYPE: nucleic acid
  ( C ) STRANDEDNESS: single
  ( D ) TOPOLOGY: linear ( i i ) MOLECULE TYPE: genomic DNA ( x i ) SEQUENCE DESCRIPTION: SEQ ID NO: 282:

TCACCGCCCG GAACTC                                                                 16

( 2 ) INFORMATION FOR SEQ ID NO: 283:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: genomic DNA ( x i ) SEQUENCE DESCRIPTION: SEQ ID NO: 283:

TGACACTTAT ACTTACCCTG C                                                           21

( 2 ) INFORMATION FOR SEQ ID NO: 284:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: genomic DNA ( x i ) SEQUENCE DESCRIPTION: SEQ ID NO: 284:

TTGAAGCAGG ATAAGTTTGA G                                                           21

( 2 ) INFORMATION FOR SEQ ID NO: 285:

( i ) SEQUENCE CHARACTERISTICS:
  ( A ) LENGTH: 20 base pairs
  ( B ) TYPE: nucleic acid
  ( C ) STRANDEDNESS: single (D) TOPOLOGY: linear (ii) MOLECULE TYPE: genomic DNA (xi) SEQUENCE DESCRIPTION: SEQ ID NO: 285:

CTTGAAGCAG GATAAGTTTG 20

(2) INFORMATION FOR SEQ ID NO: 286:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 286:

GAATTCCCGC GCCGCGCTCA 20

(2) INFORMATION FOR SEQ ID NO: 287:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 287:

GAATTCCCGC GCCGCG 16

(2) INFORMATION FOR SEQ ID NO: 288:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 288:

GAATTCCCGC GCCGCGCTCA C 21

(2) INFORMATION FOR SEQ ID NO: 289:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 289:

ATGACACTCC CTCTTAGGCT G 21

(2) INFORMATION FOR SEQ ID NO: 290:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 290:

ACATCCTGGA AGACGAG                                                          17

(2) INFORMATION FOR SEQ ID NO: 291:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 291:

CCGCTCCGTC CCATTGAA                                                         18

(2) INFORMATION FOR SEQ ID NO: 292:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 292:

TTCAATGAGA CGGAGCGG                                                         18

(2) INFORMATION FOR SEQ ID NO: 293:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 293:

CATCCTGGAA GACGAG                                                           16

(2) INFORMATION FOR SEQ ID NO: 294:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 294:

GCTCGTCTTC CAGCATG                                                          17

(2) INFORMATION FOR SEQ ID NO: 295:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 295:

CGCTCGTCTT CCAGGATG                                                         18

(2) INFORMATION FOR SEQ ID NO: 296:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: genomic DNA (xi) SEQUENCE DESCRIPTION: SEQ ID NO: 296:

GCTGTCGCCG AGTCCTGG                          18

(2) INFORMATION FOR SEQ ID NO: 297:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: genomic DNA (xi) SEQUENCE DESCRIPTION: SEQ ID NO: 297:

CCTGTCGCCG AGTCCTGG                          18

(2) INFORMATION FOR SEQ ID NO: 298:

(i) SEQUENCE CHARACTERISTICS:
(A) LENGTH: 16 base pairs
(B) TYPE: nucleic acid
(C) STRANDEDNESS: single
(D) TOPOLOGY: linear (ii) MOLECULE TYPE: genomic DNA (xi) SEQUENCE DESCRIPTION: SEQ ID NO: 298:

CTGTCCAGGT ACCGCA                            16

(2) INFORMATION FOR SEQ ID NO: 299:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: genomic DNA (xi) SEQUENCE DESCRIPTION: SEQ ID NO: 299:

GGCGGCCTAG CGCCGAGTA                         19

(2) INFORMATION FOR SEQ ID NO: 300:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: genomic DNA (xi) SEQUENCE DESCRIPTION: SEQ ID NO: 300:

CCACNCGGCC CCGCTTCT                          18

(2) INFORMATION FOR SEQ ID NO: 301:

(i) SEQUENCE CHARACTERISTICS:
(A) LENGTH: 15 base pairs
(B) TYPE: nucleic acid
(C) STRANDEDNESS: single (D) TOPOLOGY: linear (ii) MOLECULE TYPE: genomic DNA (xi) SEQUENCE DESCRIPTION: SEQ ID NO: 301:

GAGGCGGGCC GCGGT 15

(2) INFORMATION FOR SEQ ID NO: 302:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 302:

ACCGCGGCCC GCCTC 15

(2) INFORMATION FOR SEQ ID NO: 303:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 303:

GAAGCGGGCC GCGGT 15

(2) INFORMATION FOR SEQ ID NO: 304:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 304:

ACCGCGGCCC GCTTC 15

(2) INFORMATION FOR SEQ ID NO: 305:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 305:

ACTTCCTGGA AGACAGG 17

(2) INFORMATION FOR SEQ ID NO: 306:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 306:

GACCTCCTGG AAGACAGG 18

( 2 ) INFORMATION FOR SEQ ID NO: 307:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 307:

ACATCCTGGA AGACAAGC 18

( 2 ) INFORMATION FOR SEQ ID NO: 308:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 308:

GACATCCTGG AAGACAAGC 19

( 2 ) INFORMATION FOR SEQ ID NO: 309:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 309:

ACATCCTGGA AGACAAGCG 19

( 2 ) INFORMATION FOR SEQ ID NO: 310:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 310:

GAATTCCCGC GCCGCGCTCA CCTC 24

( 2 ) INFORMATION FOR SEQ ID NO: 311:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 311:

GAATTCACAG GGACTCCAGG CC 22

( 2 ) INFORMATION FOR SEQ ID NO: 312:

( i ) SEQUENCE CHARACTERISTICS:
   ( A ) LENGTH: 24 base pairs
   ( B ) TYPE: nucleic acid
   ( C ) STRANDEDNESS: single
   ( D ) TOPOLOGY: linear ( i i ) MOLECULE TYPE: genomic DNA ( x i ) SEQUENCE DESCRIPTION: SEQ ID NO: 312:

CGCTGCACTG TGAAGCTCTC ACCA                                          24

( 2 ) INFORMATION FOR SEQ ID NO: 313:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( i i ) MOLECULE TYPE: genomic DNA ( x i ) SEQUENCE DESCRIPTION: SEQ ID NO: 313:

CGCTGCACTG TGAAGCTCTC CACA                                          24

( 2 ) INFORMATION FOR SEQ ID NO: 314:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: genomic DNA ( x i ) SEQUENCE DESCRIPTION: SEQ ID NO: 314:

GGTGAGCGCG GCGCGGCGGG G                                             21

( 2 ) INFORMATION FOR SEQ ID NO: 315:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: genomic DNA ( x i ) SEQUENCE DESCRIPTION: SEQ ID NO: 315:

GGTGAGCATG TCGGGGGCG G                                              21